US012496204B2

(12) United States Patent
Barbarino et al.

(10) Patent No.: US 12,496,204 B2
(45) Date of Patent: Dec. 16, 2025

(54) FEEDBACK AND CALIBRATION SYSTEM FOR COSMETIC APPLICATOR CONFIGURED FOR USERS WITH LIMITED MOBILITY

(71) Applicant: L'OREAL, Paris (FR)

(72) Inventors: Casey Barbarino, San Anselmo, CA (US); Shivya Bansal, Somerset, NJ (US); Gregoire Charraud, Jersey City, NJ (US)

(73) Assignee: L'OREAL, Paris (FR)

( * ) Notice: Subject to any disclaimer, the term of this patent is extended or adjusted under 35 U.S.C. 154(b) by 530 days.

(21) Appl. No.: 18/148,930

(22) Filed: Dec. 30, 2022

(65) Prior Publication Data

US 2024/0216159 A1 Jul. 4, 2024

(51) Int. Cl.
*A61F 4/00* (2006.01)
*A61B 5/11* (2006.01)

(52) U.S. Cl.
CPC .............. *A61F 4/00* (2013.01); *A61B 5/1101* (2013.01); *A61H 2201/5058* (2013.01)

(58) Field of Classification Search
CPC .......... A45D 44/00; A45D 34/04; G06F 3/01; G06T 7/73; F16F 15/005
USPC ........................................................... 623/65
See application file for complete search history.

(56) References Cited

U.S. PATENT DOCUMENTS

| | | | |
|---|---|---|---|
| 9,925,034 | B2 | 3/2018 | Pathak |
| 10,070,807 | B2 | 9/2018 | Shoeb et al. |
| 10,101,824 | B2 * | 10/2018 | Pathak ................ G06F 3/03545 |
| 10,159,432 | B1 | 12/2018 | Pathak et al. |
| 10,219,930 | B2 | 3/2019 | Pathak et al. |
| 10,271,770 | B2 | 4/2019 | Pathak et al. |
| 10,368,669 | B2 | 8/2019 | Pathak |

(Continued)

FOREIGN PATENT DOCUMENTS

| | | |
|---|---|---|
| EP | 3 332 694 B1 | 4/2020 |

OTHER PUBLICATIONS

Preliminary Search Report and Written Opinion issued Oct. 9, 2023, for corresponding French Patent Application No. FR2303316 (with English Translation of Category of Cited Documents), 10 pages.

*Primary Examiner* — Nitin Patel
(74) *Attorney, Agent, or Firm* — Womble Bond Dickinson (US) LLP

(57) ABSTRACT

A system is provided that stabilizes an applicator in response to the motion caused by a user. A motion stabilizer includes a receiver configured to be coupled with the adapter; at least one sensor configured to detect a movement caused by a user; circuitry configured to determine a compensation movement to offset the detected movement; and at least one motion generation device embedded in the receiver configured to control a motion of the cosmetic applicator according to the determined compensation movement. An application is configured to capture an image of the user prior to a session of applying a cosmetic using the cosmetic applicator; capture an image of the user after the session of applying a cosmetic using the cosmetic applicator; detect an error in applying the cosmetic to a portion of the user's body; detect a deviation in the movement of the cosmetic applicator during the session when the error is detected; and adjust settings for the motion stabilizer to compensate for the deviation.

12 Claims, 63 Drawing Sheets

(56) References Cited

U.S. PATENT DOCUMENTS

| | | | | |
|---|---|---|---|---|
| 10,455,963 | B2 | 10/2019 | Pathak | |
| 10,583,061 | B2 | 3/2020 | Pathak et al. | |
| 10,600,596 | B2 | 3/2020 | Pathak | |
| 10,758,388 | B2 | 9/2020 | Pathak et al. | |
| 11,058,598 | B2 | 7/2021 | Pathak et al. | |
| 11,458,062 | B2 | 10/2022 | Pang et al. | |
| 12,300,035 | B1 * | 5/2025 | Xu | G06V 10/764 |
| 2013/0216295 | A1 * | 8/2013 | Wong | A45D 44/00 401/195 |
| 2020/0352306 | A1 * | 11/2020 | Um | A61L 2/26 |
| 2023/0042296 | A1 * | 2/2023 | Donohue | A45D 44/02 |
| 2023/0157435 | A1 * | 5/2023 | Mehta | B05B 12/122 132/200 |
| 2023/0290082 | A1 * | 9/2023 | Amberg | G06T 15/04 |
| 2024/0108119 | A1 * | 4/2024 | Hong | G06T 7/246 |
| 2024/0127563 | A1 * | 4/2024 | Koujan | G06T 19/20 |
| 2025/0014189 | A1 * | 1/2025 | Yuksel | G06T 7/70 |
| 2025/0113907 | A1 * | 4/2025 | Fei | A45D 34/04 |
| 2025/0120496 | A1 * | 4/2025 | Geer | A45D 44/002 |
| 2025/0157109 | A1 * | 5/2025 | Li | G06T 7/248 |

* cited by examiner

3801

FEEDBACK AND CALIBRATION SYSTEM FOR COSMETIC APPLICATOR CONFIGURED FOR USERS WITH LIMITED MOBILITY

FIELD

The present disclosure describes a system and features related to a device for reducing the movement of a cosmetic applicator caused by unintentional movements of a user.

BACKGROUND

Unintentional movements of the human body, or human tremors, can occur in individuals suffering from motion disorders or even healthy individuals. Due to these unintentional movements, a person may have difficulty in performing a task that requires care and precision, such as applying a cosmetic composition to a part of the body, such as the face, hands, or feet.

Therefore, there is a need for a solution that allows application of a cosmetic composition that is compatible with the diverse and disposable nature of cosmetic applicators.

SUMMARY

In an embodiment, a system is provided that stabilizes an applicator in response to the motion caused by a user, comprising: a mobile user device that is configured to execute an application; a motion stabilizer; and an adapter that holds a cosmetic applicator, wherein the motion stabilizer includes a receiver configured to be coupled with the adapter; at least one sensor configured to detect a movement caused by a user; circuitry configured to determine a compensation movement to offset the detected movement; and at least one motion generation device embedded in the receiver configured to control a motion of the cosmetic applicator according to the determined compensation movement, wherein the application is configured to capture an image of the user prior to a session of applying a cosmetic using the cosmetic applicator; capture an image of the user after the session of applying a cosmetic using the cosmetic applicator; detect an error in applying the cosmetic to a portion of the user's body; detect a deviation in the movement of the cosmetic applicator during the session when the error is detected; and adjust settings for the motion stabilizer to compensate for the deviation.

In an embodiment, the adapter includes a motion sensor that outputs data to the application indicating movement of the adapter during the session, and the application detect the deviation in the movement of the cosmetic applicator during the session based on the outputted data.

In an embodiment, the motion sensor is an accelerometer.

In an embodiment, the application displays a realtime mirror image of the user during the session, and detects a location of the cosmetic applicator and a location of a target portion of the user's body to which the cosmetic is to be applied.

In an embodiment, the application outputs realtime feedback to the user when deviation in the movement of the cosmetic application is occurring in realtime.

In an embodiment, the realtime feedback is a display of an indicator on the mobile user device to correct a position of the cosmetic applicator.

In an embodiment, the motion stabilizer further includes a vibrational element, and the realtime is an instruction to activate the vibrational element.

In an embodiment, the application is configured to display a target object that detects an initial deviation of movement by a user prior to the session, and to initially adjust settings for the motion stabilizer to compensate for the detected initial deviation.

In an embodiment, the application is configured to detect the error in applying the cosmetic to a portion of the user's body based on detecting that an application of the cosmetic crosses a visible boundary of a natural feature of the user.

In an embodiment, the application is configured to detect the error in applying the cosmetic to a portion of the user's body based on a machine learning model that is trained based on presenting images to a plurality of users and obtaining feedback from the users on a level of magnitude of error in applying make-up for those images.

In an embodiment, the application is configured to adjust settings for the motion stabilizer to compensate for the deviation based on a deep learning model that is trained based on receiving inputs of a user's image of an error applying a cosmetic during a session, data outputted from a motion sensor during the session, and compensation parameters used in a motion stabilizer that corrected the error in the make-up application process.

In an embodiment, a method is provided that is implemented by a system that stabilizes an applicator in response to the motion caused by a user, the system including a mobile user device that is configured to execute an application, a motion stabilizer, and an adapter that holds a cosmetic applicator, wherein the motion stabilizer includes a receiver configured to be coupled with the adapter; at least one sensor configured to detect a movement caused by a user; circuitry configured to determine a compensation movement to offset the detected movement; and at least one motion generation device embedded in the receiver configured to control a motion of the cosmetic applicator according to the determined compensation movement, the method comprising: by the application of the mobile user device, capturing an image of the user prior to a session of applying a cosmetic using the cosmetic applicator; capturing an image of the user after the session of applying a cosmetic using the cosmetic applicator; detecting an error in applying the cosmetic to a portion of the user's body; detecting a deviation in the movement of the cosmetic applicator during the session when the error is detected; and adjusting settings for the motion stabilizer to compensate for the deviation.

DETAILED DESCRIPTION

The present disclosure describes a cosmetic applicator system that minimizes unintentional movements by stabilizing, orienting, operating, controlling, etc. an applicator for a user and is also designed to be flexible to accommodate different types of commercially available cosmetic applications. The present disclosure further describes a system and features to enhance the functionality of such a cosmetic applicator system.

The basic features and operation of a motion stabilizing device for a cosmetic applicator is described in U.S. Pat. No. 11,458,062, which is incorporated herein by reference.

Figure 1:
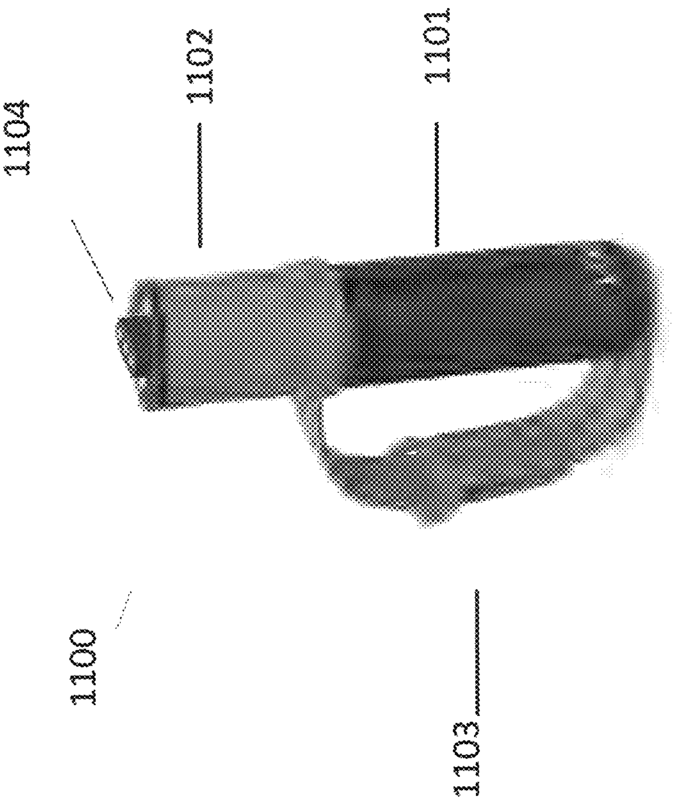
FIG. 1 shows a conventional motion stabilizing device.

FIG. 1 shows a conventional motion stabilizing device 1100, which serves as a base unit for receiving a cosmetic applicator according to an embodiment. The device 1100 includes a handle portion 1101, a receiver portion 1102 and a strap 1103. The receiver portion 1102 includes an interface 1104, shown as a male connector that couples with a cosmetic applicator, which will be discussed in detail below. The receiver portion could be utilized for communication between the base unit and the applicator. The connection to an adaptor and/or an applicator could be accomplished with a mechanical coupling, such as screw-in or snap-fit, or it could be accomplished with magnets.

Figure 2:
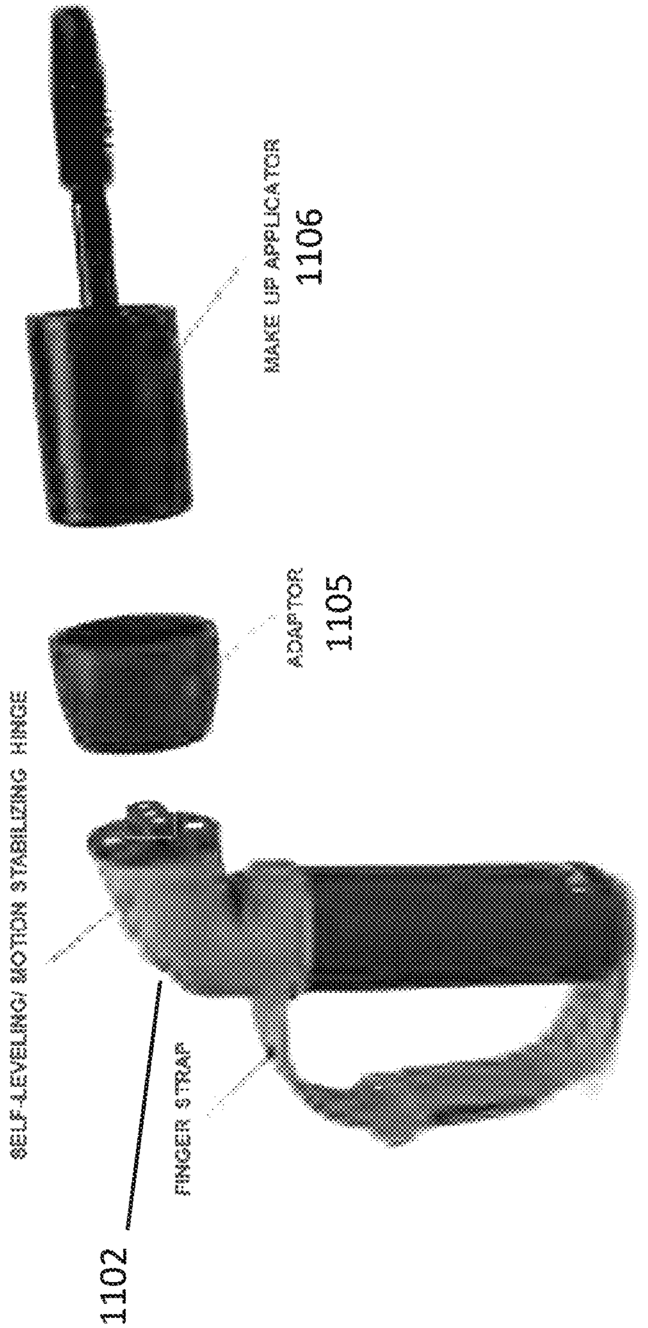
FIG. 2 shows how the conventional motion stabilizing device couples with an adaptor and a make-up applicator.

FIG. 2 shows how the device 1100 couples with an adaptor 1105 and a make-up applicator 1106. It can be seen that the adaptor fits over the exposed end of the receiver portion 1102. The adaptor includes electrical mating connectors (a female connector—not shown) in a recessed portion to make contact with the electric interface of the receiver portion 1101.

As shown in FIG. 2, the receiver portion 1102 is configured to contort, articulate, reposition, etc., between an upright posture (as shown in FIG. 1) and an angled posture (as shown in FIG. 2). This is accomplished with a hinge mechanism contained inside the receiver portion 1102. FIG. 2 shows that the hinge mechanism is a self-leveling/motion stabilizing hinge.

Figure 3A:
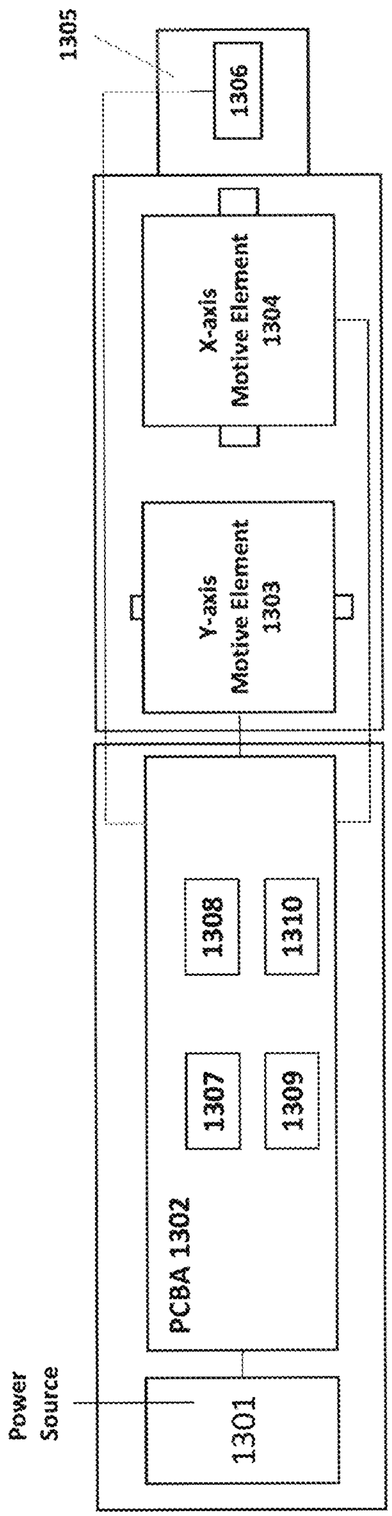
FIG. 3A shows a diagram of the internal components of a motion stabilizing device according to one embodiment.

FIG. 3A shows a diagram of the internal components of device 1100 according to one embodiment. In the handle portion, the device includes a power source 1301, which may be a battery or the like. The device includes a printed circuit board assembly (PCBA) 1302, which may include positional sensor circuitry 1307, reader circuitry 1308, control circuitry 1309, and communication interface 1310, as understood in the art.

For instance, as the sensor circuitry 1307, the PCBA may include at least one inertial sensor and at least one distributed motion sensor to detect unintentional muscle movements and measure signals related to these unintentional muscle movements that are created when a user adversely affects motion of the applicator. These sensors also detect the motion of the stabilized output relative to device. The control circuitry sends voltage commands in response to the signals to the motion generating elements (described below) to cancel the user's tremors or unintentional muscle movements. This cancellation maintains and stabilizes a position of the applicator, keeping it stable.

One of ordinary skill in the art readily recognizes that a system and method in accordance with the present invention may utilize various implementations of the control circuitry and the sensor circuitry and that would be within the spirit and scope of the present invention. In one embodiment, the control circuitry 1309 comprises an electrical system capable of producing an electrical response from sensor inputs such as a programmable microcontroller or a field-programmable gate array (FPGA). In one embodiment, the control circuitry comprises an 8-bit ATMEGA8A programmable microcontroller manufactured by Atmel due to its overall low-cost, low-power consumption and ability to be utilized in high-volume applications.

In one embodiment, the at least one inertial sensor in the sensor circuitry is a sensor including but not limited to an accelerometer, gyroscope, or combination of the two. In one embodiment, the at least one distributed motion sensor in the sensor circuitry is a contactless position sensor including but not limited to a hall-effect magnetic sensor.

The system created by the combination of the sensor circuitry, the control circuitry, and the motion generating elements may be a closed-loop control system that senses motion and acceleration at various points in the system and feeds detailed information into a control algorithm that moves the motion-generating elements appropriately to cancel the net effect of a user's unintentional muscle movements and thus stabilize the position of the applicator. The operation and details of the elements of the control system and control algorithm are understood in the art, as described in U.S. PG Publication 2014/0052275A1, incorporated herein by reference.

The communication interface 1310 may include a network controller such as BCM43342 Wi-Fi, Frequency Modulation, and Bluetooth combo chip from Broadcom, for interfacing with a network.

In the receiver portion of the device, there may be two motive elements to allow 3-dimensional movement of the receiver as anti-shaking movement. The two motive elements include a y-axis motive element 1303 and an x-axis motive element 1304, each being connected to and controlled by the PCBA 1302. Each of the motive elements may be servo motors as understood in the art. The device further includes end effector coupling 1305, which is configured to couple with the adaptor 1105. The end effector coupling 1305 may include a radiofrequency identification (RFID) reader 1306, configured to read an RFID tag, which may be included with the applicator, as will be discussed below.

Figure 3B:
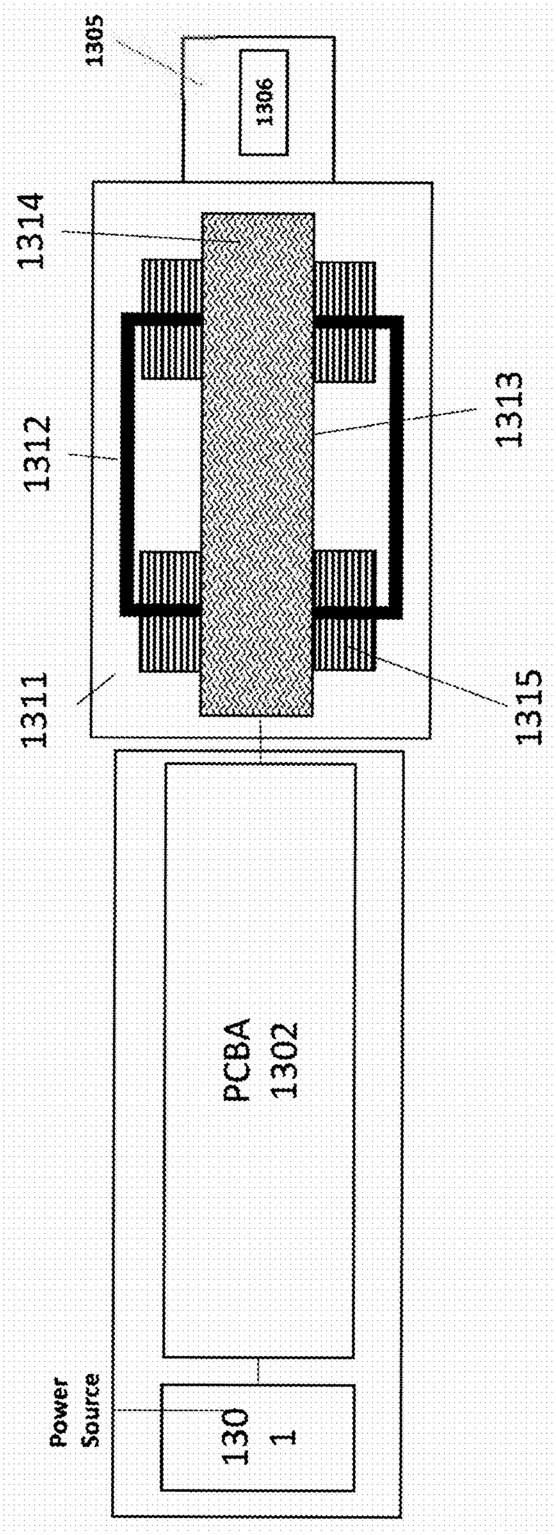
FIG. 3B shows a diagram of an alternative embodiment of the motion stabilizing device in which a receiver portion includes an electromagnetic positioner.

FIG. 3B shows a diagram of an alternative embodiment of the device 1100 in which the receiver portion includes an electromagnetic positioner 1311 instead of the motive elements shown in FIG. 3A. The electromagnetic positioner 1311 may include U-shaped magnetic cores 1312 arrayed around a non-magnetic tube 1313, which is filled with a magnetic fluid 1314. Each of the magnetic cores has arm portions that are surrounded by windings 1315. The magnetic cores may be controlled by the control circuitry in the PCBA 1302 to act as a controllable active magnetic field-generating structure which is used to generate a variable magnetic field that acts upon the magnetic fluid, causing it to be displaced, thereby enabling the armature to be moved to a desired coordinate position and/or orientation. The details of implementing the electromagnetic positioner 1311 may be found in U.S. Pat. No. 6,553,161, which is incorporated herein by reference.

In the above-described conventional motion stabilizing device, there is a problem that the interface 1104 that receives the adaptor 1105 requires a specific point of attachment to align properly with the interface.

Therefore, the below embodiments provide a universal adapter connection between the handle of the motion stabilizing device in order to improve user experience and reduce the struggle and time taken to set up the system for use.

In one embodiment, the present disclosure is directed towards a cosmetic applicator. The cosmetic applicator can be used for a variety of cosmetics and cosmetic applications, including, but not limited to, mascara, eyeliner, eyebrow products, lip products (lipstick, lip gloss, lip liner, etc.), skin products, and/or hair products. In one embodiment, the cosmetic applicator can include an adapter, wherein the adapter can connect the cosmetic applicator to a motion stabilizer. The motion stabilizer can be, for example, a handle that can counteract unintentional motions such as tremors or spasms. These motions can interfere with the application of cosmetics and can also make it difficult to generally interact with cosmetic applicators or tools. For example, the many cosmetic products require a twisting motion or force to be applied to open or extrude the product. It can be difficult for users to achieve the range of motion or the precision necessary to apply these forces to the cosmetic. In one embodiment, the cosmetic applicator can hold a cosmetic and can enable the proper force to be applied to the cosmetic to open, close, mix, stir, blend, extrude, or achieve other similar functions necessary for application.

Figure 4:
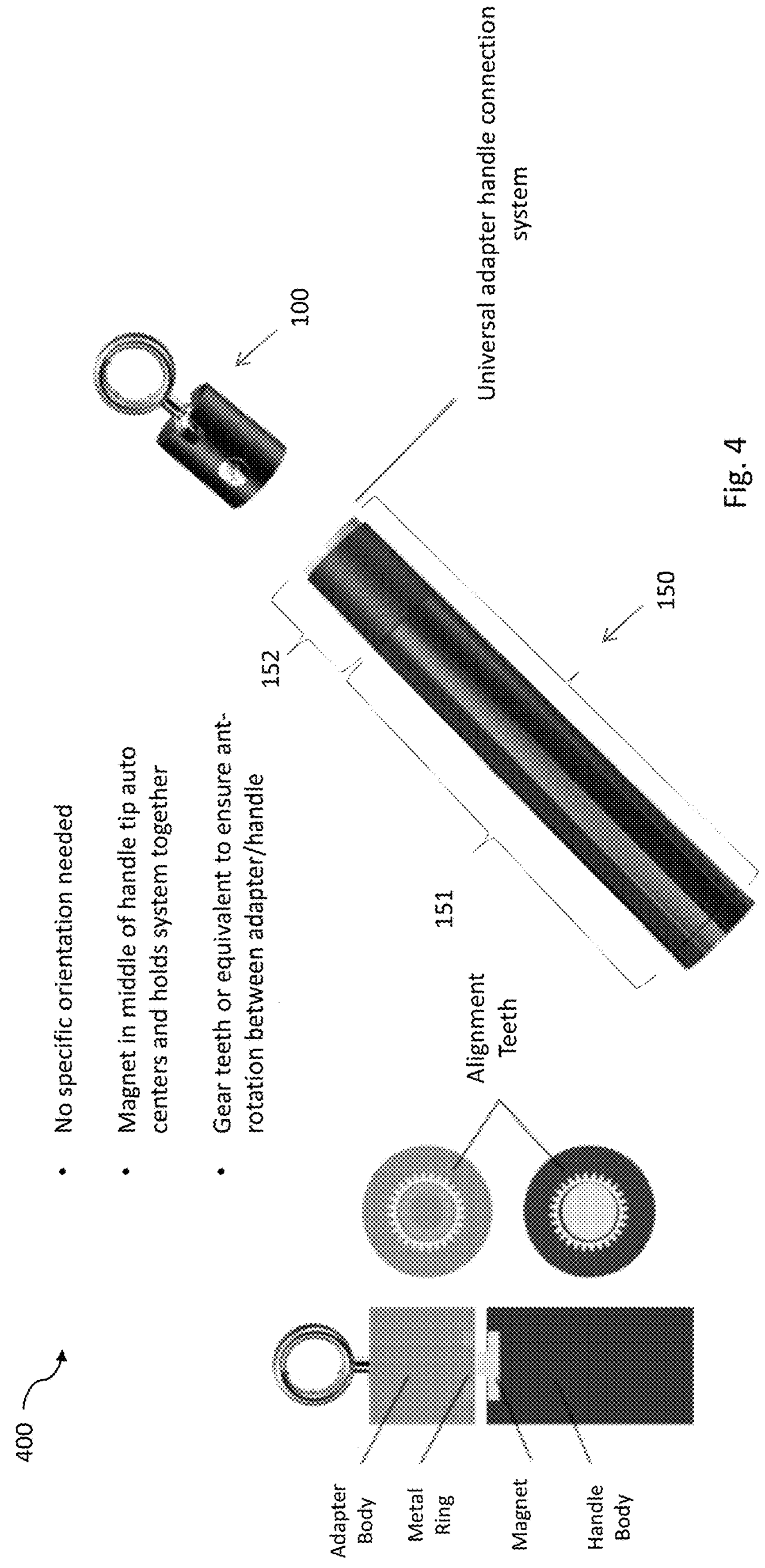
FIG. 4 shows an overview of a universal adapter handle connection system.

FIG. 4 shows an overview of a universal adapter handle connection system 400. The system includes a motion stabilizer device 150 that includes a handle portion 151 and a hinge portion 152 (receiver portion) that is functionally similar to the device 1100 shown in FIG. 1. It further includes a universal adapter 100 that attaches to the device 150 and also holds different types of cosmetic applicators.

Figure 5B:
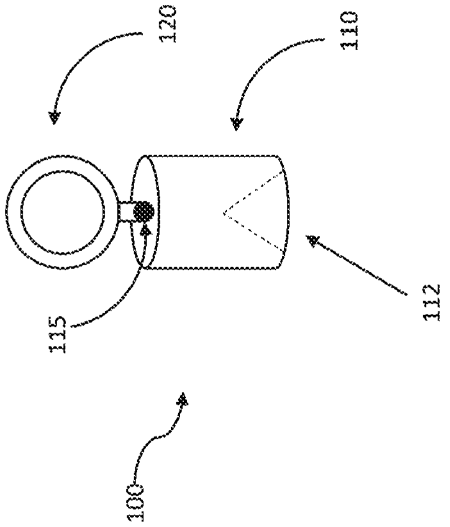
FIG. 5B is a transparent side view of the adapter, according to one embodiment.
Figure 5A:
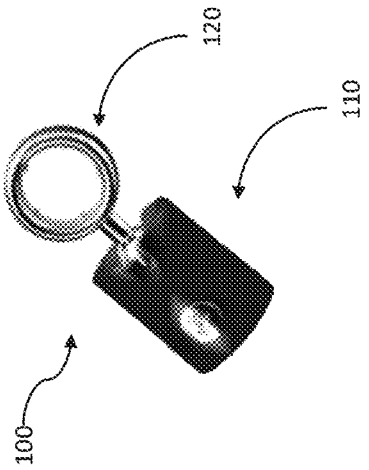
FIG. 5A shows an illustration of an adapter, according to one embodiment.

FIG. 5A shows an illustration of adapter 100, according to one embodiment of the present disclosure. The adapter 100 can include an adapter body 110, wherein the adapter body 110 can be connected to the motion stabilizer 150. The adapter body 110 can be connected to or can form the base or body of a cosmetic holder 120. Each of these components will be discussed in further detail herein. Various configurations of the adapter 100 can be used for different cosmetics and tools. For example, the shape and dimensions of the cosmetic holder 120 can be configured for different cosmetic products. The adapter 100 can be easily attached to and removed from the motion stabilizer, as will be discussed herein. In one embodiment, the adapter 100 can broaden the range of motion of a cosmetic applicator to enable movements that are necessary for cosmetic application. In some embodiments, the adapter 100 can be attached to a stand or carriage for further actions to be performed with a cosmetic held by the cosmetic applicator.

FIG. 5B is a transparent side view of the adapter 100, according to one embodiment of the present disclosure. The adapter body 110 can be shaped approximately as a right cylinder. A first end of the adapter can be attached to one end of a motion stabilizer. The motion stabilizer can be a cylindrical rod forming a handle for a user to grasp. The first end can also be referred to hereinafter as a bottom end or a base of the adapter. The bottom end of the adapter body 110 can include at least one magnet, wherein the at least one magnet can be attracted to and attach to a magnet in the motion stabilizer. The bottom end of the adapter body 110 can include additional physical structures that can align, guide, and fix the adapter to the motion stabilizer. In one embodiment, the bottom end of the adapter body 110 can form a chamber 112, as illustrated in the transparent view of FIG. 5B. The chamber can be a hollow area within the body of the adapter 110 that is fully contained by the walls of the adapter 110. The chamber 112 can be approximately conical in shape. In one embodiment, the cutout can be cylindrical. The chamber 112 can be configured to fit over a projection on one end of the motion stabilizer. The chamber 112 can be used to align and guide the attachment of the cosmetic applicator to the motion stabilizer. The fit of the chamber 112 over and around the projection on the end of the motion stabilizer limits lateral motion that would misalign the cosmetic applicator and the motion stabilizer. It can be easier for a user to align the chamber 112 over the end of the motion stabilizer than it would be for the user to align the edges of the circular face of the adapter with the edges of the circular face of the motion stabilizer. The chamber 112 can have rotational symmetry such that the cutout can be placed over the end of the motion stabilizer in any orientation or at any degree of rotation around the axis of the chamber 112. In one end, a magnet can be fixed at the tip of the chamber, inside the body of the adapter. The magnet at the tip of the cutout can be attached to a magnet at the tip of the projection on the end of the motion stabilizer.

The cosmetic holder 120 can be located at a second end of the cosmetic applicator. In one embodiment, the cosmetic holder 120 can be a ring, wherein a cosmetic tool or product can be inserted into the ring. Many cosmetic tools, such as mascara wands, lipstick applicators, concealer applicators, and cosmetic pencils, are approximately cylindrical. In one embodiment, the ring can secure the cosmetic tools at the widest part of the tool. A ring-shaped holder can also hold cosmetic tools of varying shapes, such as cuboids. In one embodiment, the cosmetic holder 120 can include one or more projections along the inner wall of the holder and extending outward into the center of the holder. Contact and friction between the one or more projections and an inserted cosmetic tool can result in a more secure grip or hold of the cosmetic holder around the inserted cosmetic tool. In some embodiments, the inner wall of the cosmetic holder 120 can be lined with a material that can improve the grip or hold of the cosmetic holder around the inserted cosmetic tool. The improved grip can be a result of a material property, such as a coefficient of friction or a material deformation. For example, the inner wall can be lined with rubber or silicon. In one embodiment, the lining material can be a textured material with grooves, ridges, bumps, or similar features that prevent movement or slippage of the cosmetic tool once it is inserted into the cosmetic holder 120.

Various cosmetic holder configurations are compatible with the cosmetic applicator 100. In one implementation, the holder can be an open ring or a C-shaped holder. In one embodiment, the holder can be a loop, wherein the ends of the loop can overlap. In one embodiment, the holder can be one or more coiled loops. In one embodiment, the cosmetic holder 120 can be a tube or sheath forming a chamber inside the tube, wherein a cosmetic tool or product can be inserted into the chamber. In one embodiment, the tube can be closed on one end to contain a cosmetic tool or product in the chamber. In one example, the tube can be approximately cylindrical. In one example, the sheath can be a partial cylinder, such as a half-cylinder that does not wrap fully around the inserted cosmetic. In one embodiment, the size of the cosmetic holder 120 can be modified. For example, the cosmetic holder 120 can be a round holder, wherein the diameter of the holder can be modified to accommodate different cosmetic tools. A pushing force on a point along the outside of the holder can compress the holder to that of a smaller diameter. A pulling force on a point along the inside of the holder can expand the holder to that of a larger diameter. In one embodiment, the force can be applied at a single point along the holder to enable one-handed modification of the holder diameter. In one implementation, a user can be provided with a number of cosmetic holders, wherein each cosmetic holder has different dimensions or shapes for different cosmetic tools or products. A cosmetic holder 120 can be removed from the adapter body 110 and replaced with another of suitable configuration.

In one embodiment, the cosmetic holder 120 can be attached to the adapter body 110 with a joint 115, such as a ball joint. The ball joint can enable movement of the cosmetic holder 120 relative to the adapter body 110. For example, the cosmetic holder 120 can be rotated in place or can pivot to form an angle with the adapter body 110. The joint can be configured for continuous motion of the cosmetic holder 120 or for discrete steps of movement. According to some embodiments, the motion of the cosmetic holder 120 can be constrained. For example, the adapter 110 can form a walled channel, wherein the joint is disposed inside the walled channel. The walls of the channel can constrain movements of the joint and/or the cosmetic holder 120. In one embodiment, the joint 115 can be a motorized component. The cosmetic holder 120 can move as a result of the motorized component without requiring external force from a user.

Figure 5D:
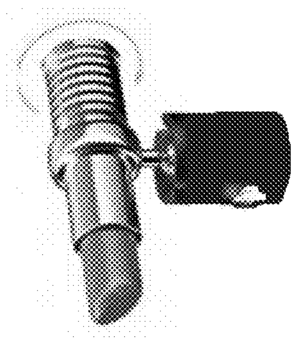
FIG. 5D shows how the adaptor holds a specific cosmetic applicator, according to an embodiment.
Figure 5C:
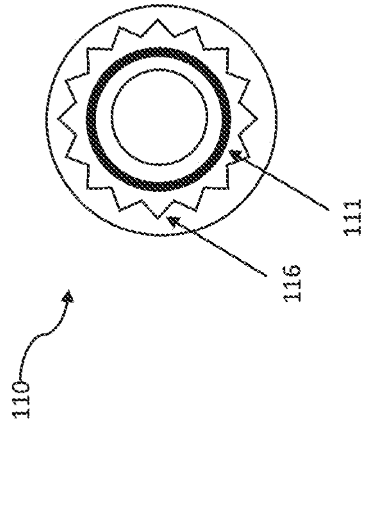
FIG. 5C is a view of the bottom face of the adapter body, according to one embodiment.

FIG. 5C is a view of the bottom face of the adapter body 110, according to one embodiment of the present disclosure. The bottom face of the adapter body 110 can be approximately a circle given that the adapter is a right cylinder. A magnet 111 can be disposed on the bottom face of the adapter. In one embodiment, the magnet 111 can be a uniformly ring-shaped magnet, as illustrated in FIG. 5C. For example, the magnet 111 can have the shape of a washer. The ring-shaped magnet 111 can be attracted to and attach to a magnet disposed along the circumference of one end of the motion stabilizer. In some embodiments, the adapter body 110 can be attached to the motion stabilizer in any orientation because of the ring-shaped magnet 111. The adapter body 110 can be attached to the motion stabilizer with any rotation of the adapter 100 around the central axis of the adapter. In one embodiment, the adapter 100 can be a universal adapter and can attach a magnetic end of the motion stabilizer in any orientation regardless of the positioning and/or polarity of magnets at the end of the motion stabilizer. Any portion of the ring-shaped magnet 111 at the base of the adapter can contact the magnets on the motion stabilizer to attach the adapter to the motion stabilizer.

The ring-shaped magnet 111 of the present disclosure presents an advantage over traditional adapters for motion stabilizer. For example, certain motion stabilizers can include two magnets located diametrically opposite to each other on a circular face of the motion stabilizer. Most traditional adapters include two magnets at the base for attachment to a motion stabilizer. The adapter can only be attached to the motion stabilizer if the two magnets on the motion stabilizer align with the two magnets in the same position on the adapter. In some implementations, the polarity of the magnets on the motion stabilizer can also differ such that each magnet on the motion stabilizer will only be attracted to one of the two magnets on the adapter. The limitations on the orientation of the traditional adapter can pose issues for users attempting to attach the adapter to the motion stabilizer. For example, users may lack the precision of movement needed to align the magnets as needed for attachment. In addition, the limitations on the orientation of the traditional adapter means that the orientation of the tool or instrument that is held by the applicator is also limited. When applying cosmetic products to or near the face, it can be desired that the applicator can be fixed at various angles and orientations or that the orientation of the applicator can be adjusted. For example, certain mascara wands are curved. The mascara wand should contact the eyelashes such that the curvature of the wand conforms to the curvature of the eye. It can be very difficult to achieve this position if the adapter holding the mascara wand can only be attached to the motion stabilizer in one orientation, as with traditional adapters with a limited number of magnets in set positions. In contrast, an adapter with a ring-shaped magnet, as in FIG. 5C, can be attached to the motion stabilizer in any orientation. The adapter can be rotated until the mascara wand, or any other cosmetic tool, is in a desired orientation for application and then attached to the motion stabilizer with contact between the ring-shaped magnet and any magnets disposed on the face of the motion stabilizer. The motion stabilizer can be maneuvered in various positions while the attached applicator and cosmetic also move. For example, the orientation of the attached applicator and the cosmetic can change as the user applies the cosmetic. The attachment of the applicator to the motion stabilizer without orientation expands the range of movement of the attached cosmetic.

In one embodiment, the adapter body 110 can include a ring of gears, teeth, or similar alignment structures 116. The alignment structures 116 can be located at the base of the adapter and can be concentric with the ring-shaped magnet 111. In one embodiment, the alignment structures can be located along the inner wall of the cutout at the bottom end of the adapter. In some embodiments, the alignment structures 116 can fit into or interlock with corresponding alignment structures on the motion stabilizer when the adapter is attached to the motion stabilizer. The alignment structures 116 can limit the rotation of the cosmetic applicator once the adapter has been attached to the motion stabilizer. Certain motion stabilizers can rotate in order to counteract any rotational force applied to the motion stabilizer so that an attachment to the motion stabilizer (such as the cosmetic applicator) remains steady. The "anti-rotation" mechanism can be useful for users who experience sudden, involuntary movements while holding the motion stabilizer. In one embodiment, the alignment structures 116 can be a ring of raised nubs or teeth-like structures that can fit into corresponding grooves or receptacles at the end of the motion stabilizer that is attached to the base of the adapter. In one embodiment, the alignment structures 116 can be a ring of recessed structures or a combination of raised and recessed structures that can fit into corresponding raised and/or recessed structures at the end of the motion stabilizer. The fitting of the alignment structures 116 into complementary structures at the end of the motion stabilizer can fix the cosmetic applicator in place when the adapter has been attached to the motion stabilizer. Any rotation of the motion stabilizer in order to counteract involuntary user movement will thus be carried through to the cosmetic applicator to maintain the orientation of the cosmetic applicator once the cosmetic applicator is attached to the motion stabilizer.

The alignment structures 116 can provide a range of discrete orientations at which the adapter can be attached to the motion stabilizer. For example, the adapter can only be attached to the motion stabilizer when each of the alignment structures 116 of FIG. 5C is aligned with a corresponding recessed structure in the motion stabilizer. If the alignment structures 116 are not aligned with and sitting in the recessed structures, the adapter will not be properly attached to the motion stabilizer. However, the symmetry of the repeated alignment structures 116 can still enable the attachment of the adapter at a number of rotations (e.g., 10+ rotational options) for easy attachment.

FIG. 5D shows how the adaptor 100 holds a specific cosmetic applicator, such as a lipstick applicator within the cosmetic holder 120. While a lipstick applicator is shown, the cosmetic holder can hold numerous examples of applicators, such as mascara applicators and nail polish applicators as other examples. In contrast to the adapter 1105 of FIG. 1, it can be seen that the cosmetic holder 120 holds the applicator at perpendicular angle to the handle of the motion stabilizer 150. This provides a more relaxed and ergonomic hand position for the user when using the cosmetic applicator.

Figure 6A:
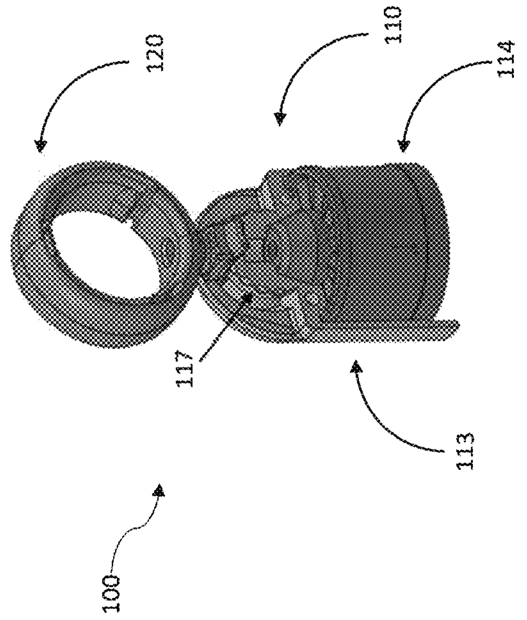
FIG. 6A is an illustration of the adaptor 100 with a cutaway view of the adaptor body 110, according to one embodiment.

FIG. 6A is an illustration of the adaptor 100 with a cutaway view of the adaptor body 110, according to one embodiment of the present disclosure. In one embodiment, the adaptor body 110 can include an outer shell 113, wherein the outer shell 113 encloses an inner body 114. The inner body 114 can be attached to a motion stabilizer via the magnetic attachment described herein with reference to FIG. 5C. In one embodiment, the cosmetic holder 120 can be attached to the outer shell 113. The attachment of the cosmetic holder 120 to the outer shell 113 can enable movement of the cosmetic holder 120 that is independent of the movement of the inner body or the motion stabilizer. The attachment of the cosmetic holder 120 to the outer shell 113 can be enclosed within the adaptor body 110. In one embodiment, the cosmetic holder 120 can be attached to the outer shell 113 along a series of detents in the outer shell. The detents can be, for example, a series of indentations, grooves, teeth, or the like, such as the indented structures 117 of FIG. 6A. The position of the cosmetic holder 120 can change by moving the cosmetic holder 120 linearly along the series of detents, such that the cosmetic holder 120 can be fixed in place at each of the detent structures 117. In one embodiment, the base of the cosmetic holder 120 can include a projection that fits into each of the detent structures 117. The projection can snap into place when positioned at or against each of the detent structures 117 to temporarily lock the cosmetic holder 120 into an angled position within a single plane. The plane of the face (opening) of the cosmetic holder 120 can stay the same while the angular position of the cosmetic holder 120 can be adjusted. A force can be applied by a user to position the cosmetic holder 120 at any of the detent structures 117. The cosmetic holder 120 can thus be angled relative to the central axis of the adaptor body 110 and the attached motion stabilizer. In one embodiment, the cosmetic holder 120 can be attached to the adaptor body 110 with a 2-axis adapter. The angle of the cosmetic holder 120 can be adjusted as described with reference to the detent structures 117. Additionally or alternatively, the plane of the opening of the cosmetic holder 120 can also be adjusted by a rotation of the cosmetic holder 120 for 2-axis movement. For example, the cosmetic holder 120 can rotate axially at or near the point of attachment to the adaptor body 110. In one embodiment, the rotation of the cosmetic holder 120 can be modulated with detents or similar structures to provide a number of fixed rotational positions of the cosmetic holder 120. For example, the cosmetic holder 120 or the adaptor body 110 can include an internal gear or ratcheting structure, wherein the cosmetic holder 120 can be rotated a number of degrees to engage the teeth of the internal gear. The cosmetic holder 120 can be temporarily locked in a rotational position when the teeth are engaged.

Figure 6B:
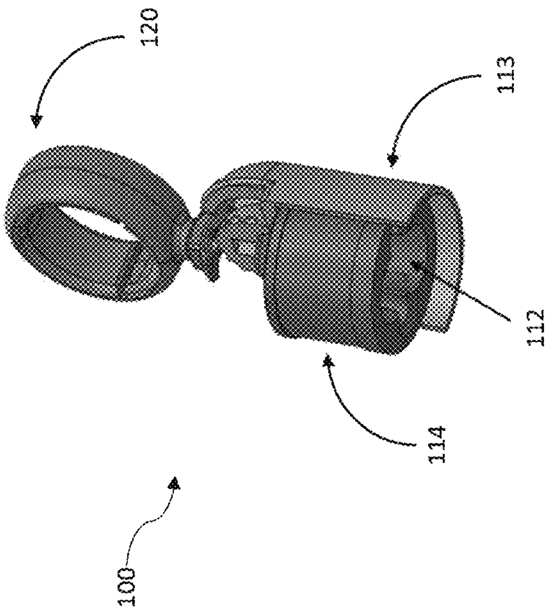
FIG. 6B is a side view of the adaptor with a cutaway view of the adaptor body, according to one embodiment.

FIG. 6B is a side view of the adaptor 100 with a cutaway view of the adaptor body 110, according to one embodiment of the present disclosure. The inner body 114 of the adaptor body 110 can form the chamber 112, as has been described herein. Various shapes and dimensions of the chamber 112 are compatible with the present adaptor 100. In one embodiment, the outer shell 113 can extend past the end of the inner body 114. The outer shell 113 can surround the attachment point of the adaptor 100 to a motion stabilizer or other compatible structure and can prevent the adaptor 100 from being displaced from the attached structure. In some embodiments, the magnetic ring can be formed at the base of the inner body 114.

Figure 6D:
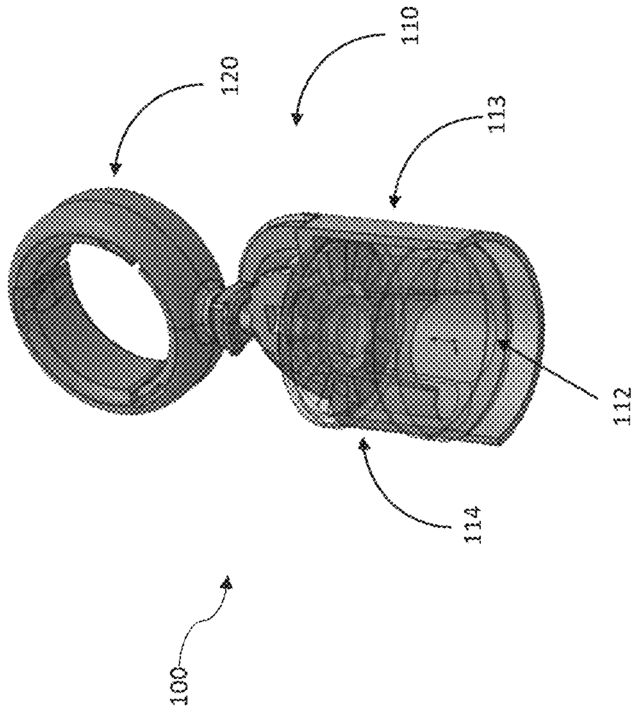
FIG. 6D is a transparent view of the inner body of the adaptor, according to one embodiment.
Figure 6C:
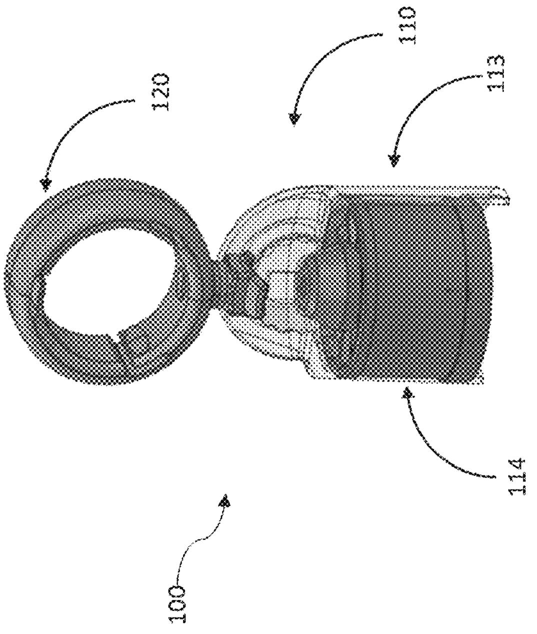
FIG. 6C is a transparent view of the outer shell of the adaptor, according to one embodiment.

FIG. 6C is a transparent view of the outer shell 113 of the adaptor 100, according to one embodiment of the present disclosure. The outer shell 113 can form a cavity surrounding the inner body 114. In one embodiment, the inner body 114 can rotate relative to the outer shell 113 while the outer shell 113 and/or the cosmetic holder 120 are fixed in place and do not rotate. For example, the inner body 114 can rotate in order to counteract an unintentional rotational movement of the motion stabilizer or the adaptor 100. The rotation of the inner body 114 is not translated to the cosmetic holder 120 because the cosmetic holder 120 is not in contact with the inner body 114. Similarly, the fitting of the outer shell 113 around the inner body 114 can include a gap between the outer shell 113 and the walls of the inner body 114 so that the rotation of the inner body 114 is not translated to the outer shell 113.

FIG. 6D is a transparent view of the inner body 114 of the adaptor 100, according to one embodiment of the present disclosure. The inner shell 114 can form the chamber 112, as has been described herein. The chamber 112 can extend to the top of the inner body. In one embodiment, the chamber 112 can be shaped as a central cylinder with two cylinders adjacent to the central cylinder, as illustrated in FIG. 6D. The shape of the chamber 112 and the symmetry of the chamber 112 can depend on the intended attachment to a motion stabilizer or other structure. In one embodiment, the shape of the chamber 112 can depend on the desired movement of the adaptor 100. For example, an infinitely symmetrical chamber can be attached onto a motion stabilizer in any orientation and can remain stationary when the motion stabilizer rotates. In another example, a chamber with limited axes of symmetry can result in a fixed number of orientations at which the adaptor can be attached to the motion stabilizer.

In one embodiment, the attachment of the cosmetic applicator to the motion stabilizer can activate at least one sensor to indicate that the adapter body 110 has been successfully attached to the motion stabilizer. The at least one sensor can be, for example, a Hall effect sensor that can detect and respond to the magnetic field produced by the adapter and/or the motion stabilizer. In one embodiment, the at least one sensor can be a pressure-activated sensor. Alternative sensors known to those of ordinary skill in the art can be compatible with the systems and apparatuses disclosed herein. In one embodiment, the at least one sensor can detect when the cosmetic applicator has not been attached to the motion stabilizer properly. For example, a Hall effect sensor can detect a partial magnetic field from the adapter with a magnitude that is less than an expected magnitude. The partial magnetic field can indicate that a portion of the ring-shaped magnet on the adapter is physically shielded or has failed to produce a magnetic field. In one embodiment, the data from the at least one sensor can be used to notify a user to inspect the cosmetic applicator or reattach the cosmetic applicator.

In one embodiment, the adapter 100 can include one or more sensors and/or an integrated circuit. The one or more sensors can include, but are not limited to, pressure sensors, light sensors, weight sensors, tension or force sensors, a Hall sensor, an accelerometer, a gyroscope, or the like. Data from the one or more sensors can be used to identify when a cosmetic has been inserted into or attached to the cosmetic applicator. In one embodiment, the data from the one or more sensors can be used to identify physical features of an attached cosmetic, such as a size, a shape, or a weight of the attached cosmetic. In one embodiment, the data from the one or more sensors can relate to a motion of the cosmetic applicator 100 or a motion of an attached component, such as the attached cosmetic or the motion stabilizer. In one embodiment, the data from the one or more sensors can be transmitted from the cosmetic applicator to a remote device, such as a server or a user device. In one embodiment, the cosmetic applicator can receive data, including instructions, from the same remote device or a second remote device. Further detail surrounding network In an embodiment, the system described above includes the functionality to auto-detect adapters to activate specific protocols to the motion stabilizer device 150. For instance, the motion stabilizer device 150 may perform auto detection of different adapters that are used for different cosmetics such as lipstick, mascara, etc. As soon as the adapter is connected to the handle of the motion stabilizer device 150, the handle will automatically recognize which style of adapter (for example, lipstick vs mascara) is attached and will load a specific set of protocols developed for that specific application.

Figure 7:
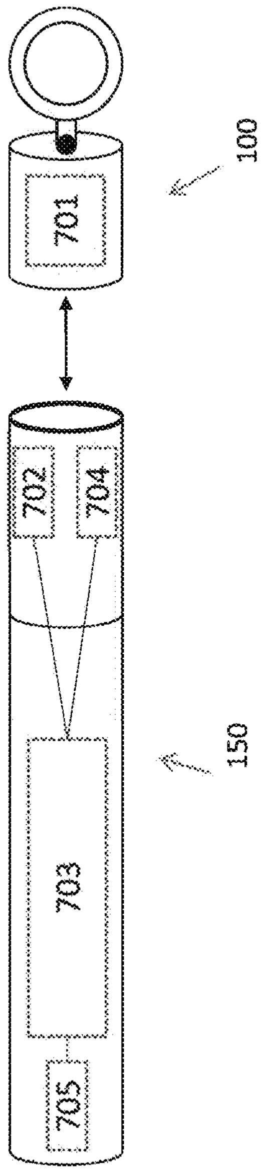
FIG. 7 shows a block diagram of the communicative hardware elements in the stabilizer device and the adapter, according to an embodiment.

FIG. 7 shows a block diagram of the communicative hardware elements in the stabilizer device 150 and the adapter. The adapter includes a communication interface 701 and the receiver portion of the stabilizer device includes a communication interface 702. The communication interfaces, in one example, is a near field communication (NFC) interface (where element 702 is a radiofrequency identification (RFID) reader configured to read an RFID tag 701). Furthermore, the receiver portion of the stabilizer device includes the hall effect sensor 704 described above. Thus, the RFID reader may be activated in response to the hall effect sensor 704 detecting insertion of the adapter 100. Alternatively, each of interfaces 701 and 702 operate as Bluetooth interfaces in another example, such as Bluetooth Low Energy (BLE) type interfaces.

The interface 702 in the receiver portion is connected to PCBA 703 that is coupled to or includes a memory 705 that stores different protocol information.

Once device 150 recognizes the adapter 100 that is present, it will receive information on the type of specific adapter it is based on information stored on the communication interface 701. The communication interface 702 then communicates the information to the PCBA 703, which stores specific protocols in the device software that target specific gestures and movements for the specific adapter connected (i.e. if lipstick adapter is attached, device will call on lipstick gesture protocols)

Figure 8:
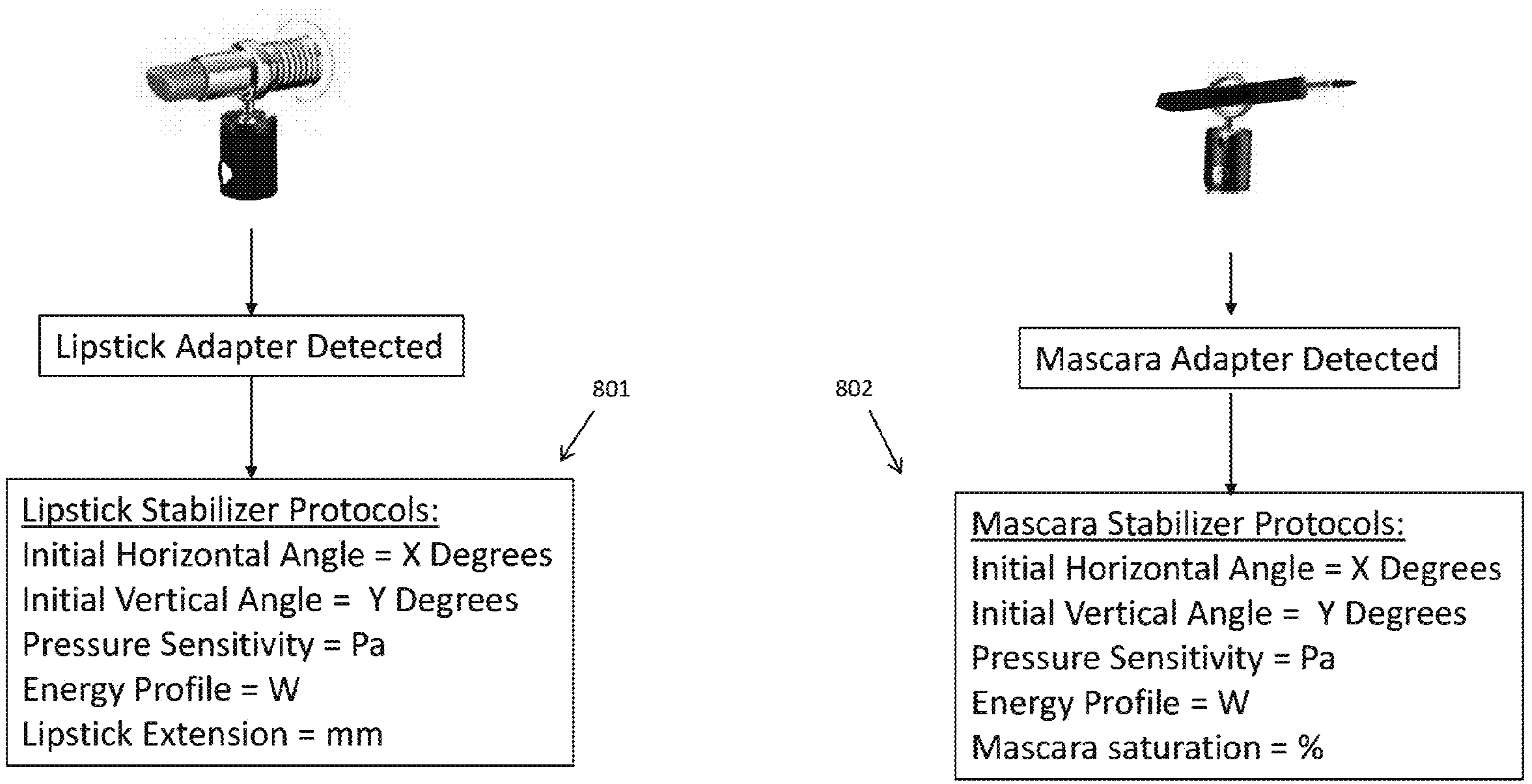
FIG. 8 shows different protocols for when the adapter has different cosmetic applicators, according to an embodiment.

For instance, as shown in FIG. 8, a first set of protocols 801 for a lipstick may include specific parameters initial angles of orientation of the stabilizer along with settings for pressure sensitivity, energy consumption, and initial lipstick extension. While a different second set of protocols 802 for a mascara may include different specific parameters initial angles of orientation of the stabilizer along with settings for pressure sensitivity, energy consumption, and mascara saturation.

There could be multiple adjustments to each protocol depending on the adapter and applicator. For example, with lipstick it is desired to remove the axial rotation of the adapter with respect to the handle since this can at times cause unwanted or unexpected movements for the user. It is also desired to limit the amount of flexion, and to create an initial "home position" as the hand holding position may be different for lipstick vs mascara. Additionally, it is desired to change the speed at which the motors move for mascara to be a bit slower so that there is less risk of unintended movements within close vicinity of the eyes. An example for additional lipstick protocol features are as follows.

Disable axial rotation of adapter relative to handle

Set motor speed to 100% for quickest possible adjustments

Flex adapter to initial "home" angular setting for best application orientation

Figure 9:
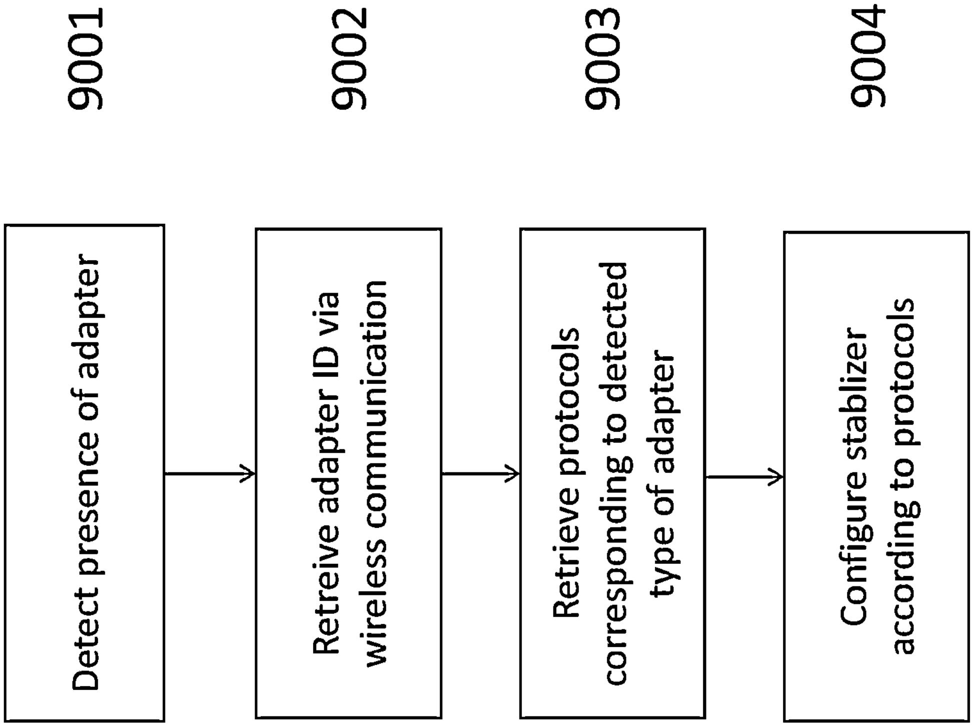
FIG. 9 shows a flowchart for performing the auto-detection.

FIG. 9 shows a flowchart for performing the auto-detection as discussed above. The steps are performed at the motion stabilizer device 150. In step 9001, the communication interface 702 detects the presence of the adapter 100. For instance, when the communication interface 702 is an RFID reader and the communication interface 701 is an RFID tag, these elements may perform an initial handshake before establishing a communication channel, as is understood in the art.

In step 9002, after a communication channel is established between the communication interfaces 701 and 702, the communication interface 701 transmits identification information to the communication interface 702. The identification information indicates the type of adapter as discussed above.

In step 9003, the communication interface 702 transmits the received identification information to the PCBA 703 that is onboard the stabilizer device, and the PCBA 703 retrieves the protocols stores on a local memory that correspond to the identified type of adapter.

In step 9003, the PCBA 703 controls configuration of the motion stabilizer device according to the stored protocols after it is detected that the adapter is attached to the motion stabilizer device.

With the above procedures, not only will the motion stabilizer device recognize an adapter is present, but it will recognize whether it is a specific adapter used for lipstick, mascara, or others. Once device recognizes the adapter that is present, it will call on specific protocols in the device software that target specific gestures and movements for the specific adapter connected (i.e. if lipstick adapter is attached, device will call on lipstick gesture protocols)

Figure 10:
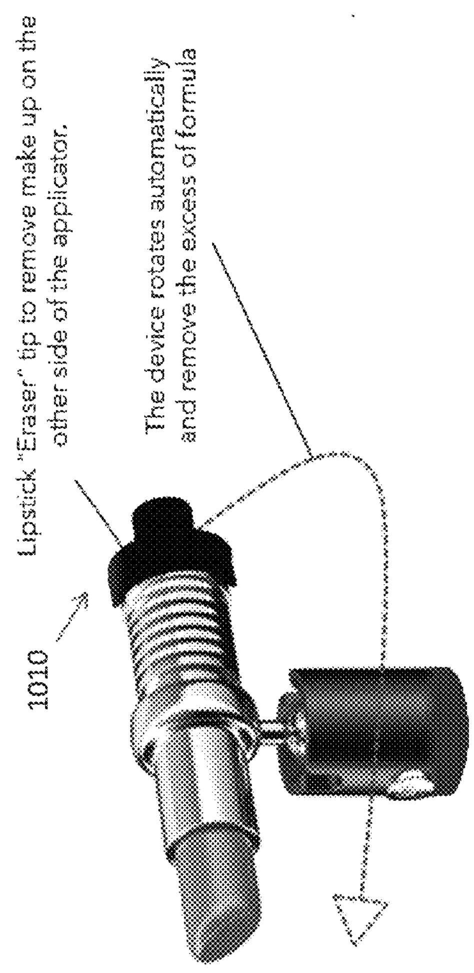
FIG. 10 illustrates an automated reversal or swivel feature of the adapter to provide an eraser feature to face a user, according to an embodiment.

In an embodiment, as shown in FIG. 10, the system described above includes automated reversal or swivel of the adapter orientation post application to provide an "eraser" feature 1010 to clean up any mistakes made by the user.

Figure 11B:
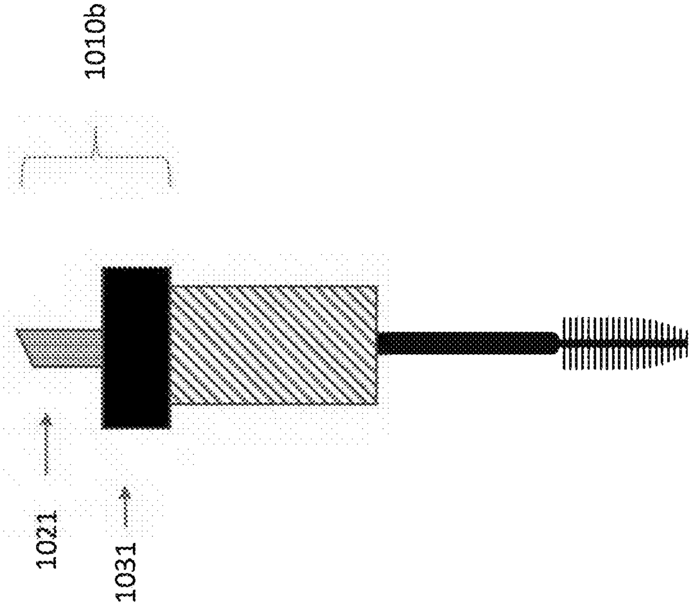
FIGS. 11A-11B illustrated that the eraser itself may have different shapes, diameters, and materials to be specifically designed for different cosmetic applicators, according to an embodiment.
Figure 11A:
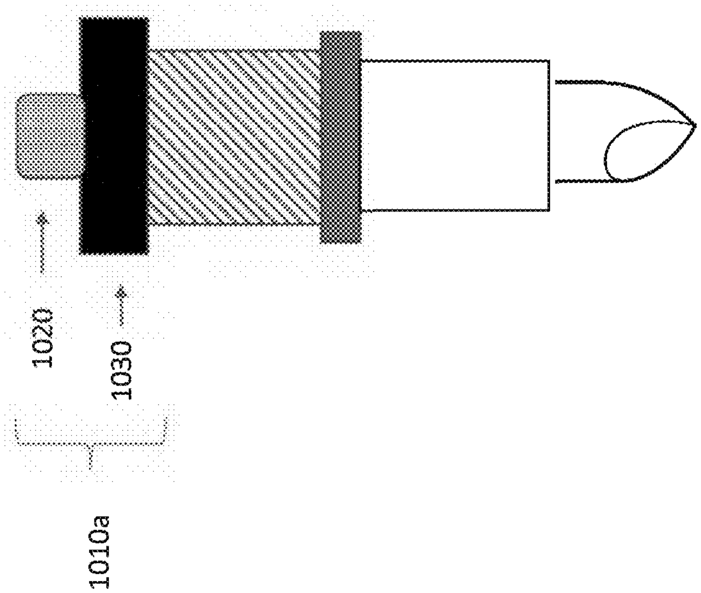

As shown in FIG. 11A, the eraser itself may have different shapes, diameters, and materials to be specifically designed for different cosmetic applicators. In the example of FIG. 11A, for a lipstick tube, an eraser base 1030 may have a wider diameter to accommodate the diameter of the lipstick base itself, and the eraser tip 1020 may have a first cuboid shape for handling larger smudges. Alternatively, in the example of FIG. 11B, for a mascara wand, an eraser base 1031 may have a relatively smaller diameter to accommodate the diameter of the mascara wand handle, and the eraser tip 102 may have a more narrow chisel end for handling precise erasing operations.

Figure 12A:
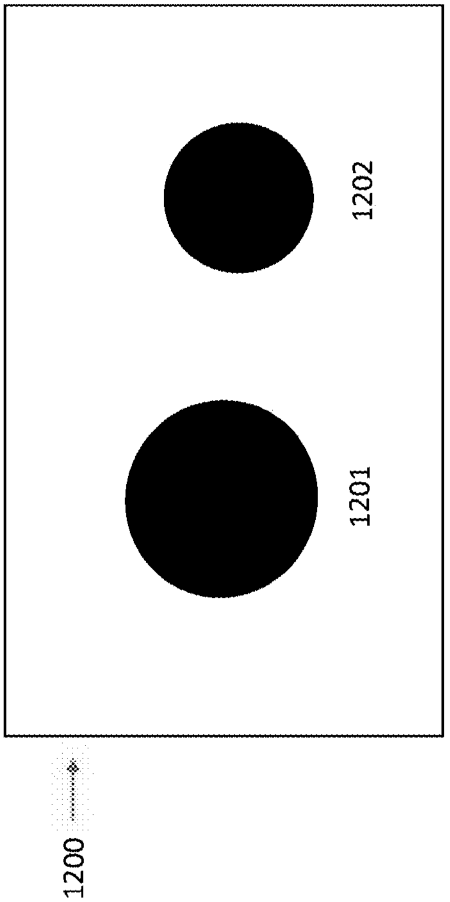
FIG. 12A shows a tray that is used to hold the different erasers prior to insertion onto the cosmetic applicator, according to an embodiment.

In an embodiment, FIG. 12A shows a tray 1200 that is used to hold the different erasers 1010 prior to insertion onto the cosmetic applicator. The tray 1200 includes a plurality of slots 1201 and 1202 for holding the different types of erasers described above.

Figure 12B:
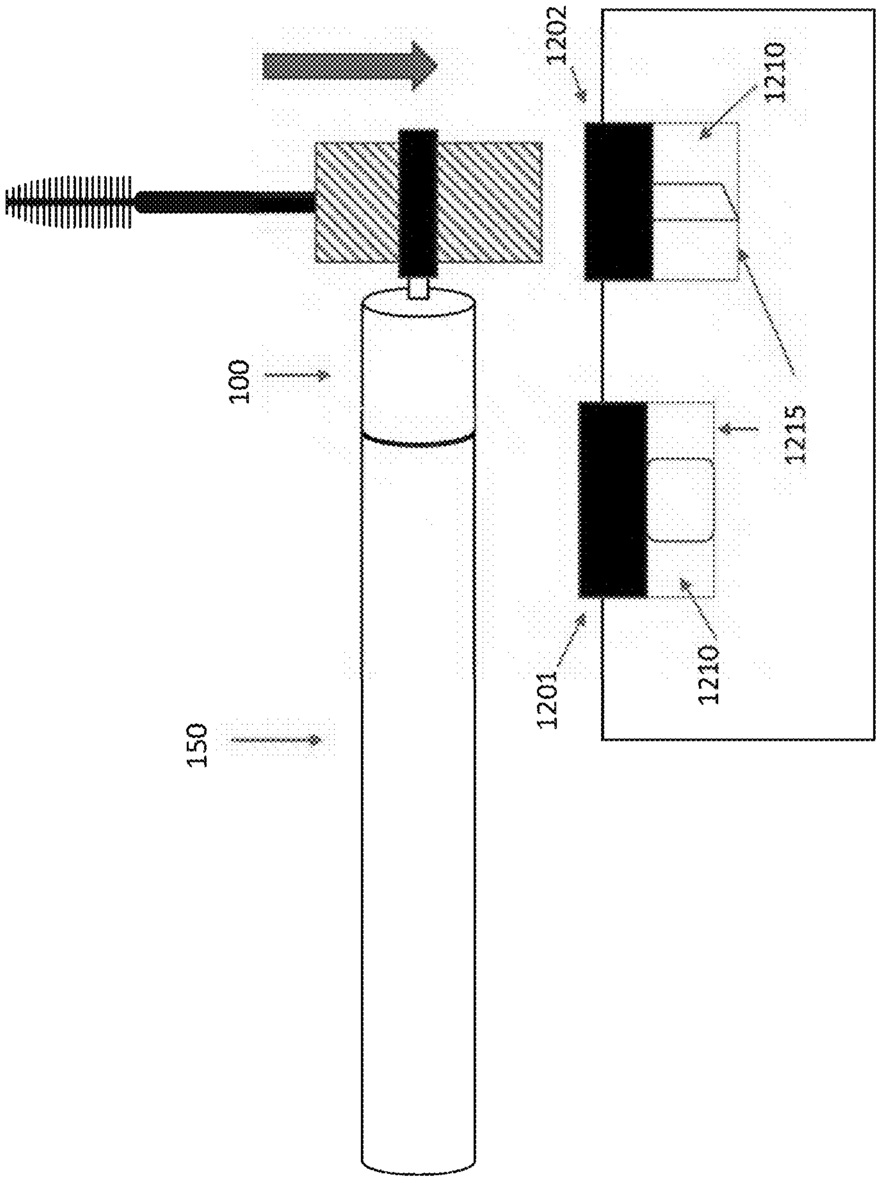
FIG. 12B shows how the motion stabilizing device with the adapter attached thereto can be moved in a downward motion to receive the eraser in an embodiment.

FIG. 12B shows a side view of the tray 1200 with a transparent view of the different erasers 1010 inserted therein. For instance, the first eraser 1010*a* is inserted into slot 1201 and second eraser 1010*b* is inserted into slot 1202.

Each slot includes a chamber 1210 with a bottom surface 1215. The chamber size and depth of the bottom surface varies based on the specific type of eraser.

As shown in FIG. 12B, the motion stabilizing device with the adapter 100 attached thereto, and with a mascara applicator inserted into the adapter, can be moved in a downward motion to receive the eraser 1010*b*. The force of the eraser 1010*b* upon the bottom surface of the chamber 1215 will force the eraser to attach to the end of the cosmetic applicator. The base 1031 of the eraser 1010*b*, or the base 1030 of the eraser 1010*a*, is made of a material with a high coefficient of friction such that it "grips" onto the end of the cosmetic applicator. Such a material is known in the art, and is for example rubber. The inner surface of the base of the eraser may include ribs to provide extra friction and gripping force so it remains firmly inserted on the end of the cosmetic applicator.

With regard to the material of the eraser tip 1020 or 1021, this may be made of polyester as is known in the art since this is a hydrophobic material that adheres well to oil-based products. The form factor of the eraser tip is fibrous in nature, but it is not limited as such.

Figure 13:
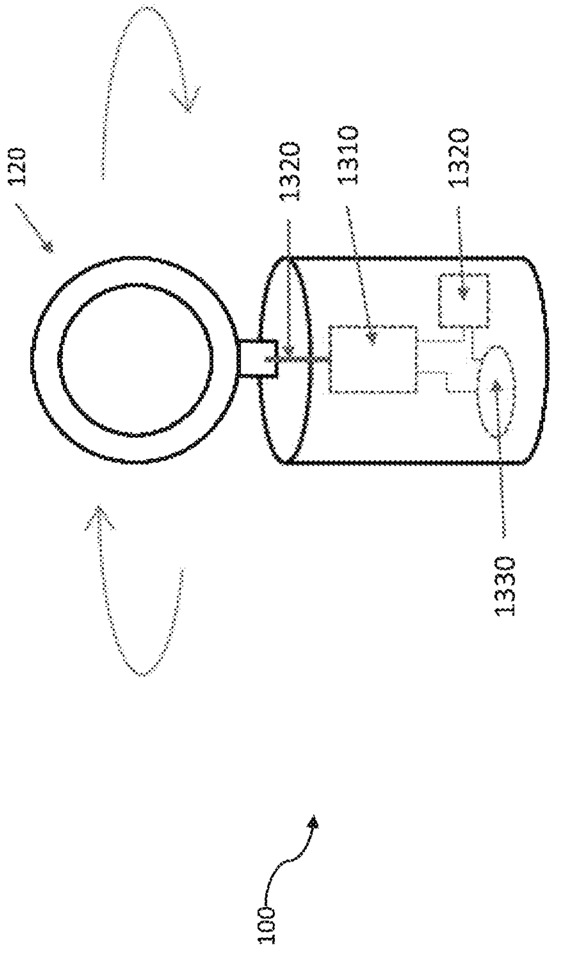
FIG. 13 shows an alternative embodiment in which the rotation of the adapter is controlled to be caused within the adapter itself.

As described above the motion stabilizer can rotate in order to rotate the cosmetic attached to the cosmetic applicator. However, FIG. 13 shows an alternative embodiment in which the rotation of the adapter is controlled to be caused within the adapter itself. In this embodiment, as shown in FIG. 13, the adapter 100 includes a miniature spin motor 1310 as is understood in the art. The spin motor includes a shaft 1320 that is attached to the cosmetic holder 120. The motor is further connected to a power source 1330, which may be a "button battery" as known in the art. In an alternative embodiment, the adapter may receive power from the stabilizer device 150 through the receiver interface of the stabilizer device.

The motor and the power source 1330 are further connected to a microprocessor 1320. The microprocessor controls the rotation of the cosmetic holder 120.

To utilize the eraser 1010 on the back of the cosmetic applicator, the cosmetic holder 120 is caused to rotate approximately 180° by either the motor 1310 or by the rotation of the motion stabilizer device 150.

There are multiple options to trigger the rotation of the cosmetic applicator so that the eraser is facing toward the user. A first option is a manual button (not shown) on the stabilizer device itself. A second option is voice activation where the user audibly speaks a voice command (such as "erase"). The motion stabilizer device 150 includes a microphone (not shown) to enable reception of the voice command, and the motion stabilizer is further configured with voice recognition software in order to process the command (among a plurality of voice activation commands which will be discussed below). A third option is that the motion stabilizer device automatically recognizes that a cosmetic application session has completed, and it automatically rotates the cosmetic holder. This recognition may be based on a delay in movement or pressure sensed by the device exceeding a predetermined threshold.

Figure 14:
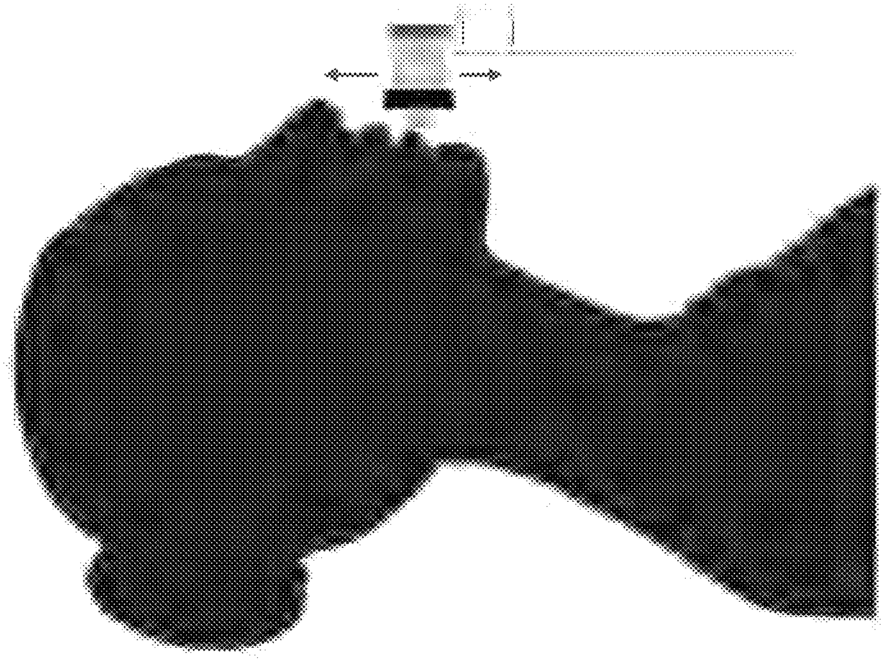
FIG. 14 shows how the motion stabilizer device is configured to make small movements of the eraser when sensing that pressure is applied on the eraser.

In an embodiment, as shown in FIG. 14, the motion stabilizer device is configured to make small movements of the eraser when sensing that pressure is applied on the eraser. This allows the user to avoid attempting to make small "wiping" motions to clean off any smudges or errors in the cosmetic application process. A default type of movement may be started, such as a sideways movement, an up and down movement, or a circular movement.

Alternatively, the specific type of wiping movement may be controlled by the user by voice command. For instance, the user may utter a command such as "erase with sideways wiping at X %" or "erase with up and down wiping at Y %" or "erase with circular wiping at Z %." The percentage indicated by user may be a relative amount of distance that the eraser is moving in each direction, so that the user may cause small movements are large movements by the eraser as desired.

Figure 15:
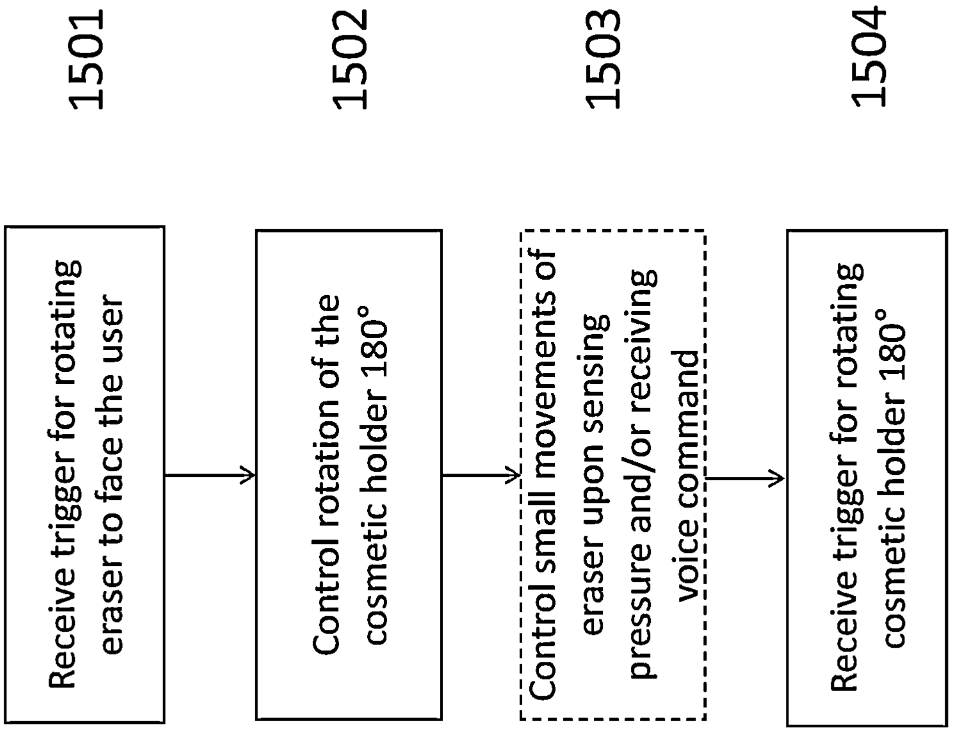
FIG. 15 shows a flow chart for the operation of the eraser feature according to an embodiment.

FIG. 15 shows a flow chart for the operation of the eraser feature according to an embodiment. In step 1501, the microprocessor or the motion stabilizer device receives a trigger for rotating the eraser to face the user. The trigger may be one of the three triggers discussed above. In step 1502, the microprocessor or the motion stabilizer device controls rotation of the cosmetic holder 180°. In step 1503, the motion stabilizer device controls the eraser to perform small movements to perform the "wiping" action of the eraser. This step is optional and may be caused based on sensing pressure of the eraser against the user's skin, or based on receiving a voice command from the user. In step 1504, when the user is finished performing the erasing operation, the microprocessor or the motion stabilizer device controls rotation of the cosmetic holder 180° so that the cosmetic applicator again faces the user.

Figure 16:
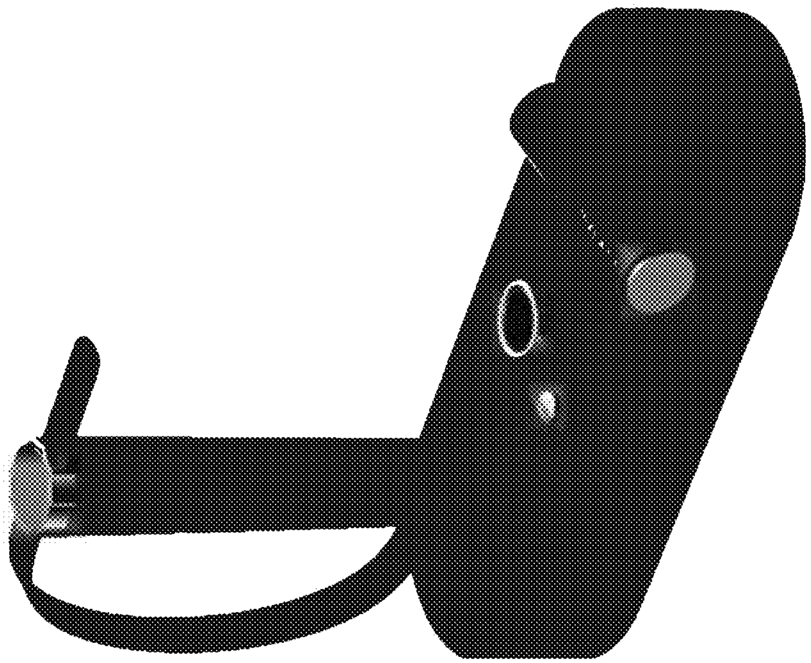
FIG. 16 shows a securement apparatus with the motion stabilizing device in an embodiment.

In one embodiment, the cosmetic applicator can be inserted into, connected to, or otherwise coupled with a securement apparatus (which may be referred to as a "base" or "stand" or "assistive stand" throughout this specification). FIG. 16 shows the securement apparatus with the motion stabilizing device and other features which will be described in more detail below. The securement apparatus can include one or more mechanical components configured to secure a cosmetic tool or product and perform one or more functions with the cosmetic.

The present inventors recognize that for people suffering from motion disorders, assistance is needed in the setup and preparation prior to applying make-up in addition to the actual application of make-up itself. The securement apparatus described herein provides added functions to aid the user in setup and preparation for cosmetic applications.

The added functions can include, but are not limited to, opening, separating, extending, extruding, twisting, shaking, mixing, closing, and/or fastening the cosmetic tool or product. In particular, the one or more functions can be especially useful when the cosmetic includes more than one component. For example, a tube of mascara includes a cap, the cap being attached to a mascara wand, and a body, the body containing the mascara formula. The cap must be twisted relative to the body such that threads on the inside of the cap align with threads on the body in order to open or close the tube of mascara. In another example, an eyeliner pencil can include a cap that covers the pencil tip. The cap must be removed in order to use the eyeliner pencil and replaced to cover the pencil tip when the eyeliner is not in use. In these cases and others, there is often a narrow opening (e.g., the opening of the body, the opening of the cap) in one component of the cosmetic into which another component of the cosmetic is inserted. A user must align the first component with the opening of the second. A precise linear movement is then needed to insert the cosmetic component into the opening or to remove the cosmetic component for use from the opening. The alignment and motion can be difficult for a user who experiences hand tremors or other involuntary motions. In some embodiments, opening and closing a cosmetic can require a rotational (twisting) movement or a combination of translational and rotational movements. Further similar movements may be needed during the cosmetic application process. For example, a user may need to insert the mascara wand into the body to collect more formula with the mascara wand in order to continue applying the mascara. These movements can be difficult for users with a weak grip, a limited range of motion, or limited control over their fine motor skills. Each component of the cosmetic tool must be secured to apply the proper force and leverage needed for the various functions described herein. The securement apparatus of the present disclosure can secure one or more components of a cosmetic tool in order to facilitate any functions of or interactions between the components of the cosmetic tool. In one embodiment, the securement apparatus can limit motion of the cosmetics to counteract the effects of involuntary user movement. In one embodiment, the securement apparatus can apply a force to the one or more components. In one embodiment, the securement apparatus can transform an input force to an appropriate applied force on the one or more components.

Figure 17:
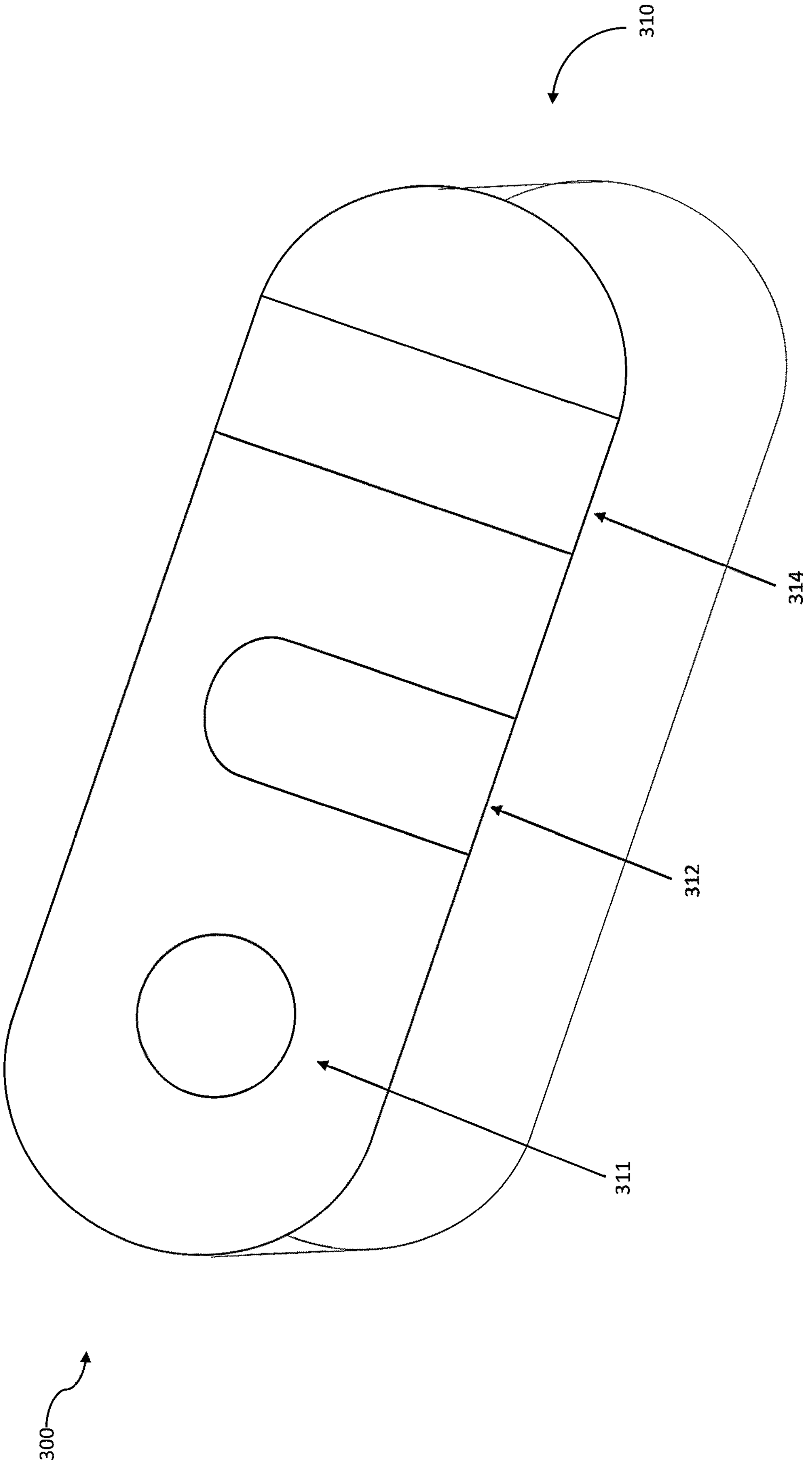
FIG. 17 is an illustration of the securement apparatus, according to one embodiment.

FIG. 17 is an illustration of the securement apparatus, according to one embodiment of the present disclosure. The securement apparatus 300 can include a base 310. The base can form one or more openings and/or chambers for securing a cosmetic or the cosmetic applicator 100. For example, the securement assembly 300 can include a vertical chamber 311 inside the base terminating in an opening at the surface of the base 310. The securement assembly 300 can further include a first horizontal chamber 312, the horizontal chamber being a channel disposed across a portion of the surface of the base 310 and terminating at one end of the base 310. The securement assembly 300 can further include a second horizontal chamber 314, the second horizontal chamber 314 being a channel disposed across the width of the base 310 at the surface of the base 310. Cosmetics and/or cosmetic applicators, such as the adapter 100 of FIG. 5A, can be inserted into the chambers 311, 312, 314. The cosmetics and/or cosmetic applicators can be secured in various positions in the chambers. For example, a cosmetic can be secured in an upright position in the vertical chamber 311. The cosmetic can alternatively be secured in a horizontal position in the first horizontal chamber 312 or the second horizontal chamber 314. Various dimensions, depths, and shapes of chambers are compatible with the present apparatus. In some embodiments, a chamber can be an angled channel. A cosmetic can be inserted into the chamber such that a first end of the cosmetic is elevated relative to an opposite end of the cosmetic. An angled channel can be useful when the cosmetic contains a liquid product so as not to spill the product. In one embodiment, the securement apparatus can include one or more fasteners for securing a cosmetic tool or product in place in a chamber. The fastener can include, for example, a strap that can be wrapped around a portion of the cosmetic tool or product. In one embodiment, the fastener can be self-affixing or can be affixed to the base. According to one example, the fastener can be a strip of hook-and-loop fabric. In one embodiment, the base can include one or more motorized components to apply a force to a cosmetic that is secured by the apparatus. In one embodiment, a motorized component can be disposed inside of or surrounding a chamber in the base, as well be described in further detail herein.

In one embodiment, the chambers for securing the cosmetics can sit atop the base 310 or can be elevated above the base 310. For example, a tube or sheath can be disposed on top of a stem or platform on the surface of the base 310. The tube can be a semi-cylindrical shape forming a chamber. The tube can be elevated above the base 310 so that an inserted cosmetic can be accessed from various angles or positions. In one embodiment, the tube can be attached to the stem or platform via a joint, such as a ball joint. The angle of the tube can be adjusted by applying a force to the tube. As another example, the chamber can be formed by a vertical tube disposed on the top surface of the base 310. A cosmetic can be inserted into the opening of the vertical tube such that the entire cosmetic is still external to the base 310.

Figure 18A:
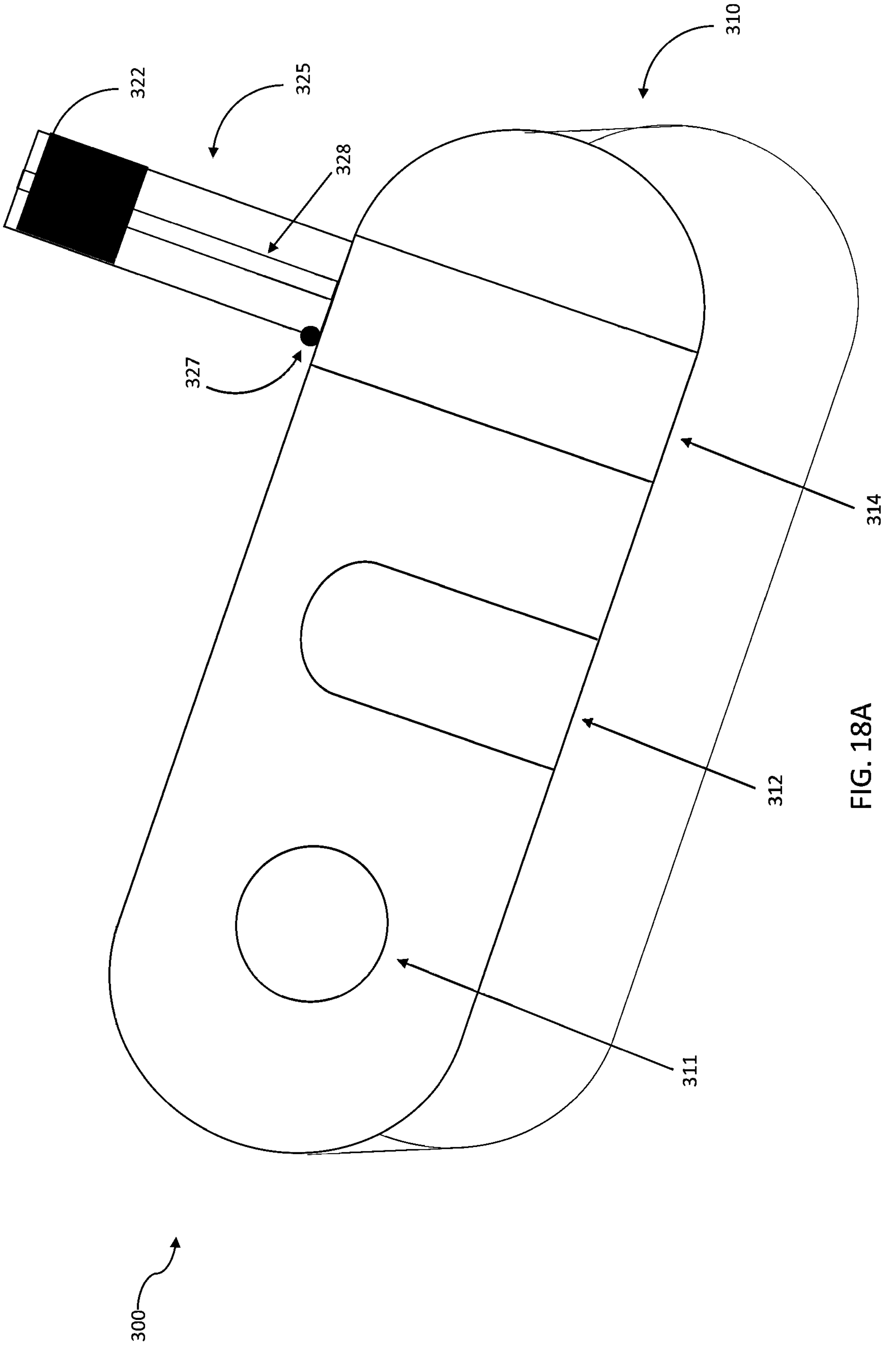
FIG. 18A of a securement apparatus with a track, according to one embodiment.

FIG. 18A is an illustration of a securement apparatus 300, according to one embodiment of the present disclosure. The body of the securement apparatus can include a track 325, wherein a carriage 322 can be coupled to the track 325 and can move along the track, for example along a rail 328. In some embodiments, the carriage 322 can be removably coupled to the track. For example, the carriage 322 can be magnetically attached to the track. In one embodiment, the carriage 322 can include an overhang, wherein the overhang wraps around a portion along the length of the track to secure the carriage to the track. The carriage can slide along the track because the overhang is loosely wrapped around the track and does not prohibit lateral movement of the carriage along the track. In one embodiment, the carriage can include one or more wheels or gears, wherein the one or more wheels are fixed in grooves running lengthwise along the track and can roll along the track to transport the carriage. The track 325 can guide and limit the range of motion of the carriage 322. According to some embodiments, the track 325 can extend outward from the base 310 of the secure attachment such that the coupled carriage can move towards and away from the base 310. In some embodiments, the carriage 322 can be connected to an arm extending from the base 310 and be coupled to the track 325. The arm can facilitate the movement of the carriage 322 along the track.

The carriage 322 can form a chamber for securing a cosmetic tool or product. The carriage 322 can be, for example, a cylindrical or semi-cylindrical sheath, wherein a cosmetic tool or product can be inserted into the sheath. In some embodiments, the carriage 322 can secure the adapter 100 of FIG. 5A. The carriage 322 can include a structural or material feature that secures the cosmetic applicator in the carriage. As an exemplary implementation, the carriage 322 can include at least one magnet, wherein the magnet at the base of the cosmetic applicator can attach to the at least one magnet in the carriage 322. Alternate or additional features for securing the cosmetic applicator 100 can include, but are not limited to, a snap-fit feature or an inner material lining such as rubber that is configured to grip the cosmetic applicator 100. For example, the carriage 322 can include a set of snap-fit protrusions, or teeth. A force can be applied to distort the protrusions and fit the body of the adapter 100 past the protrusions to be secured in the chamber formed by the carriage. In some embodiments, the cosmetic applicator can be inserted into the carriage while the cosmetic applicator is attached to the motion stabilizer 150.

Figure 18B:
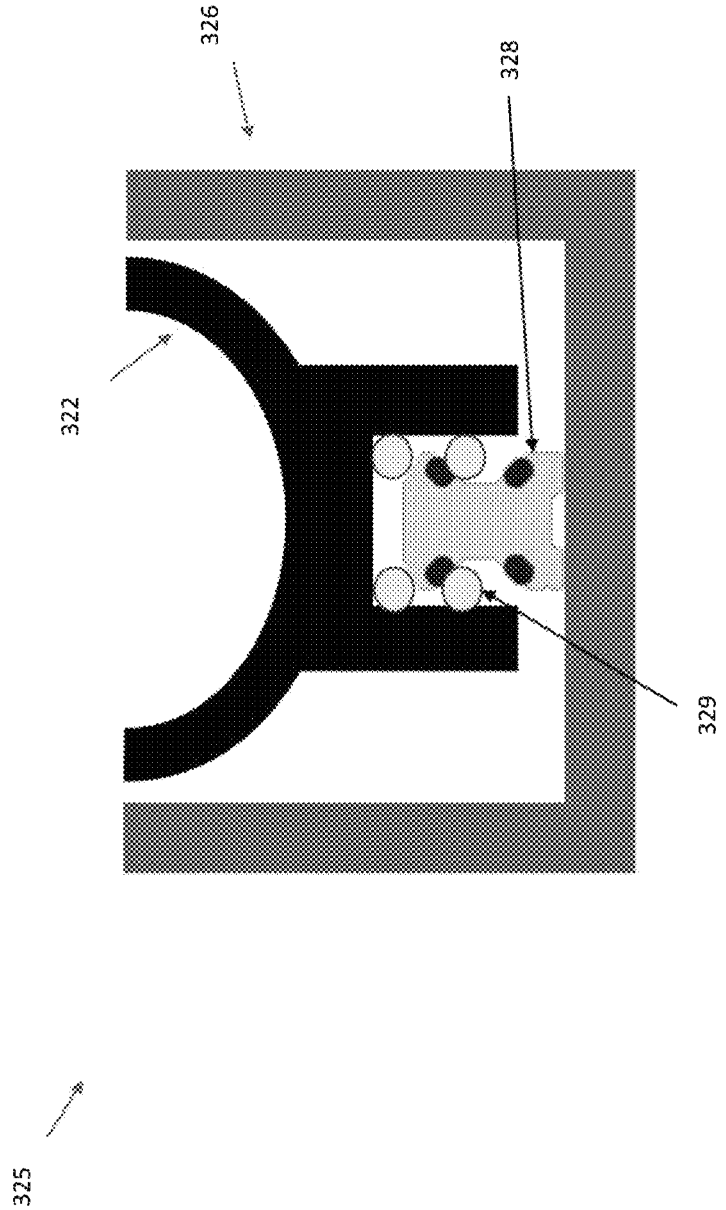
FIG. 18B shows a cross-section of a specific implementation of the track and carriage according to an embodiment.

FIG. 18B shows a cross-section of a specific implementation of the track and carriage according to an embodiment, which is achieved using a linear slide. FIG. 18B shows outer housing 326 of the track 325. The carriage 326 includes a saddle portion that is curved to hold the mascara handle. Beneath the carriage is a rail 328 which is also seen from overhead in FIG. 18B. The carriage houses a set of bearings 329 which allow the carriage to slide along the rail 328. Linear bearing slides are well understood in the art and are described in detail in, for example, U.S. Pat. Nos. 3,897,119 and 6,733,097.

A pushing force can be applied to the carriage 322 to slide the carriage and the attached cosmetic applicator and cosmetic along the track 325. In one embodiment, a first cosmetic component can be secured in the carriage 322 and a second cosmetic component can be secured in a chamber 314 on the base 310 of the securement apparatus. The track 325 can be aligned with the chamber 314 such that the first cosmetic component can be inserted into the second cosmetic component when the carriage 322 slides along the track towards the chamber 314. In this manner, a single force can be applied to the carriage 322 to cause linear motion. A pushing force can be applied to various points on the carriage, the cosmetic applicator, or the cosmetic to move the carriage assembly along the track. The pushing force only needs to have any force component that is parallel to the track in order to cause motion along the track.

Aside from a manual pushing force, the carriage can be controlled to move up and down the track by hydraulic means, pneumatic means, or it can be powered by electric means such as linear actuation, as is understood in the art.

In one embodiment, the cosmetic applicator can be removably coupled directly to the track 325. For example, the track 325 can include a magnetic rail running along the length of the track. The magnet at the base of the adapter 100 can be attached to the magnetic rail, and the adapter 100 can slide along the track 325. Alternative or additional mechanical, structural, and material features described herein and known to one of ordinary skill in the art can be used to couple the adapter 100 directly to the track 325. The adapter 100 can later be removed from the track 325 to be attached to a motion stabilizer or used otherwise. In some embodiments, the cosmetic tool or product can be directly coupled to the track 325.

The attachment of the cosmetic applicator to the track 325 can give a user more control over the movement of the secured cosmetic tool or product. For example, it can be difficult for a user to grip a cosmetic or a motion stabilizer and move the cosmetic at the same time. It can also be difficult for users to grip a first cosmetic component and insert the first cosmetic component into an opening in a second cosmetic component or remove the first cosmetic component from the opening. These openings can be narrow and require the user to stabilize both the first and the second cosmetic component for insertion or removal. The securement assembly can secure and stabilize cosmetic components and any movements thereof. When the cosmetic is secured in the carriage 322, the user can apply a pushing force to the carriage 322 to move the cosmetic tool or product. In some embodiments, the movement of the carriage can be aligned with the position of a cosmetic secured in the base 310 of the securement apparatus. For example, the body of a tube of mascara can be secured in the channel 314 of the base 310. The cap of the tube of mascara, which forms the mascara wand that is applied to the eyelashes, can be secured in a cosmetic applicator. The cosmetic applicator can be attached to the carriage 322. The opening of the mascara tube body can face the mascara wand. The height of the carriage can be fixed by the track 325 so that the attached mascara wand is at the same height of, or more specifically at a center of, the opening of the mascara tube body. The carriage 322 can be pushed along the track 325 in a single direction towards and away from the mascara tube body. The carriage 322 can be pushed towards the mascara tube body until the wand is inserted into the tube body. The carriage 322 can also be pushed away from the mascara tube body until the wand is fully removed from the tube body. The user does not need to align the mascara wand with the opening in the tube body while pushing the mascara wand. In addition, the track 325 can constrain movement of the mascara wand. For example, the mascara wand will not move from side to side because the wand is constrained by the carriage 322 and the movement of the carriage 322 is constrained by the track 325. Any shaking or sudden movements of the user's hand will not derail the carriage 322 or cause side-to-side movement. The moving carriage 322 can help the user open and close the tube of mascara, as well as reapply mascara formula to the mascara wand.

According to one example, the moving carriage can also be used to agitate or mix a cosmetic product. For example, a tube of cosmetic fluid can be placed in the carriage and a pushing force can be applied to move the carriage back and forth along the track. The motion of the carriage can shake the cosmetic fluid for a desired effect, such as mixing or removing the fluid from the walls of the tube. The alignment of the carriage with the base and the constrained motion of the arm can enable the necessary movement of the mascara cap for users who would otherwise not be able to perform these functions.

Various orientations, widths, and lengths of the track 325 are compatible with the securement apparatus of FIG. 18A. In some embodiments, the track 325 can be approximately parallel to the base. The cosmetic or cosmetic applicator 100 can be coupled to the track 325 on top of the track, below the track, or to the side of the track. In some embodiments, the track 325 can extend upwards from the base 310. In an example, a vertical force can be applied to a cosmetic applicator coupled with the track to move the cosmetic down, towards the base, or up, away from the base. In some embodiments, the track 325 can extend upwards at a non-perpendicular angle from the base 310.

In one embodiment, the track can hold more than one cosmetic or cosmetic applicator. As an exemplary implementation, the track can include more than one magnet. A magnetic cosmetic applicator can be attached to each magnet disposed on the track. Each cosmetic applicator can be displaced along the track independently. According to one embodiment, the track can be compressed for storage and expanded or extended for proper usage. In one example, the track can include one or more hinges. The track can be folded at the one or more hinges to shorten the track when the track is not in use. In one embodiment, a hinge can be located at or near the attachment of the track to the base. In one example, the track can be a telescoping track. A telescoping track can be collapsed by pushing on the end of the track such that portions along the length of the track fit into each other. The telescoping track can be expanded by pulling at the end of the track such that the collapsed portions extend. In one embodiment, the track can be attached to the base with a hinge or joint 327 such that the track can pivot around at least one axis of rotation formed by the attachment of the track to the base. For example, the track can be positioned against the base when the track is not in use. The track can then be rotated away from the base and can extend outwards from the base, e.g., to be aligned with a cosmetic component being secured by the base.

In one embodiment, the track 325 can be fixed in various positions and states. The track 325 and/or the base 310 can include at least one locking mechanism to lock the track in a position. For example, the track can be attached to the base with a hinge 327. The hinge can include a spring or a stopper that provides a force or resistance to lock the track in at least one position. The at least one position can correspond to an angle between the track and the base or a distance between the track and the base. For example, the track can be locked in an open position, wherein the track forms a straight line with a chamber in the base 310. In one position, the fixed position can be a maximum displacement of the track corresponding to a maximum possible rotation of a hinge leaf around a hinge pin. In one embodiment, the hinge can be unlocked with an applied force to the track, such as a pushing force to return the track to a closed position against the base. In one embodiment, the track can lock in more than one position, wherein each position corresponds to a use case for the securement assembly. For example, a first position can be aligned with a first opening in the base, a second position can be aligned with a second opening in the base, etc. In another example, the positions of the track can be vertical positions at an angle relative to the base. A first position can correspond to a first angle between the track and the base, a second position can correspond to a second angle between the track and the base, etc. Additional or alternative mechanisms known to one of ordinary skill in the art for locking a rotating component can be implemented to fix the track in a position relative to the base. Advantageously, the fixed position of the track can be configured by the mechanical attachment of the track to the base. Thus, a user does not need to determine or estimate the position of the track that best aligns with the base. The user can simply move the track until the locking mechanism is activated and use the track in its fixed position.

Figure 18C:
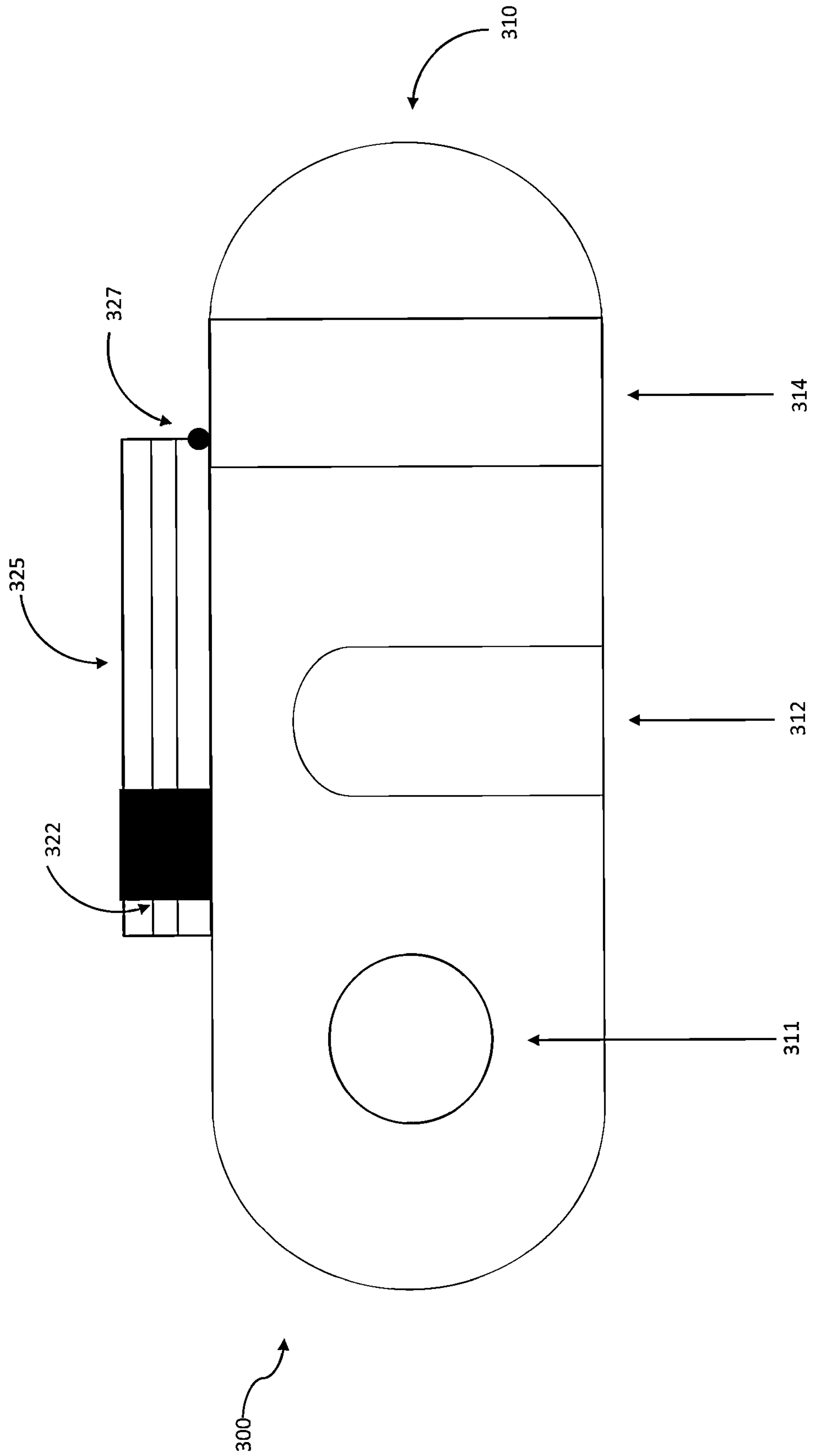
FIG. 18C is an illustration of the track in a closed position, according to an embodiment.

FIG. 18C is a top view of a securement assembly 300, according to one embodiment of the present disclosure. The base 310 of the securement assembly 300 can form one or more chambers for securing cosmetic components. For example, the securement assembly 300 can include a vertical chamber 311 inside the base terminating in an opening at the surface of the base 310. The securement assembly 300 can further include a first horizontal chamber 312, the horizontal chamber being a channel disposed across a portion of the surface of the base 310 and terminating at one end of the base 310. The securement assembly 300 can further include a second horizontal chamber 314, the second horizontal chamber 314 being a channel disposed across the width of the base 310 at the surface of the base 310. Cosmetics and/or cosmetic applicators, such as the adapter 100 of FIG. 5A, can be inserted into the chambers 311, 312, 314. The cosmetics and/or cosmetic applicators can be secured in various positions in the chambers. For example, a cosmetic can be secured in an upright position in the vertical chamber 311. The cosmetic can alternatively be secured in a horizontal position in the first horizontal chamber 312 or the second horizontal chamber 314. The securement can include a track 325 attached to the base 310. In some embodiments, a carriage can be attached to the track 325, wherein the carriage can secure a cosmetic or a cosmetic applicator such as the applicator 100 of FIG. 5A. FIG. 18C is an illustration of a track 325 in a closed position, wherein the track 325 is positioned against the base 310. The track 325 can be attached to the base 310 with a hinge 327.

Figure 18D:
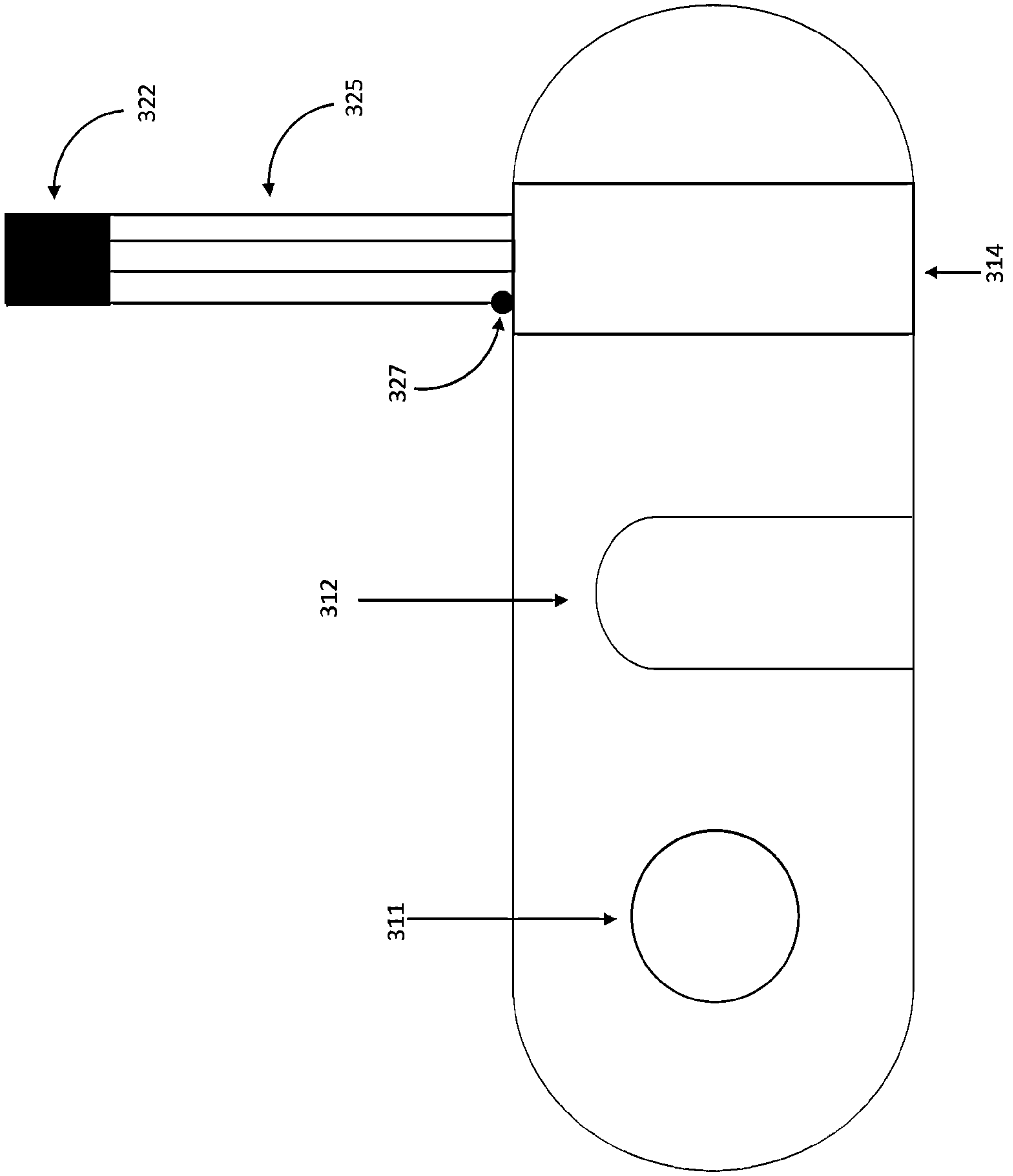
FIG. 18D is an illustration of an overhead view of the track in an open position, according to an embodiment.

FIG. 18D is an illustration of a securement assembly 300, according to one embodiment of the present disclosure. The base 310 of the securement assembly 300 can form one or more chambers for securing cosmetic components. For example, the securement assembly 300 can include a vertical chamber 311 inside the base terminating in an opening at the surface of the base 310. The securement assembly 300 can further include a first horizontal chamber 312, the horizontal chamber being a channel disposed across a portion of the surface of the base 310 and terminating at one end of the base 310. The securement assembly 300 can further include a second horizontal chamber 314, the second horizontal chamber 314 being a channel disposed across the width of the base 310 at the surface of the base 310. Cosmetics and/or cosmetic applicators, such as the adapter 100 of FIG. 5A, can be inserted into the chambers 311, 312, 314. The cosmetics and/or cosmetic applicators can be secured in various positions in the chambers. For example, a cosmetic can be secured in an upright position in the vertical chamber 311. The cosmetic can alternatively be secured in a horizontal position in the first horizontal chamber 312 or the second horizontal chamber 314. The securement can include a track 325 attached to the base 310. In some embodiments, a carriage can be attached to the track 325, wherein the carriage can secure a cosmetic or a cosmetic applicator such as the adapter 100 of FIG. 5A. The securement assembly 300 can include a track 325 attached to the base 310 with a hinge 327. The track 325 can pivot around the axis of the hinge into an open position, as pictured in FIG. 18C. The track can form a straight line extending from a horizontal chamber 314 in the base to the end of the track 325. In one embodiment, the open position of the track 325 can be the position corresponding to a maximum rotation of the hinge 327. The track 325 and the horizontal chamber 314 are aligned in the open position. The carriage 322 can slide down the track 325 to the end of the horizontal chamber 314 at the edge of the base 310. The width of the track can be approximately the width of the chamber 314 or can be wider or narrower than the chamber 314.

Figure 19:
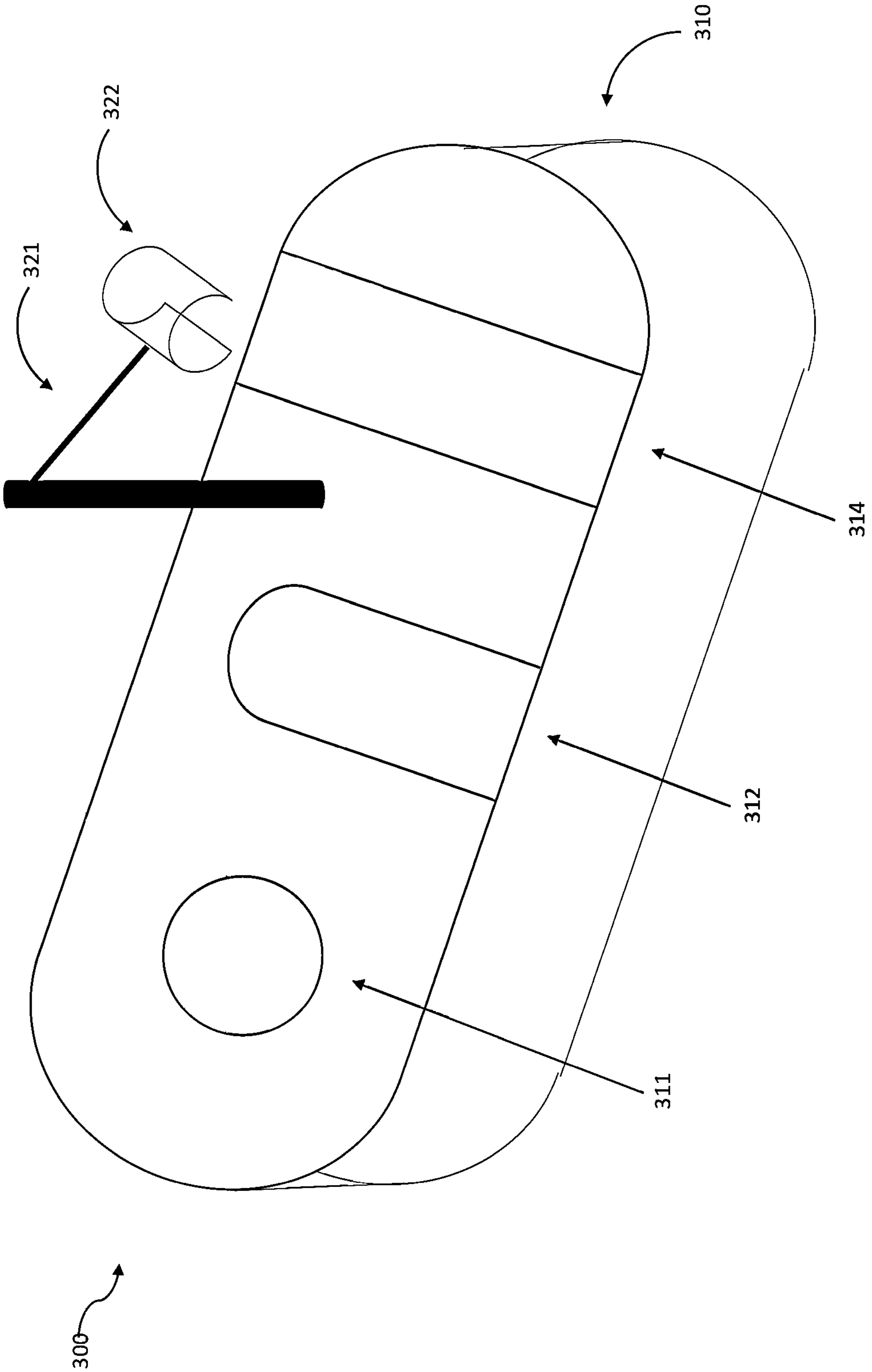
FIG. 19 is an illustration of the securement apparatus with an arm to control movement of a cosmetic applicator, according to an embodiment.

The securement assembly 300 can include various apparatuses configured to secure and move a cosmetic. FIG. 19 is an illustration of the securement apparatus, according to one embodiment of the present disclosure. In one embodiment, a mechanical arm 321 can be attached to the base 310 of the securement apparatus. The arm 321 can secure a cosmetic and can control the movement of the secured cosmetic. In some embodiments, the arm 321 can expand the range of motion of the cosmetic and can enable greater degrees of freedom than alternative structures. In one embodiment, the arm 321 can be attached to the base 310 with a joint, such as a ball joint. The arm 321 can swivel or pivot in at least one direction relative to the fixed base 310. In another embodiment, the arm 321 can be fixed. In one embodiment, the arm 321 can be jointed such that the arm 321 can be folded and unfolded. In one embodiment, the arm 321 can be bent. For example, a first portion of the arm can extend upwards from the top surface of the base and be perpendicular to the base 310. The arm can be bent at a joint, and a second portion of the arm past the joint can extend in a single direction and can be configured with a range of motion. In one embodiment, the arm can be curved. The arm 321 can be attached to a carriage 322, wherein the carriage 322 can form a chamber for securing a cosmetic tool or product, or the adapter 100 of FIG. 5A. According to one embodiment, the carriage 322 can pivot relative to the arm 321. For example, the carriage 322 can be attached to the arm 321 with a ball joint, such that the carriage 322 can rotate around the ball joint.

In one embodiment, the carriage 322 can move when the arm 321 pivots around the attachment joint between the arm 321 and the base 310. In one embodiment, the arm 321 can pivot around a fixed point, such as a joint, along the arm 321. For example, the arm 321 can have a joint (e.g., a pin joint, a ball joint) along the length of the arm, wherein a portion of the arm extending past the joint can pivot at the joint while the portion of the arm below the joint is fixed. Alternate mechanical joints and fixed points enabling movement of a component attached to the arm are compatible with the presently disclosed apparatus. In one embodiment, the degree of rotation or the displacement of the arm 321 can be limited. For example, the arm 321 can include a pin joint. The rotation of the pin in the pin joint can be constrained, thus limiting the motion of the arm. In one embodiment, one or more joints can be configured such that differing amounts of force must be applied to move the arm in differing directions or dimensions. For example, one or more joints in the arm can be configured such that greater force must be applied to move the arm in a z-axis direction (e.g., up and down) than must be applied to move the arm in an x-axis direction (e.g., from side to side). The carriage 322 attached to the arm 321 can thus move in the constrained directions. A user can apply a pushing or pulling force to the carriage 322 to move the carriage 322 in a direction. The arm 321 can control the direction of movement of the carriage 322 and can constrain the movement of the carriage 322. It can be easier for a user to push the carriage 322 to achieve movement of an attached cosmetic than it is to grip and move the cosmetic themselves. The constrained movement of the carriage 322 can also prevent the user from accidentally displacing the cosmetic as a result of any tremors or involuntary movements. In one embodiment, the movement of the carriage 322 can follow a curved path, wherein the curvature of the path is dependent on the length of the arm. In one embodiment, the path of the arm can be configured by the fixed positions and movements of the arm so that the carriage 322 is aligned with a chamber in the base 310. A user can then apply a pushing force to the carriage 322 to move an attached cosmetic towards and away from the chamber for any of the functions that have been described herein.

According to some embodiments, movement of a cosmetic or a cosmetic applicator relative to the base of the securement assembly can be automated. The cosmetic or cosmetic applicator can be attached to a carriage, wherein the carriage is attached to a track or an arm. As noted above, the carriage can be controlled to move up and down the track by hydraulic means, pneumatic means, or it can be powered by electric means such as linear actuation, as is understood in the art. The movement of the carriage can be automated by at least one motorized component such that the carriage can move without external force being applied to the carriage or the cosmetic by the user. In one embodiment, the movement of the cosmetic or cosmetic applicator can be controlled with input from a switch, a button, a joystick, or similar user interface. In one embodiment, the movement of the cosmetic or cosmetic applicator can be controlled using an application, such as a mobile application. The application can be configured to initiate the transmission of instructions regarding the movement of the cosmetic or cosmetic applicator to the securement assembly.

In one embodiment, data from at least one sensor can be used to initialize, configure, or terminate movement of the attached cosmetic or the cosmetic applicator. For example, the carriage can include at least one sensor disposed on or inside the carriage. The at least one sensor can be a physical sensor, such as a pressure sensor, a light sensor, an infrared (IR) sensor, or a Hall sensor. The readings from the at least one sensor can indicate when a cosmetic or a cosmetic applicator is attached to the carriage. For example, the cosmetic applicator can cause an increase in pressure on the inner walls of the carriage. In another example, the cosmetic applicator can block ambient light from reaching the carriage. In another example, the cosmetic applicator can reflect light that is transmitted by an IR sensor disposed on or inside the carriage. In one embodiment, the sensor can detect when a cosmetic applicator is attached to the carriage based on integrated circuitry in the cosmetic applicator. For example, the circuitry in the cosmetic applicator can be configured for a wireless communication protocol. A sensor or other integrated circuitry in the linear slide can be configured for the same wireless communication protocol. The proximity of the cosmetic applicator to the carriage can trigger a signal transmission between the cosmetic applicator and the carriage over the wireless communication protocol. The proximity or attachment of a cosmetic applicator to the carriage can activate movement of the carriage. Similarly, the removal of a cosmetic applicator from the carriage can terminate movement of the carriage. In some embodiments, the movement of the carriage can be dependent on the type of cosmetic attached to the cosmetic applicator. Information about the cosmetic can be detected by a sensor or can be input into a device or apparatus by a user. The device or apparatus can include, but is not limited to, a personal device, as will be described in further detail herein.

In one example, the base of the carriage can be attached to at least one motorized wheel, wherein the at least one motorized wheel can sit on the track 325 of FIG. 18A through FIG. 18D. The motorized wheel can be activated to rotate and roll along the track in response to an electrical signal being transmitted to the securement assembly. The carriage can thus roll along the track without external force being applied to the carriage by the user. In one embodiment, the track can be attached to a motorized component, wherein the motorized component can translate the track or a portion of the track. For example, the track can be a telescopic track, wherein a portion of the track is in contact with a motorized wheel or gear. The portion of the track can sit on top of or underneath the wheel. In one embodiment, the wheel can be attached to the side of the track. The rotation of the motorized wheel can linearly translate the portion of the track to collapse or extend the track. The carriage can be attached to the portion of the track that is collapsed or extended. The carriage can be transported closer to and further away from the base as the track collapses and extends. In one embodiment, the motorized component can be disposed inside the base and can be in contact with a portion of the track that extends into the base. The motorized component can rotate or otherwise be activated to apply a force in a first direction to the track and retract the track further into the base. The motorized component can also rotate or otherwise be activated to apply a force in an opposing direction to extend the track out from the base.

In one embodiment, the arm 321 of FIG. 19 can include at least one motorized component for automated movement of the arm. For example, a joint of the arm can be configured to rotate in response to an electrical signal transmitted to the securement assembly. The arm and/or the attached carriage can move without any application of force directly to the arm or the attached carriage. In one embodiment, the arm can be controlled with input from a switch, a button, a joystick, or similar user interface. In one embodiment, the movement of the arm can be controlled using an application, such as a mobile application. In one embodiment, at least one sensor can be disposed in the arm or the attached carriage, the at least one sensor including any of the sensors that have been described herein. Data from the at least one sensor can be used to initialize, configure, or terminate movement of the arm and/or the attached carriage.

In an embodiment, and as will be discussed in a specific example below, there is a capability for not only re-inserting the cosmetic applicator into its reservoir, but also for rotation. For example, with mascara the applicator is guided/inserted into the cosmetic reservoir (i.e. mascara container)

and then a motor rotates the applicator inside the reservoir to fully coat the applicator with cosmetic formula.

Linear motion is an example of a movement that can be enabled or automated by the securement assembly of the present disclosure. In some embodiments, additional movements and types of motion can be enabled by the securement assembly. For example, a rotation of a cosmetic tool or product can be necessary to open the cosmetic, close the cosmetic, or apply formula to a tool. In many cases, a cosmetic product with a tube-shaped body and a cap (e.g., concealer, lip gloss, mascara) can have a thread fit between the tube-shaped body and the cap. Threads on the inside wall of the cap must align with threads on the outer wall of the body in order to convert a rotation of the cap or the body to a linear translation of the components closer to or further away from each other. The cap must be placed over the opening of the body and then rotated in a first direction (e.g., clockwise) in order to close the product. Similarly, the cap must be rotated in an opposite direction from the first direction (e.g., counterclockwise) to be removed from the body. In these instances, the cap and the body must each be rotated in opposite directions, or one component must be rotated while the second component is fixed. Rotating both the cap and the body in the same direction is ineffective for opening and closing the tube but may be useful for agitating the formula inside the tube.

In some embodiments, a cosmetic applicator can be secured to the securement assembly and the attached cosmetic can undergo both translation and rotational motion. In one embodiment, the cosmetic applicator can rotate the attached cosmetic. The holder of the cosmetic applicator can be a ring or an approximately cylindrical sheath, wherein the holder is in contact with the attached cosmetic that is inserted into the holder. In one embodiment, a motor can be attached to the holder. The motor can rotate the holder around the central axis of the holder. The rotation of the holder causes the attached cosmetic to rotate in the same direction and with approximately the same velocity. In some embodiments, the holder can rotate when the cosmetic applicator is attached to the motion stabilizer. The rotation of the holder and the attached cosmetic can automate the movement needed to open or close the attached cosmetic.

In one embodiment, the rotation of the holder can be manually or automatically configured. Cosmetic products have varying dimensions and can be designed with different threading between the cap and the body. Each product may require a different number of rotations to fully open or close the product. In one embodiment, the holder can rotate a set number of times, the set number of times being based on the cosmetic that is attached to the cosmetic applicator. According to one embodiment, the cosmetic applicator can include at least one sensor configured to determine a weight, dimension, or other physical property of the cosmetic that is attached to the cosmetic applicator in order to set the number of rotations. In one embodiment, the number of rotations can be set according to the information about the cosmetic that has been input into a device in communication with the securement assembly, as will be described in further detail herein. In one embodiment, the set number of times can be a maximum number of rotations that is needed to unthread or thread a product. In one embodiment, the number of rotations can depend on a resistance to rotation of the attached cosmetic. For example, when a cap is fully closed on a product, the cap may no longer rotate because the cap is flush with the body and there is no room for further displacement of the cap. The cosmetic applicator can include one or more sensors configured to sense a force, such as a friction force between the holder and the attached cosmetic. If the force required to rotate the attached cosmetic suddenly increases or increases above a threshold, the holder can stop rotating. Similarly, once the cap becomes unthreaded and completely uncoupled from the body, there is no more resistance from physical contact between the cap and the body. The holder can also stop rotating as a result of a sudden decrease in force or a decrease below a threshold.

In one embodiment, the motion stabilizer can rotate or apply a force to rotate the attached cosmetic. For example, the motion stabilizer can rotate in order to spin the cosmetic attached to the cosmetic applicator. In one embodiment, the cosmetic holder of the cosmetic applicator can be concentric with the motion stabilizer. For example, the cosmetic holder can be a cylindrical sheath attached to the adapter of the cosmetic applicator. The cylindrical sheath can be coaxial with the motion stabilizer and extend outward from the motion stabilizer. The attached cosmetic can be inserted into the sheath and will also extend outward from the motion stabilizer along the same axis of the sheath and the motion stabilizer. The cosmetic applicator can be attached to the linear slide of the securement assembly. In one embodiment, the body of the cosmetic applicator can snap into a carriage attached to a track such that the motion stabilizer and the attached cosmetic are parallel to the track. The motion stabilizer can rotate, causing the cosmetic holder and the attached cosmetic to also rotate. The cosmetic applicator can also slide along the track for simultaneous linear motion. The combined motions of the cosmetic can align and couple the attached cosmetic to another cosmetic component, such as a tube body, the tube body being secured by the base of the securement assembly.

In one example, a chamber formed by the base of the securement assembly can include a rotating component. The rotating component can rotate a cosmetic tool or product that is placed in the chamber. In one embodiment, a chamber formed by the base of the securement can include a rotating sheath forming part of the inner surface of the chamber. The sheath can be approximately cylindrical. The sheath can be connected to a motor, wherein the motor can rotate the sheath around the central axis of the sheath. When a cosmetic tool or product is placed inside the chamber, the walls of the rotating sheath can be in contact with the cosmetic. The rotating sheath can exert a grip on the cosmetic due to the tightness of the fit of the cosmetic in the sheath. In one embodiment, the inner wall of the rotating sheath can include raised structures, such as teeth, to increase contact surface area with the cosmetic. The rotation of the rotating sheath can cause the cosmetic to rotate in the same direction and with approximately the same rotational velocity. In one implementation, the cosmetic in the chamber can rotate while a cosmetic in the cosmetic applicator does not rotate. The cosmetic in the cosmetic applicator can move linearly closer to or further away from the cosmetic in the chamber while the cosmetic in the chamber rotates to engage an opening or closing function.

Notably, opening and closing a threaded tube involves both rotation and linear motion because of the helical structure of the threads. Pure rotation while the body and the cap are fixed in place will not open or close the tube. Advantageously, the moving carriage of the securement assembly described herein can enable the linear motion of the cosmetic towards and away from the base while the cosmetic rotates for effective opening and closing of the cosmetic. The securement assembly can align a first cosmetic component with a second cosmetic component. The cosmetic component can then be rotated and/or moved while attached to the securement assembly. The user does not have to first align the components or insert the first component into the second component with any precision. The user can apply a single force, such as a pushing force, to the carriage to move the attached cosmetic. One or more of the motions of the cosmetic attached to the cosmetic applicator can be automated. For example, the cosmetic applicator can rotate the cosmetic while a user pushes the cosmetic along the track to open or close the cosmetic. In another example, the cosmetic applicator can rotate the cosmetic while a motorized component translates the cosmetic to open or close the cosmetic.

In one embodiment, the securement assembly can be configured to open packaging surrounding a cosmetic tool or product. For example, cosmetics can be wrapped in plastic or be disposed inside a plastic casing. The packaging of a cosmetic can be difficult to open for a user with limited mobility, grip strength, or control of fine motor movement. In one embodiment, a cosmetic surrounded by packaging can be attached to the securement assembly. The securement assembly can be used to apply the linear and rotational forces that have been described herein in order to open the packaging. For example, an eyeliner pencil can be wrapped in plastic packaging to prevent the cap of the pencil from being removed before the pencil is purchased. The plastic packaging can be a flexible plastic, wherein a twisting motion of the cap relative to the pencil can break the packaging. The broken packaging will lift up from the pencil and the cap and can be easily grasped and peeled off of the pencil. In one embodiment, the pencil can be placed in a chamber in the base of the securement assembly. The cap of the pencil can be placed inside the cosmetic holder of a cosmetic applicator. The chamber can hold the pencil in place while the cosmetic applicator applies a rotational force to the cap. The rotational force can twist the cap and tear the plastic packaging surrounding the cap. The packaging can then be removed for usage of the eyeliner pencil. The cosmetic applicator and the securement assembly can reduce the number of steps and motions that a user must take to open the packaging.

Figure 20A:
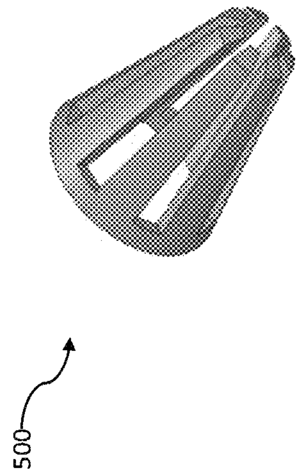
FIGS. 20A, 20B, and 20C are illustrations of an attachment that can be used to remove packaging surrounding a cosmetic, according to one embodiment.
Figure 20B:
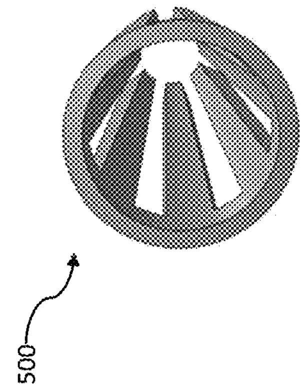
Figure 20C:
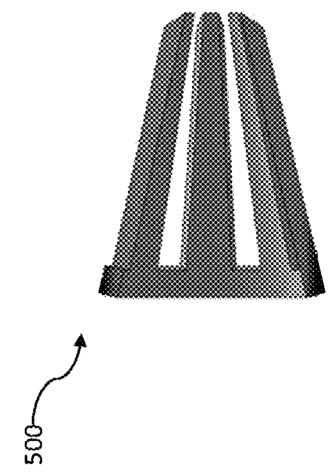

In one embodiment, the securement assembly can include one or more attachments, accessories, or the like to unsheathe packaging surrounding a cosmetic tool or product. FIG. 20A is an illustration of an attachment 500 (cutting element) that can be used to remove packaging surrounding a cosmetic, according to one embodiment of the present disclosure. The attachment 500 can be, for example, attached to a channel in the securement assembly or the linear slide of the securement assembly, as has been described herein. In one embodiment, the attachment 500 can include a number of slats forming a cone with an opening at the vertex of the cone. The slats can be connected to a continuous ring forming a base of the cone. The slats can extend towards the tip of the cone with a separation between each of the slats. The attachment 500 can be a semi-flexible material, such as a plastic. In one embodiment, a cosmetic tool or product can be inserted into the attachment 500 through the wider base of the attachment and the vertex of the cone. The slats can flare outwards as a result of a force applied to the inner walls of the slats when the cosmetic is inserted into the attachment. The slats can flare outwards to widen the opening of the vertex of the attachment to accommodate cosmetics of various shapes and diameters. FIG. 20B is an illustration of the attachment 500, according to one embodiment of the present disclosure. In one embodiment, each slat includes at least one sharp edge or point. The sharp point can be disposed at the end of the slat forming the vertex of the cone and can be pointed inwards towards the center of the vertex. In one embodiment, each slat can have a flat side and a sharp side. For example, each slat can have a sharper inner edge and a flatter outer edge or surface. FIG. 20C is a side view of the attachment 500, according to one embodiment of the present disclosure. The sharp edge of the slat can be in contact with a cosmetic that is inserted through the vertex of the attachment. In some embodiments, the sharp edges can be disposed along the length of the slat such that the sharp edges are not exposed at the outer surfaces of the attachment. In one embodiment, the attachment can include a cover or sheath around the vertex of the attachment so that the sharp edges do not pose a safety risk to anyone handling the attachment.

As an exemplary use case, a cosmetic wrapped in plastic can be inserted into the attachment 500 by passing the cosmetic through the base of the attachment 500 and then through the opening at the vertex of the attachment. The sharp edges of the slats at the vertex of the attachment can be in contact with the plastic surrounding the cosmetic. The cosmetic can then be pulled back through the opening at the vertex of the attachment and the base of the attachment. The sharp edges at the vertex can scratch, tear, or scrape the packaging surrounding the cosmetic. For example, a sharp edge in contact with the plastic packaging of the cosmetic can tear a hole in the packaging when the cosmetic is pulled past the sharp edge. The attachment can thus facilitate the removal of the packaging and the opening of the cosmetic. In one embodiment, the attachment 500 can be placed inside one of the channels of the securement assembly. The packaged cosmetic can be placed in the linear slide and directed into the channel of the securement assembly to be inserted into the attachment. The linear slide can then be moved to remove the packaged cosmetic from the attachment and tear the packaging.

As an additional function included in the securement apparatus, the securement apparatus automatically extends a lipstick tube stored therein so that it is extended to the optimal length for each use.

Figure 21A:
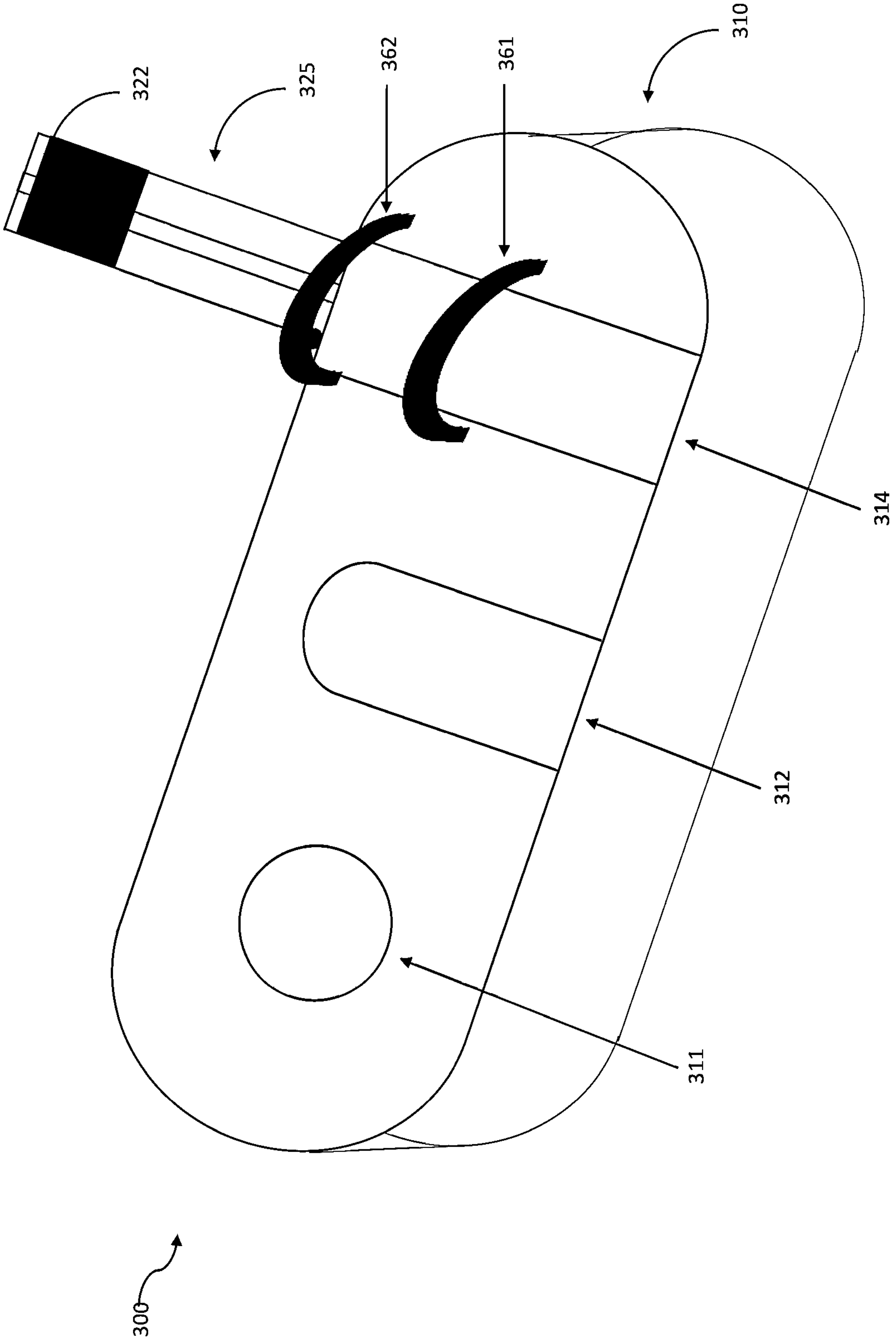
FIGS. 21A, 21B, and 21C show a specific example the securement apparatus with rotating elements, according to an embodiment.

FIG. 21A shows a specific example the securement apparatus 300 achieving certain features which were mentioned above. In FIG. 21A, two rotating elements 361 and 362 are shown covering certain portions of the chamber 314. As will be shown below, when the mascara container is inserted into the chamber 314, rotating element 361 will “grip” the body the container. Rotating element 362 is configured to grip an end portion of the mascara cap which is attached to the mascara wand.

Figure 21B:
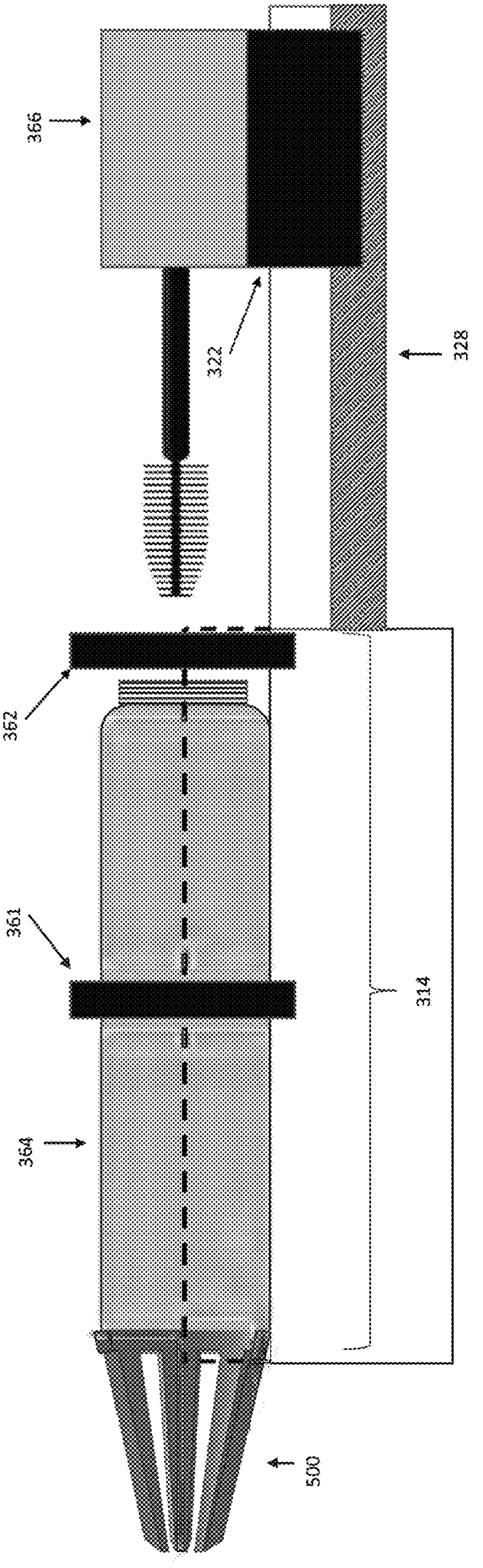
Figure 21C:
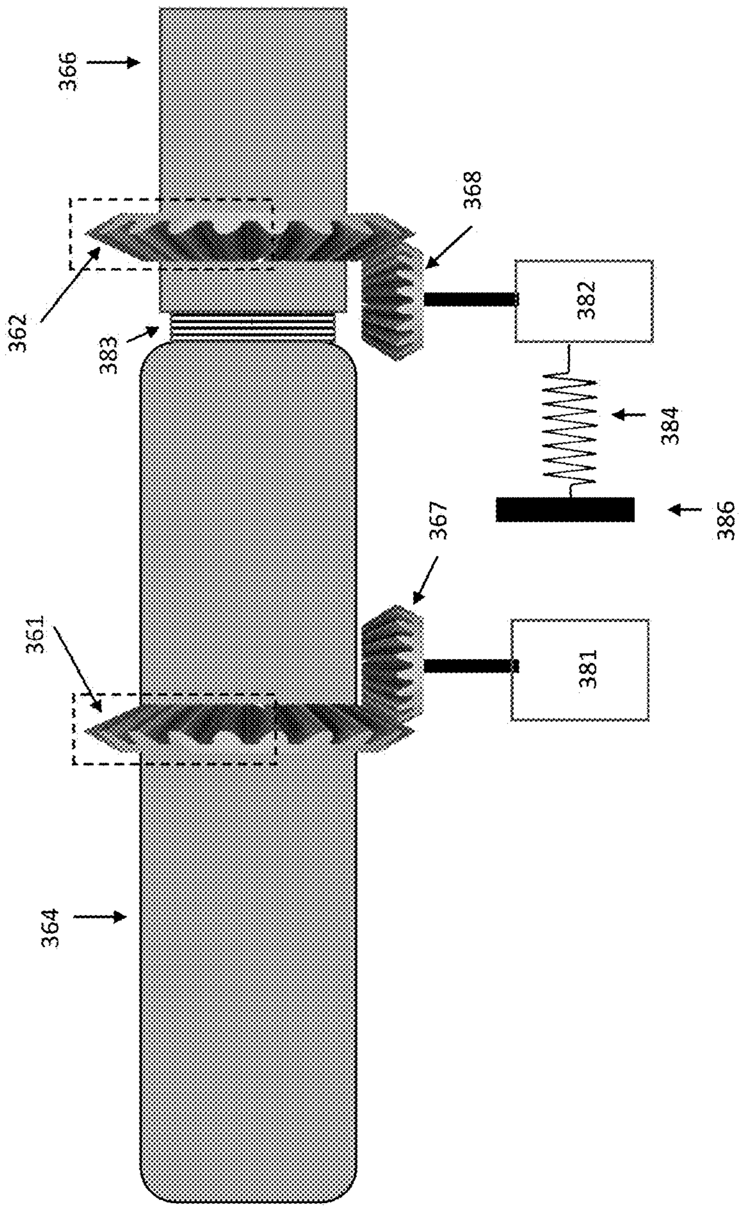

FIGS. 21B-21C show a side view of how the features in FIG. 21 achieve certain effects when an actual mascara container and mascara cap are inserted into the chamber 314.

In FIG. 21B, the mascara container 364 is resting in the chamber 314. The mascara cap 366 is resting on the carriage 322, which is coupled to the rail 328. The first rotating element 361 is in the chamber and grips at least a top half of the mascara container 364. The second rotating element 362 is disposed towards an edge of the securement apparatus and is not in contact with the mascara container 364. It should be noted that each of the rotating elements 361 and 362 essentially rotate through a the housing of the securement apparatus via a semi-circular housing that covers an exterior surface of the rotating element on the outside of the securement apparatus, but it will not cover the rotating element within the interior of the securement apparatus. FIG. 21B further shows that the cutting element 500 is disposed at an end of the chamber 314, such that it can receive a bottom portion of the mascara container 364.

FIG. 21C shows a transparent view on how the rotating elements 361 and 362 operate. The rotating elements 361 and 362 are actually bevel gears that that are controlled to be rotated by motor gears 367 and 368 respectively. The motor gears 367 and 368 are respectively controlled by controllers 381 and 382 respectively. The carriage will deliver the mascara cap up to a point where an interior female screw threads inside the cap 366 (not shown) lock onto the mail screw threads 383 on the mascara container 364. The rotating element 362 is then controlled to be turned so that the cap 366 screws onto the mascara container 364 until it is completely shut. The structure of the combination of the bevel gear 362, the motor gear 368, and the controller 382 is designed to be movable and attached to a spring 384 which is attached to a fixed point 386. This allows the cap to move slightly in two directions to allow the screwing or unscrewing of the cap as needed. With this mechanism, the mascara container can be automatically attached to the mascara cap when the user is done using the mascara applicator.

In FIG. 21C, the rotating element 361 can be used to rotate the mascara container 364 when needed. For instance, when the container still has an outer plastic packaging, the rotation of element 361 allows the container to move against the sharp edges of the attachment 500, and unsheathe the container from the packaging. Furthermore, the rotating element 361 can allow the mascara fluid inside the container to mixed when necessary.

Figure 21D:
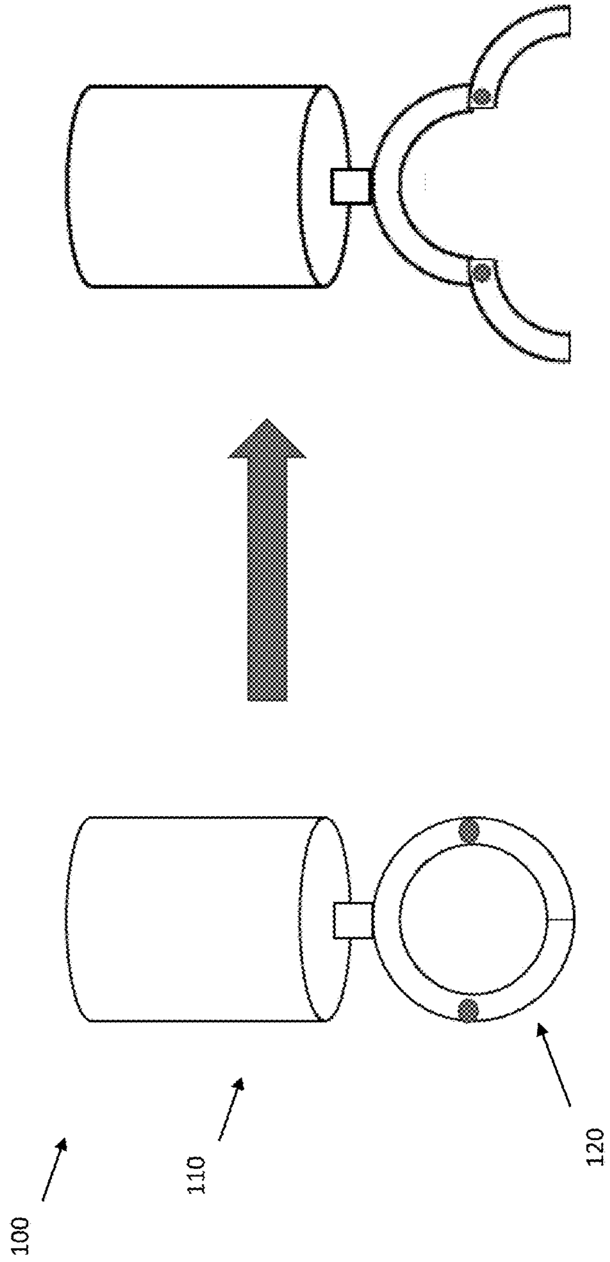
FIG. 21D shows that the cosmetic holder of the adapter can open to release a cosmetic application, according to an embodiment.

FIG. 21D illustrates an additional feature which enables the user to avoid too many hand movements when returning the mascara applicator to the container. In FIG. 21D, the adapter 100 is shown in the upside down position with adapter body 110 over the cosmetic holder 120. It can be seen that in this embodiment, cosmetic holder 120 includes hinges 128. As shown, the cosmetic holder can rotate along the hinges allowing the ring element to separate at the bottom most point. If a cosmetic application was being held by the adapter 100, this would allow the cosmetic applicator to be "released" while the uses is using the motion stabilizer. Thus, the user could release a mascara applicator directly onto the carriage 22 shown above while using the assistance of the motion stabilizer.

Figure 22A:
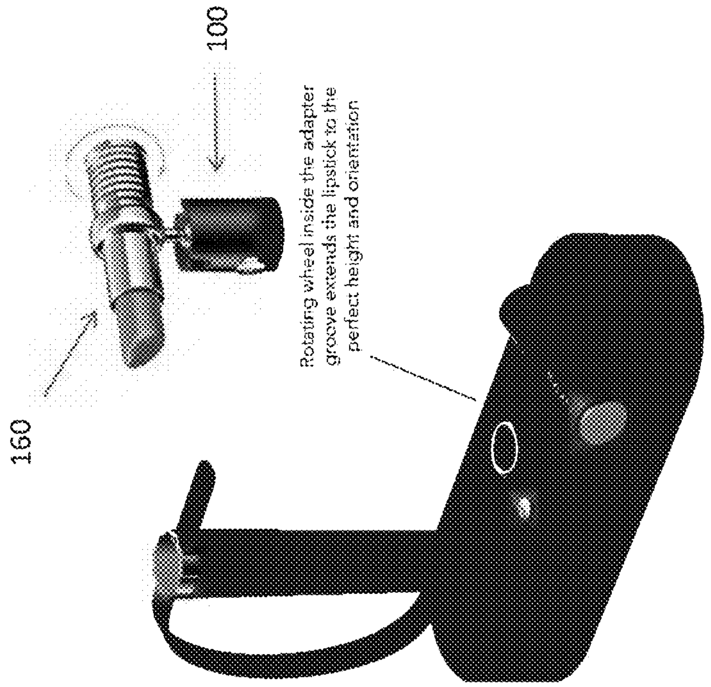
FIGS. 22A, 22B, and 22C show an embodiment in which an adapter with lipstick can be controlled to be extended or shortened within the securement apparatus, according to an embodiment.

As shown in FIG. 22A the adapter 100 holds lipstick tube 160. While the adapter can be stored in the securement apparatus without any cosmetic applicator, the adapter can be stored in the securement apparatus with the lipstick tube still inserted therein. Additionally, a rotating wheel inside the securement apparatus can grip the end of the lipstick tube and operate to rotate the tube within the securement apparatus so the lipstick tube will be at the optimal height and orientation before the user removes the adapter to be inserted into the motion stabilizing device.

Figure 22B:
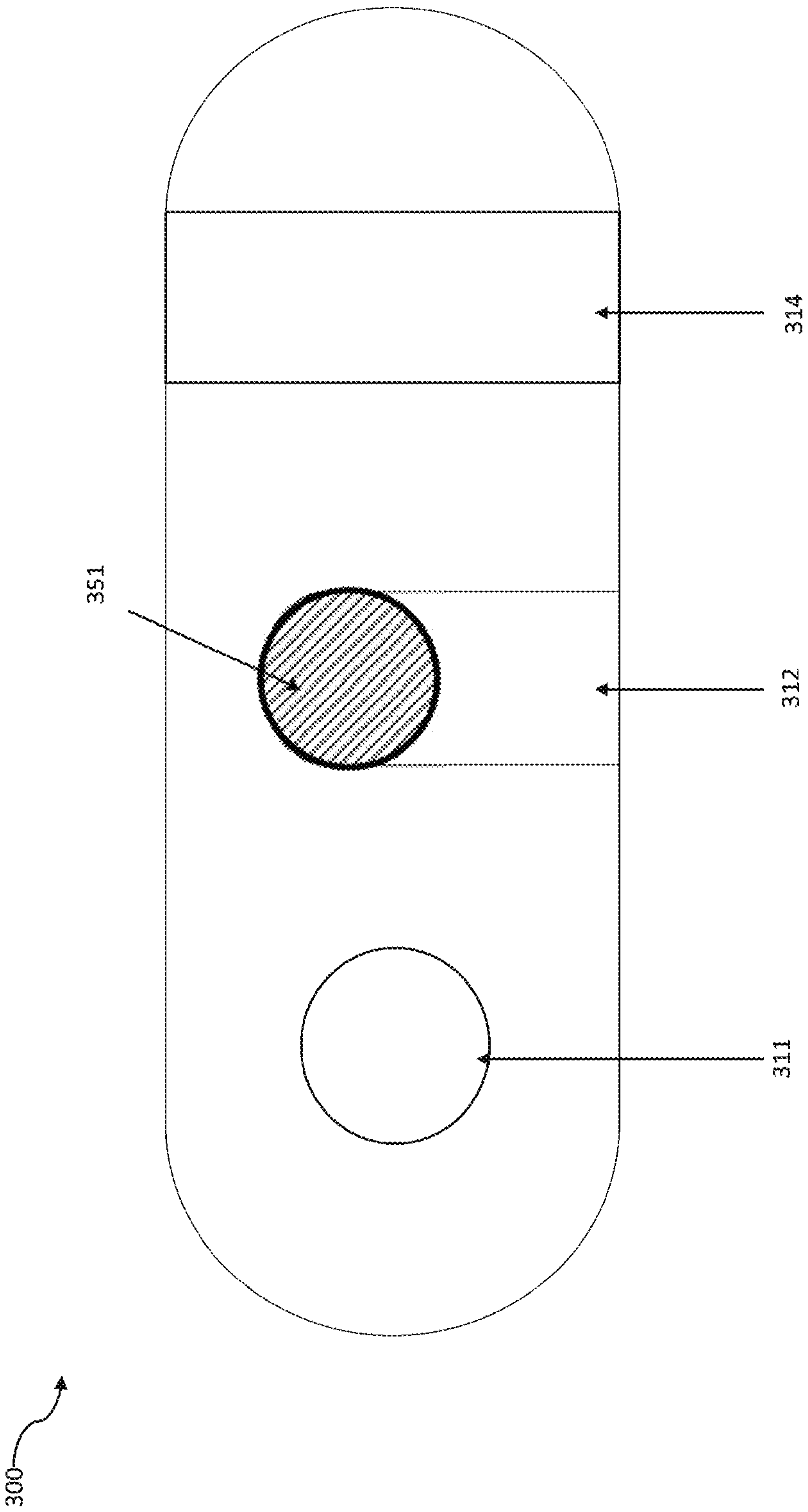

FIG. 22B shows an overhead view of the securement apparatus 300. As discussed above, the securement apparatus 300 includes chambers 311, 312, and 314. The chamber 312 holds the adapter 100 as shown in FIG. 22A. In this embodiment, chamber 312 further includes insertion hole 351 which allows for insertion of the lipstick tube when the lipstick tube is coupled with the adapter 100.

Figure 22C:
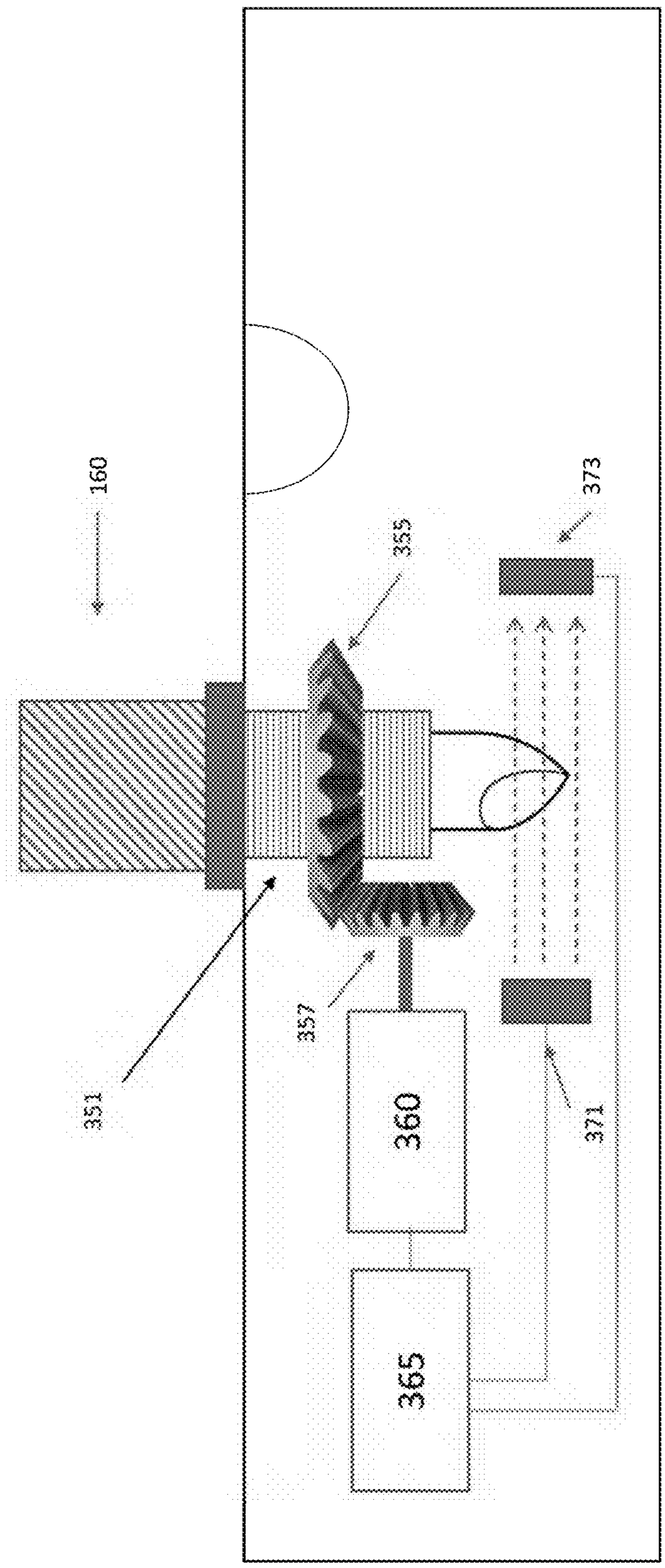

FIG. 22C shows a transparent side view of the securement apparatus 300 where it can be seen how the lipstick tube 160 is inserted through the insertion hole 351. As the lipstick tube is inserted into the insertion hole 351, it is further inserted through a bevel gear 355. The bevel gear 355 is rotated by a motor gear 357 which is connected to motor 360. The motor 360 is connected to a CPU 365 which provides control signals to the motor 360.

Figure 23B:
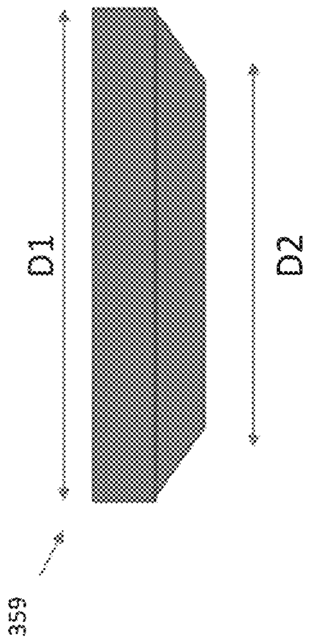
FIGS. 23A and 23B show additional details related to a bevel gear, according to an embodiment.
Figure 23A:
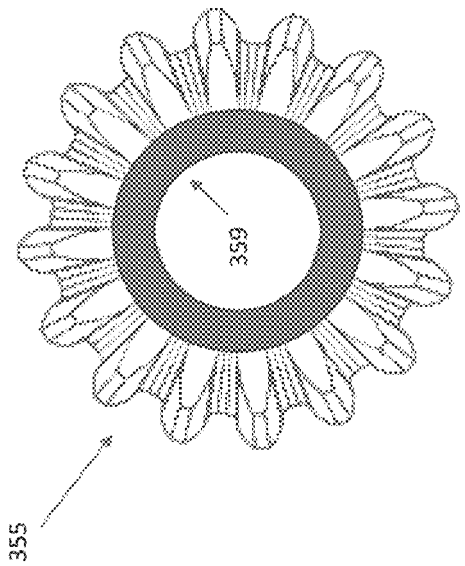

FIGS. 23A and 23B show additional details related to the bevel gear 355. FIG. 23A shows an overhead view of the bevel gear 355 through which the lipstick tube 160 is inserted. The bevel gear includes a beveled seat gasket 359 that is attached to the inner circumference of the bevel gear. The same type of beveled seat gasket is also utilized in the bevel gears 361 and 362 described above.

FIG. 23B shows a side view of the beveled seat gasket 359. It can be seen that the beveled seat gasket includes a wider first diameter D1 at a highest point, and a narrower second diameter D2 at a lowest point. The design of the beveled seat gasket will allow the lipstick tube 160 to be inserted a fixed amount within the securement apparatus 300. The beveled seat gasket is made of a material with a firm grip, such as rubber, so that the turning of the beveled gear 355 will translate to turn a rotatable portion of the lipstick tube, and thus provide for extension or shortening of the lipstick tube.

Returning to FIG. 22C, the securement apparatus further includes an LED emitter 371 and an photo sensor 373. This pair operates as an optical encoder of the transparent type that detects when then emitted light (which is emitted from a plurality of sources) is interrupted by extension of the lipstick. When the lipstick is not extended a predetermined amount, there will be no interruption of any of the light rays emitted by the LED emitter. As the lipstick is controlled to be extended by the bevel gear 355, it will interrupt light rays emitted by the LED emitter sequentially, which is detected by the photo sensor 373. The number of light rays interrupted are communicated back to the CPU 365, which can thus detect an extension amount of the lipstick tube.

It can be seen by the structure shown in the above figures that the following elements be controlled/adjusted and/or detected.

Extension amount of the lipstick

Orientation of the "chisel" on the lipstick

Detection of how much lipstick is left inside tube

Figure 24A:
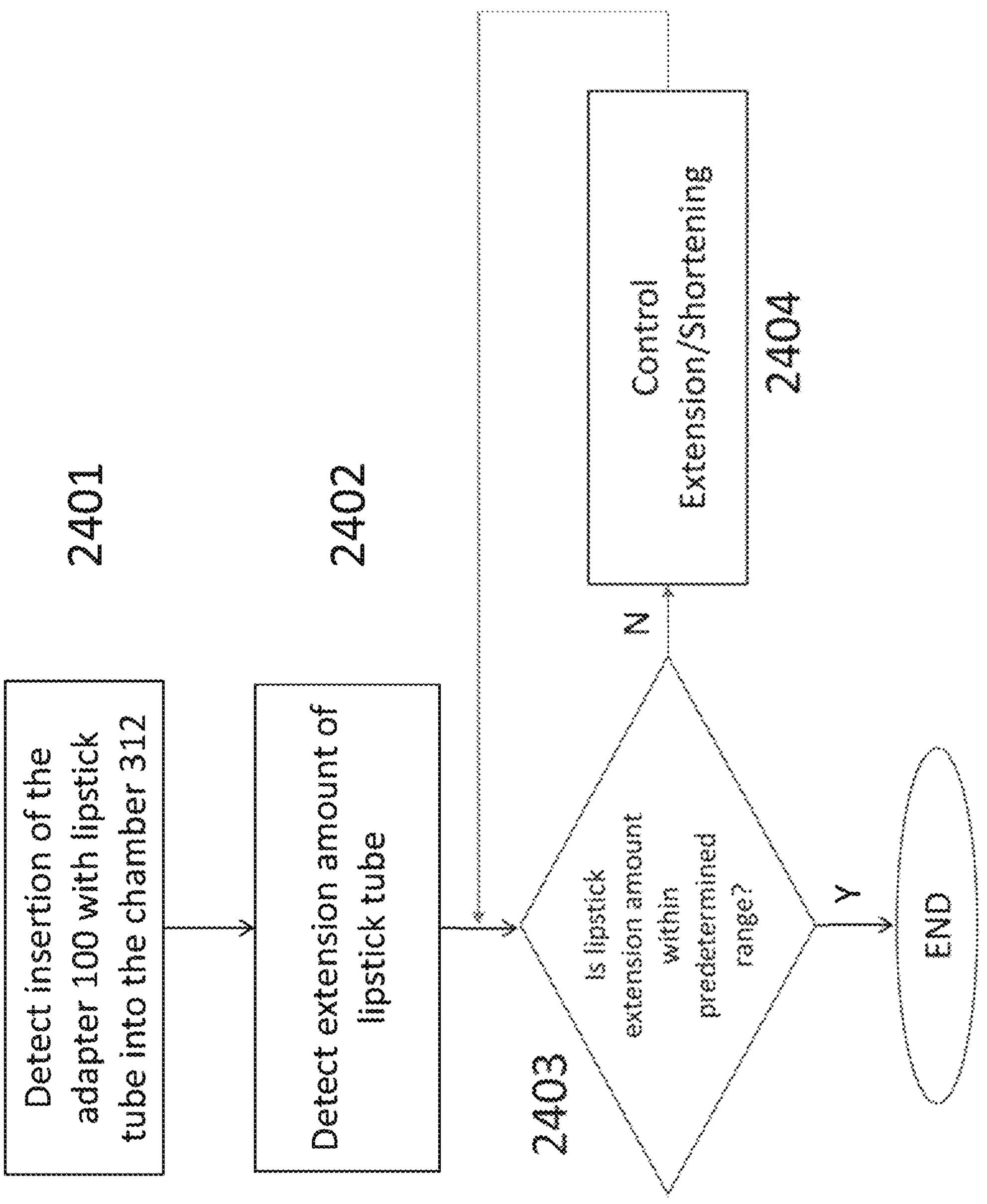
FIGS. 24A and 24B show a flowchart of a process performed by the securement apparatus related to detecting an amount of lipstick in a lipstick tube and controlling extension of the lipstick tube, according to an embodiment.

FIG. 24A shows a flowchart of a process performed by the securement apparatus 300 for controlling extension of the lipstick tube, according to an embodiment. In step 2401, the securement apparatus 300 detects insertion of the adapter 100 with the lipstick tube into the chamber 312. This detection may be based on the protocols for communication of the type of adapter described above. In step 2402, the CPU 365 detects the extension amount of the lipstick tube based on the interruption of the light rays described above. Based on the number of light rays that are interrupted, the CPU then determines if the lipstick extension amount is within a predetermined range in step 2403. If the lipstick is not within the range, then control is performed at step 2402 to extend or shorten the extension of the lipstick tube until the outcome of step 2403 is that the lipstick is within the range, at which time the process ends.

Figure 24B:
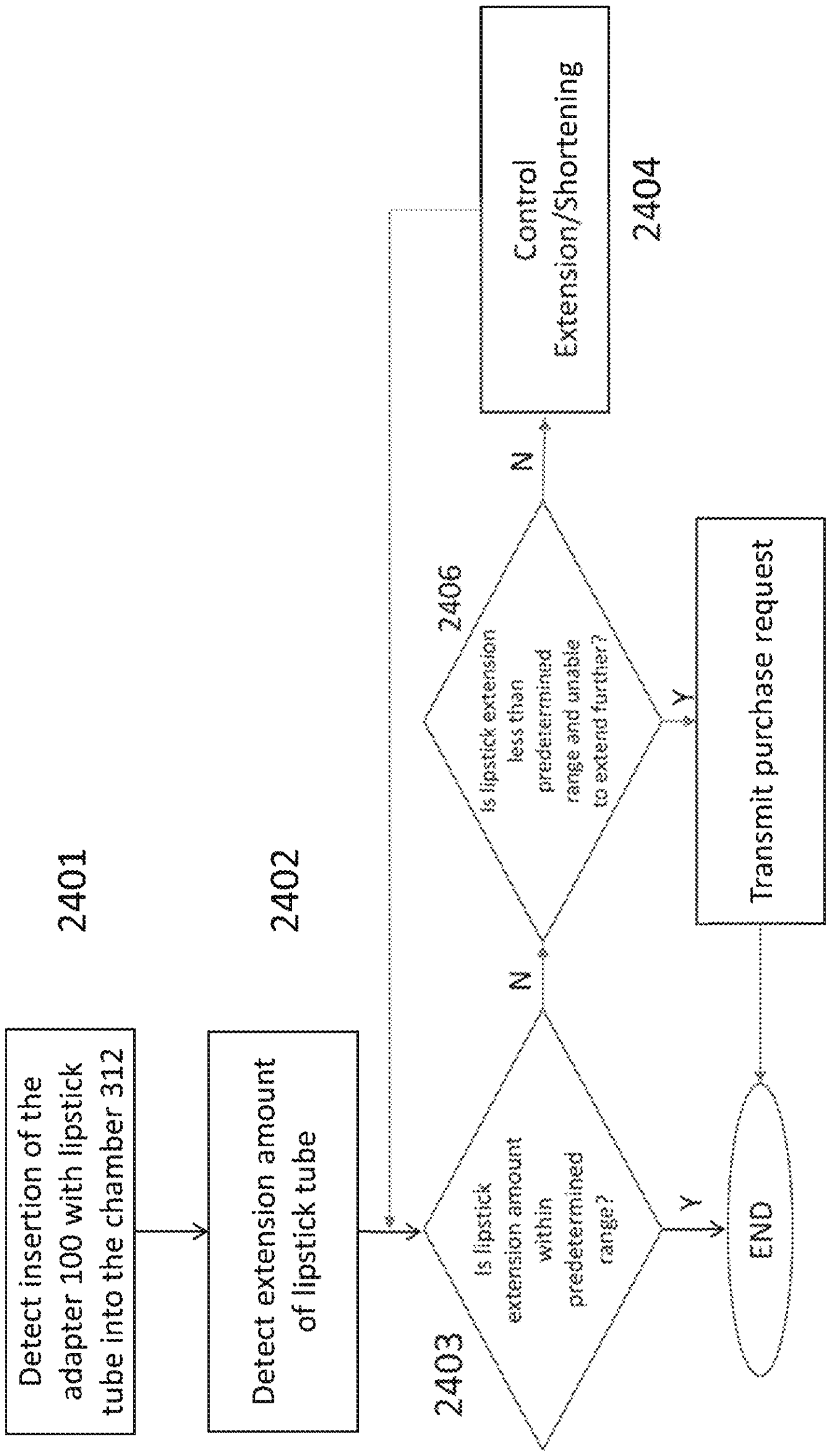

FIG. 24B shows a subroutine that is based on the detection of an extension of an amount of lipstick. It first should be noted that the CPU 365 is configured to connect to an external server via the Internet (or via a user's mobile device). In FIG. 24B, if the lipstick amount is not within the predetermined range in step 2403, it is further determined in step 2406 whether the lipstick extension amount is less than the predetermined range and unable to be extended any further. If so, this means the lipstick is tube is almost finished and the CPU 365 transmits a purchase request in step 2408 to an external server (such as an online cosmetic retailer) for new lipstick.

Heating and Cooling system

Figure 25:
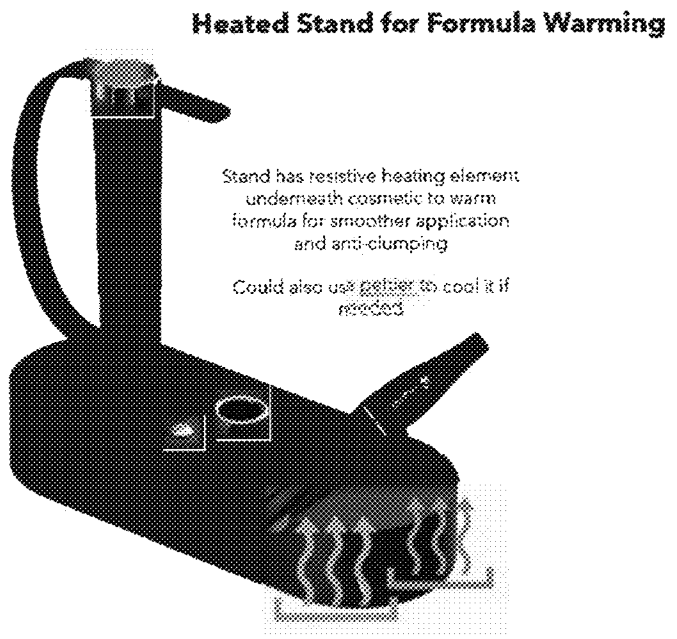
FIG. 25 shows that the securement apparatus (stand) can have an additional feature for heating or cooling, according to an embodiment.

In an embodiment, FIG. 25 shows that the securement apparatus (stand) can have an additional feature for heating or cooling a cosmetic for smoother application. In particular, with mascara, heating can be used to avoid clumping of the mascara.

Figure 26:
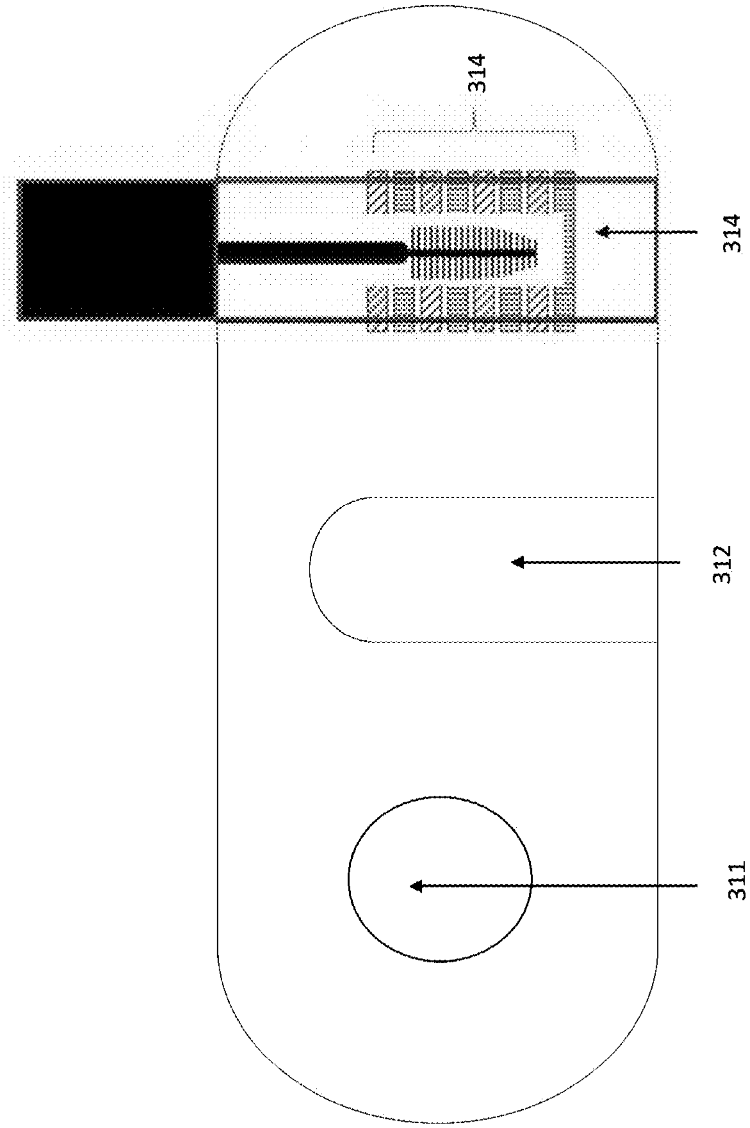
FIGS. 26 and 27 show transparent views of the securement apparatus with the heating/cooling system, according to an embodiment.
Figure 27:
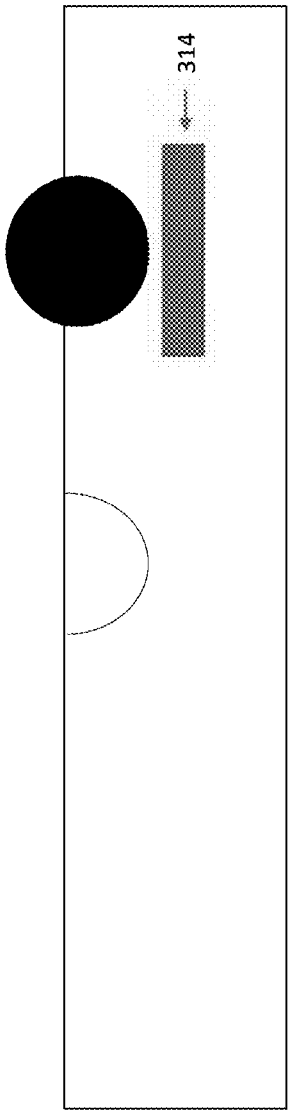

FIGS. 26 and 27 show transparent views of the securement apparatus with the heating/cooling system. FIG. 26 is an overhead view of the securement apparatus showing chambers 311, 312, and 314 which were described above. FIG. 27 is a side view.

As shown in FIG. 26, chamber 314 holds a mascara container, which is made transparent to illustrate the positioning of the mascara wand within the container. It can be seen in both FIGS. 26 and 27 that a heating/cooling system 385 is disposed beneath the mascara container.

Figure 28:
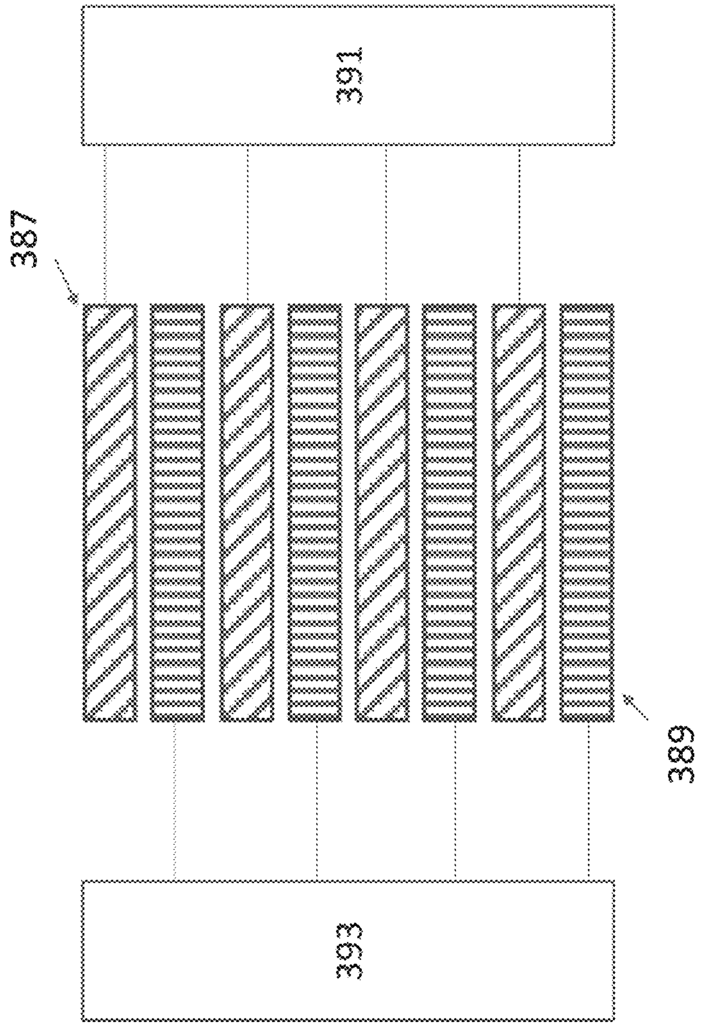
FIG. 28 shows a closer view of the heating/cooling system, according to an embodiment.

FIG. 28 shows a closer view of the heating/cooling system 385. In order to provide the option of either heating or cooling the same overall area of the mascara container, the heating/cooling system is arranged such that heating elements 387 and cooling elements 389 are disposed in an alternating sequence along the length of the mascara container. The heating elements 387 are controlled by controller 391, and the cooling elements 389 are controlled by the controller 393.

The heating elements may be resistive heating elements as is understood in the art and made of a ceramic material. The cooling elements may be mini peltier cooling elements as known in the art. Temperature sensors are integrated with the heating/cooling system 385 to determine temperature, and the temperature is adjusted to a predetermined amount to ensure smooth application of the cosmetic. In one embodiment, the mascara container may be heated to a temperature of 100° F. approximately five minutes before use.

The temperatures described above are examples are not limited to specific temperature targets, as long as the temperature reduces viscosity of mascara to reduce clumping. This could also be used for lipstick to achieve an ideal hardness of the lipstick material so that it easily deposits onto the lips without too much pressure, but does not get too soft such that it smears too easily from its general shape. Additionally, this could be used for lip gloss, eyebrow glue, concealer, etc. Effectively any cosmetic that has some level of viscosity to it (not dry) to be controlled for optimal application viscosity. This can be extended to any time of cosmetic that a user could utilize this handle to achieve accuracy and ease of application even with disabilities.

In an embodiment, the system described above utilizes an external mobile device, such as a smartphone, to provide for learning and gesture compensation. An application executed by a smartphone scans the lip size, shape and contours in a selfie image captured by the user to prepare for precise application movements. The application also learns and understands the contours of the user with this scan. The application will initiate a feedback loop by having the user take “selfie” pictures before and after a cosmetic application session. This step provides a measurement on the application, reads the before and after to signal the device how it could have moved better (less compensation vs. more compensation). The smartphone provides a realtime mirror which provides feedback for the device in realtime to adjust compensation level and angles. A more detailed approach to the calibration feature will be described below.

Figure 29:
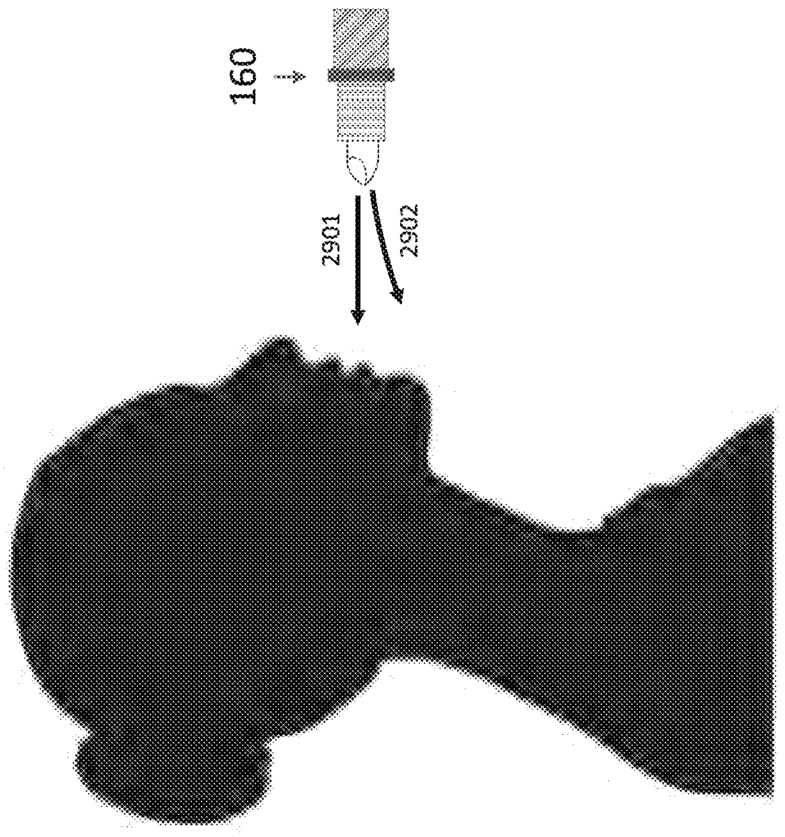
FIG. 29 illustrates a problem that is going to be solved by the present embodiment for a user of the system.

FIG. 29 illustrates a problem that is going to be solved by the present embodiment for a user of the system. In FIG. 29, there is a cosmetic applicator 160 (lipstick in this example) which the user is going to bring toward their face. A target trajectory for bringing the lipstick tube toward the user’s face is shown by line 2901. However, due to variations in the user’s unintentional movements, even with the motion stabilizer, the actual trajectory may be deviated as shown by line 2902. This can lead to mistakes in the cosmetic application process, resulting in stray marks or misaligned make-up.

Figure 30:

FIGS. 30-31 shows a manner in detecting when the motion stabilizer needs to be re-calibrated. As shown in FIG. 30, within the application, the user may take a selfie image of themselves. The application then utilize facial recognition software to scan the face and identify application target area (i.e. lips or eyes). In the present example, the application target area is the user’s lips, and FIGS. 30A-30C show different examples of states of the user’s lips when taken by a selfie image.

Figure 31A:
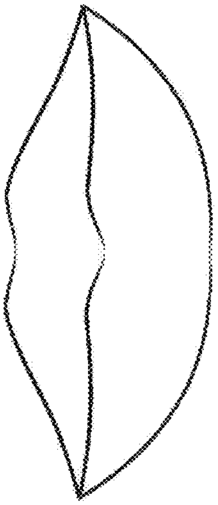
FIGS. 30 and 31A-31C show a manner in detecting when the motion stabilizer needs to be re-calibrated, according to an embodiment.
Figure 31B:
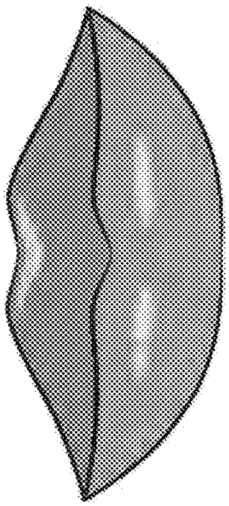
Figure 31C:
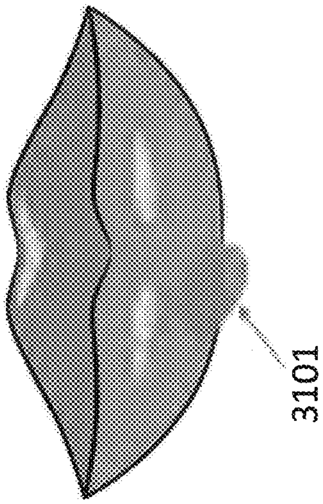

FIG. 31A shows the lip region when the user has not yet applied any lipstick and is considered a “before” picture relative to the overall process. The application will detect the boundaries of the user’s lips at this point and in particular the contours of the border of the lip region. FIG. 31B shows the lip region when the user has applied the lipstick without any detectable mistakes. In this case, the application detects that the lipstick has been applied up to and not past the boundary of the lip region. FIG. 31C shows the lip region when the user has made a detectable mistake such as the area shown by 3101. The application detects that this area 3101 of applied lipstick is beyond the boundary of the lip region.

If a mistake is detected such as shown in FIG. 31C, the application software is configured to measure percentage error between target application and actual application, and recognize where the error is made with regards to location on lips as well as during what movements the device was making at that time.

Figure 32A:
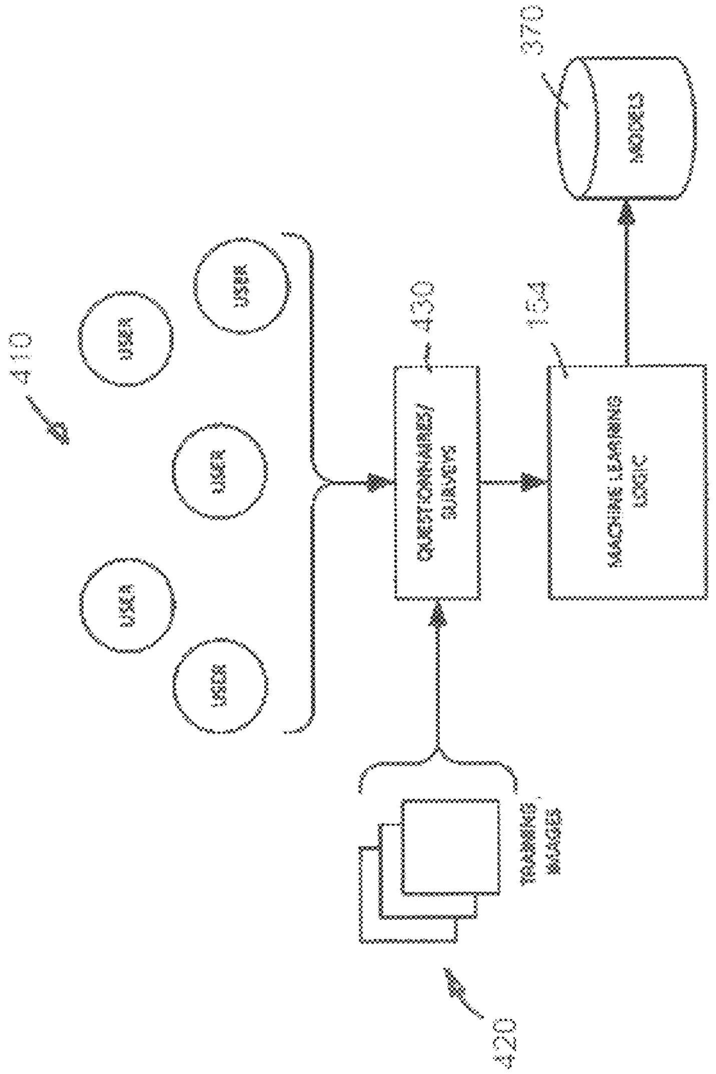
FIG. 32A-32B illustrate how machine learning can help detect when an error has occurred, according to an embodiment.

Aside from detecting if a cosmetic has gone past a boundary, FIG. 32A is a diagram shown how machine learning can help detect when an error has occurred. During training, users 410 are presented a set of training images 420 over which they are asked to characterize if an error has occurred with make-up application on images of various people. In one embodiment, an error scale is used with which users can rate magnitude of an error. For example, each of users 410 (over time) are presented a large number of images and is walked through a set of questions regarding features of the person in the image. Using the scale, each user 410 is asked to select a magnitude of an error in the make-up application. The answers to the questions may serve as labels used for training machine language logic 154.

Figure 32B:
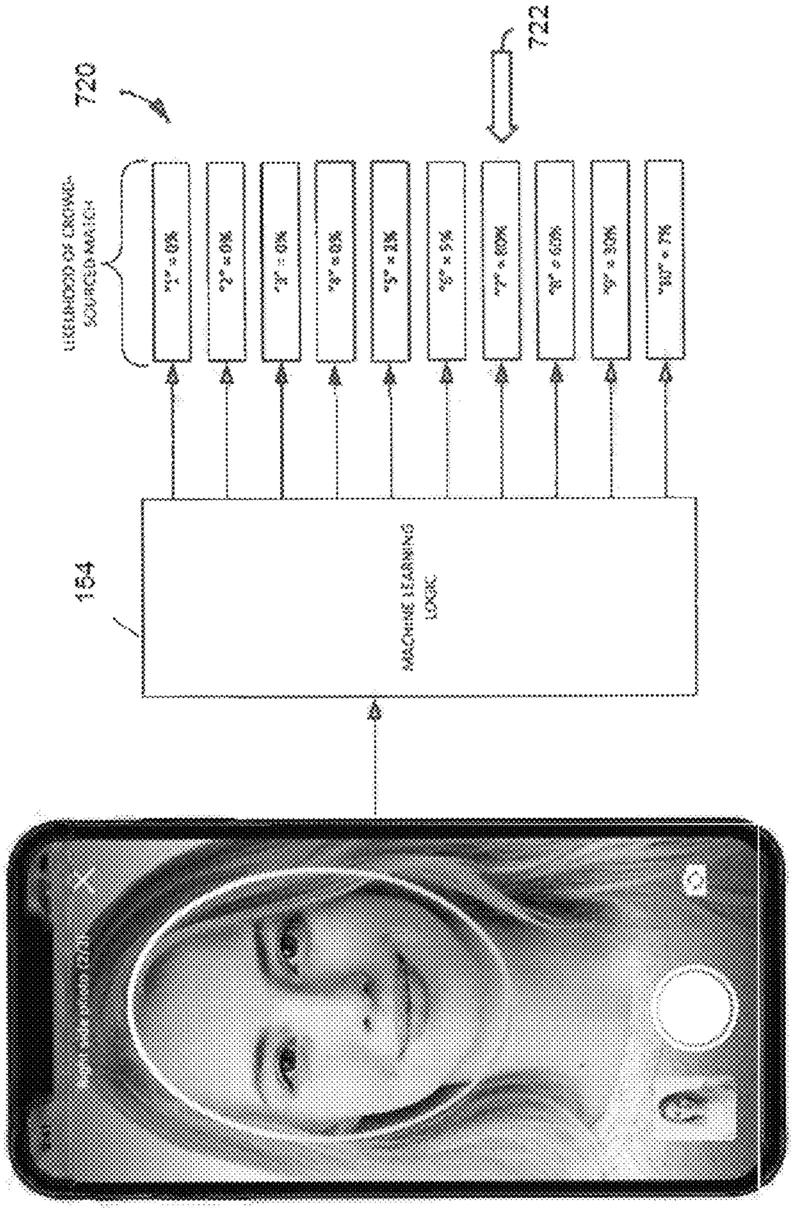

FIG. 32B illustrates an example test operation in accordance with the crowdsourced training discussed above. A test image 710, i.e., a user’s own image, may be presented to machine learning logic 154, which analyzes the image per the models trained on the crowdsourced data 720. As illustrated in the figure, machine learning logic 154 estimates that 80% of people surveyed would rate the user’s error magnitude in make-up application as a type #7 as indicated at 722. Accordingly, machine learning logic 154 may use the error magnitude type #7 in determining if an error occurred that requires further analysis.

Figure 32C:
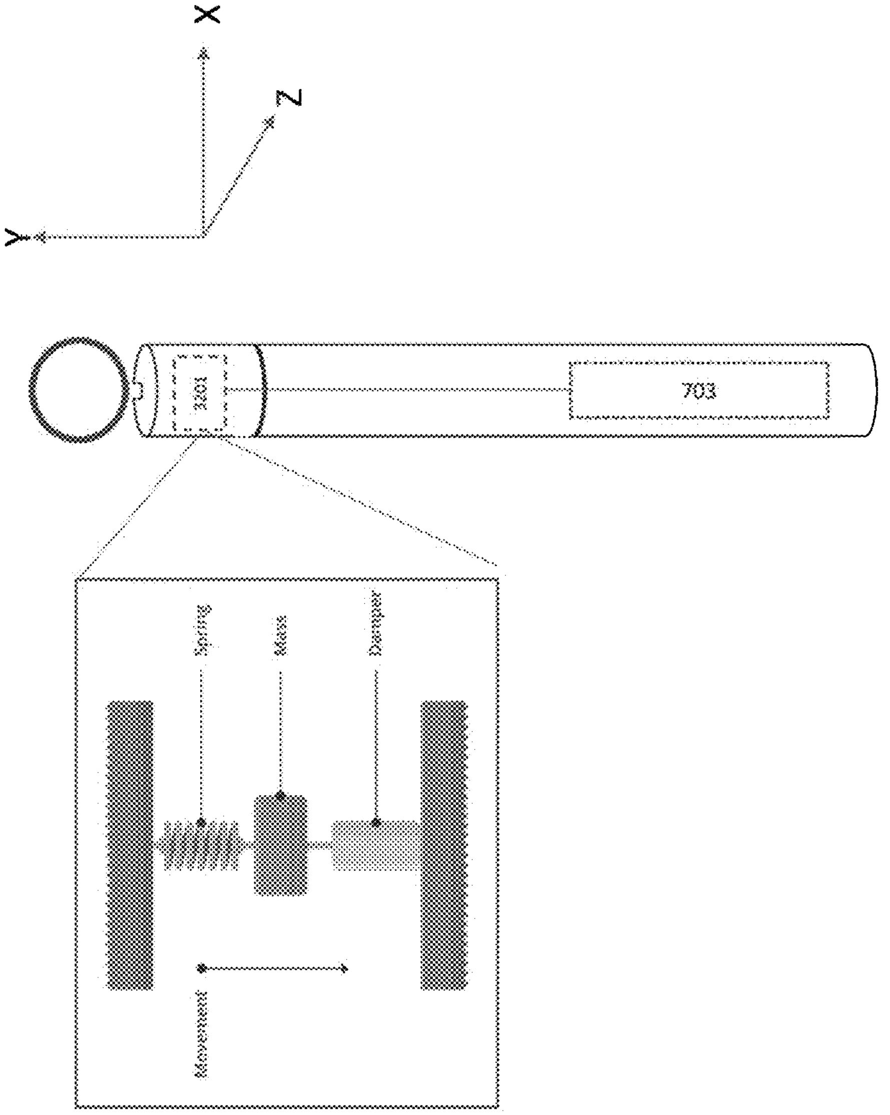
FIG. 32C shows an accelerometer in the motion stabilizer, according to an embodiment.

For instance, the motion stabilizer utilizes an inertial measurement unit (IMU), a gyroscope, or an accelerometer on the adapter itself or the upper portion (i.e., the stabilized portion) of the motion stabilizer device of the to understand these locations/orientations. FIG. 32 shows an example where an accelerometer 3201 is provided within the in the handle portion of the motion stabilizer device and is connected to PCBA 703. The accelerometer includes a mass, damper, and spring mechanism, as understood in the art, and measures movement in the X, Y, and Z directions in a three-dimensional space.

Figure 33A:
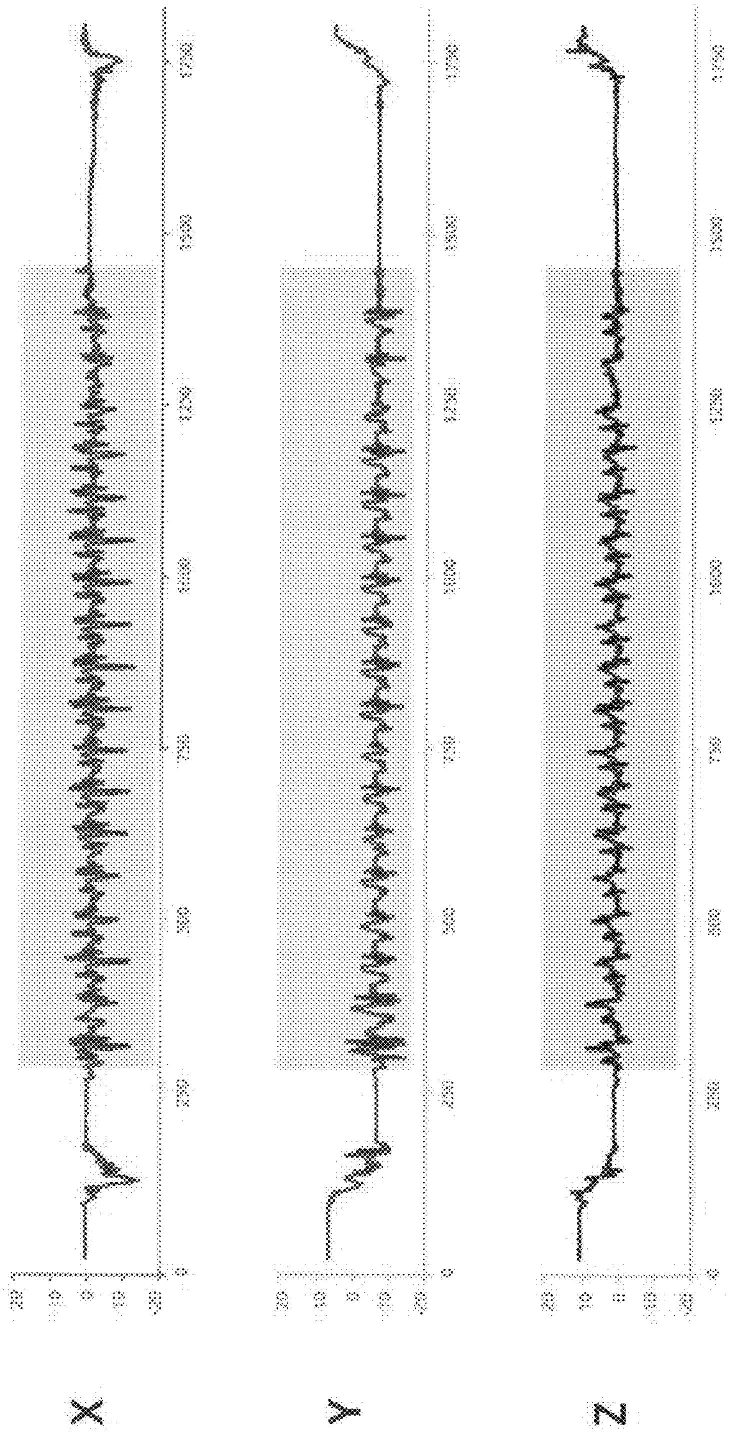
FIGS. 33A-33B show example measurements taken by the accelerometer in the X, Y, and Z directions, according to an embodiment.

FIG. 33A shows example measurements taken by the accelerometer in the X, Y, and Z directions during normal movement of adapter, where during a session of applying the lipstick, the adapter will be maintained at a consistent level without significant deviation.

Figure 33B:
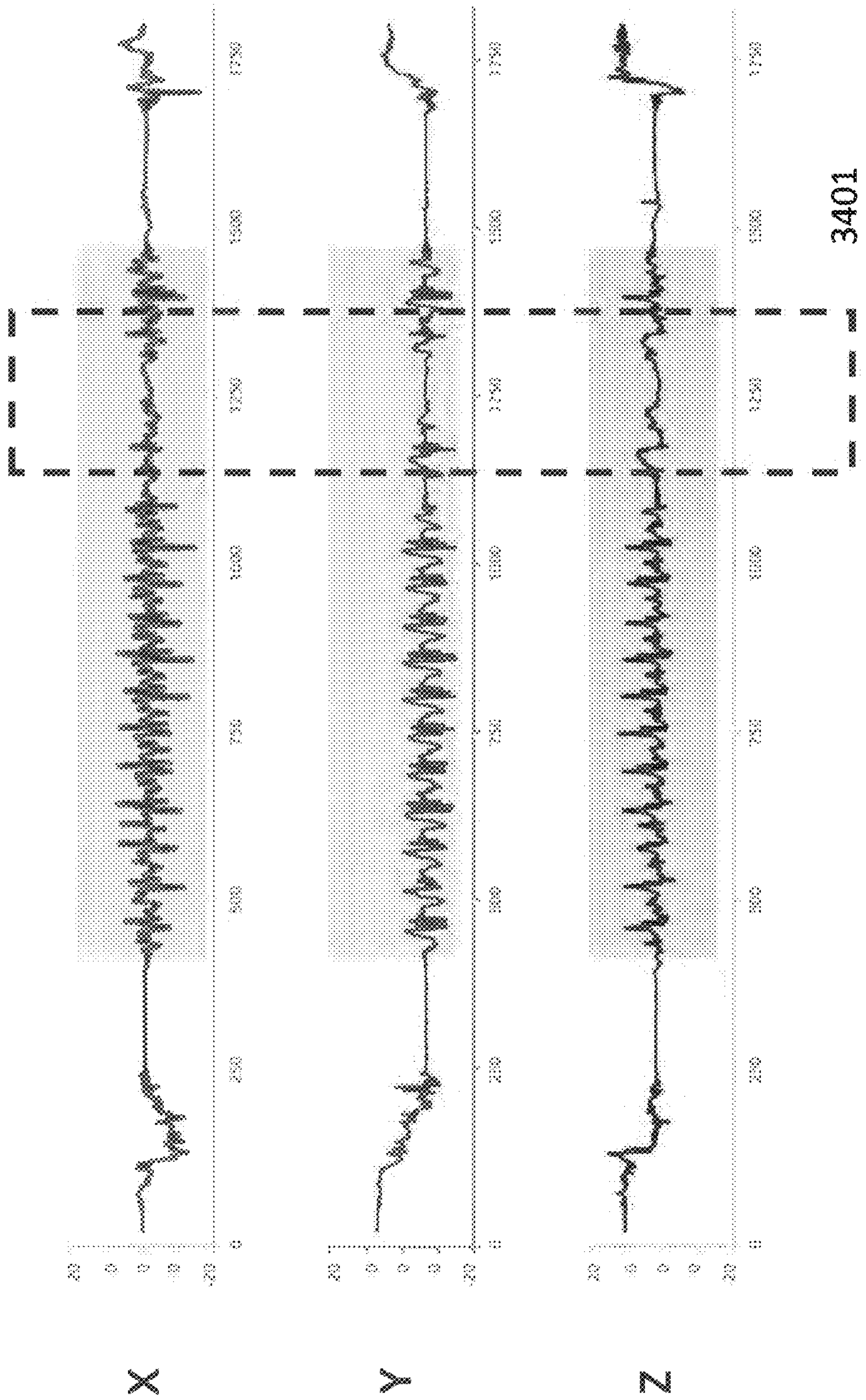

FIG. 33B shows a scenario in which at a time region indicated by 3401 indicates a deviation in the measurements of the X, Y, and Z sensors in comparison to the normal movement of the adapter. Based on a percentage error, a direction of the error, and a timing of the error, the application software will learn how to better compensate with different gestures, different speeds, etc.

For instance, if the accelerometer measurements show that the cosmetic applicator is drifting in a downward direction, as shown in FIG. 29 above, then the motion stabilizer may counter by stabilizing the cosmetic application in an upward direction.

Software could provide additional recommendations to user on how to better handle the device if possible for best results.

In certain cases, the accelerometer will not clearly show an error based on an anomaly at a specific time period. However, data may have a signature pattern that is associated with a type of error. In this scenario, a deep learning model is helpful to recognize how to associate a remedy with a pair of the type of make-up error shown in the selfie image and the motion sensor data.

Figure 34A:
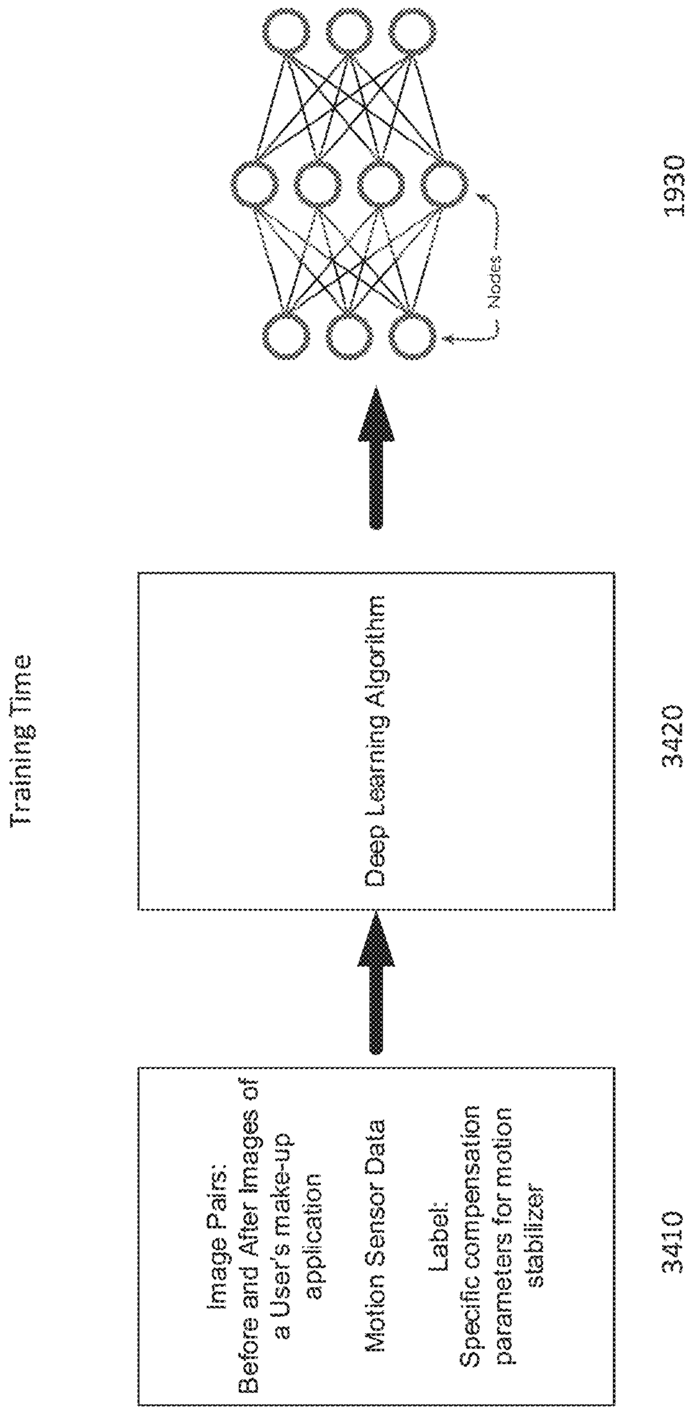
FIGS. 34A-34B show a deep learning model recognize show to associate a remedy with a pair of the type of make-up error shown in the selfie image and the motion sensor data, according to an embodiment.

In FIG. 34A, training is performed for the deep learning model. The inputs are provided at stage 3410, where pictures (which could be the picture selfies described above) are input along with motion sensor data (such as the accelerometer data) and a label. In this case, the "label" give to the inputted data is the compensation parameters used in the motion stabilizer that remedies the error in the make-up application process.

The inputs are provided to a deep learning algorithm in step 3420. The deep learning algorithm used may be based on available software as known in the art, such as Tensorflow, Keras, Mxnet, Caffe, or Pytorch. The result of the labeled training will be a neural network at step 3430. The neural network created includes nodes of each layer are clustered, the clusters overlap, and each cluster feeds data to multiple nodes of the next layer.

Figure 34B:
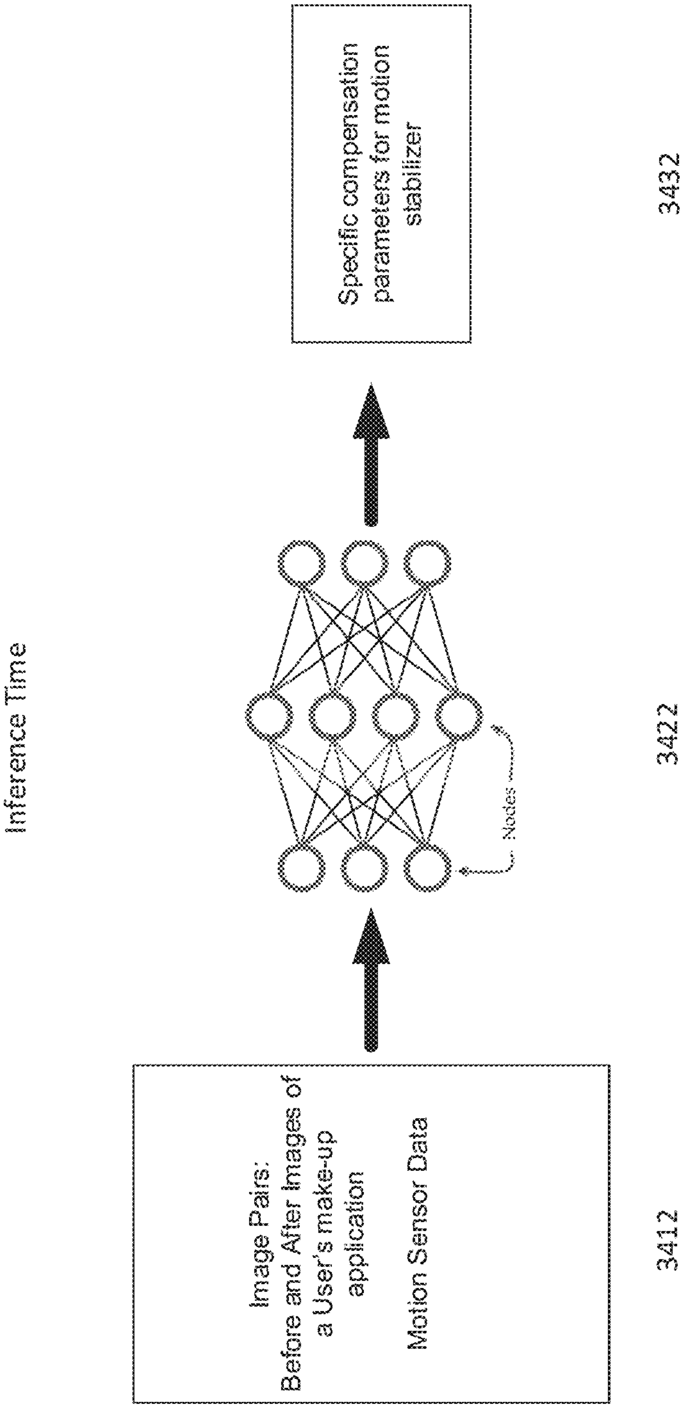

FIG. 34B shows the usage of the deep learning model after training has reached an adequate level. This is referred to as "inference time" since recommendation will be inferred from input data without a label. It can be seen that the input stage does not include a label. Additionally, at step 3412, the image pair includes the user's inputted selfie image and the motion sensor data. These inputs are fed to the neural network at step 3422, which will provide an output at step 3432 of the compensation parameters used in the motion stabilizer that remedies the error in the make-up application process Therefore, the deep learning process of FIGS. 34A-34B allow machine logic to determine correlations between the user's selfie image and motion sensor data in order to output motion compensation parameters for preventing the error in future sessions.

Figure 35:
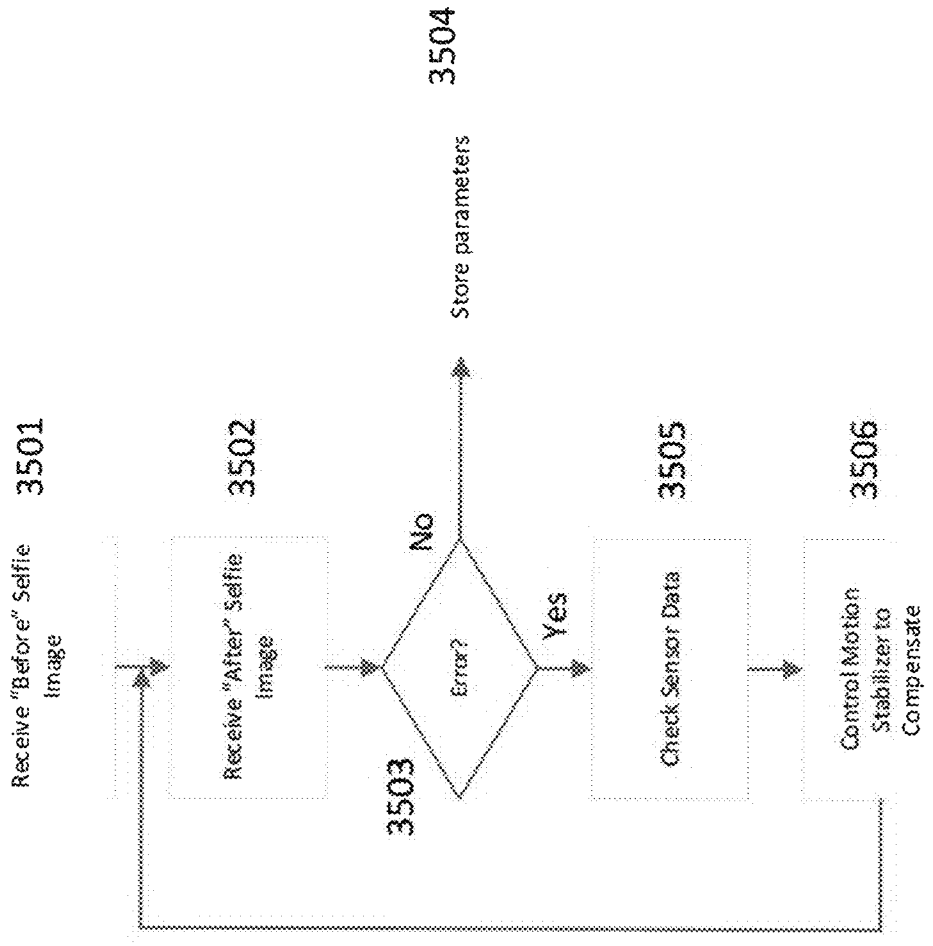
FIG. 35 shows a flowchart for compensating for deviations in the movement of the adapter, according to an embodiment.

FIG. 35 shows a flowchart for compensating for deviations in the movement of the adapter based on the above description. In step 3501, the application receives a selfie image captures by the user without any cosmetic applied, and this represents that "before" image. In step 3502, the application receives a selfie image captured by the user after applying the cosmetic, and this represents the "before" image.

In step 3503, the application analyzes the image to determine if there was an error in applying the cosmetic. In other words, the application is analyzing to determine if the user has inadvertently missed the target location with the cosmetic.

There are different methods of performing image analysis. One method is to detect features in an image that indicate the boundaries of the user's natural features and to determine if the cosmetic crosses such a boundary. For instance, a boundary of a user's natural features may be detected based on threshold contrasting pixel values at the boundaries. To facilitate this step, the white balance image may be optimized such that the white balance of the picture to facilitate the detection dark versus light contrast. Specific techniques to detect facial features are understood in the art and described in detail in at least U.S. Patent Publication No 2007/0154096A1 and PCT patent Publication WO2011074014A2, which are herein incorporated by reference.

Another method as was described above is to use deep learning or machine learning to train a model to determine when a cosmetic has not been applied correctly. In this embodiment, the system implements one or more convolutional neural networks (CNNs), the models for which may be trained using open source datasets or crowdsourced data sets, as explained below. Other machine learning techniques may be used in conjunction with the present invention including, but not limited to, decision tree learning, association rule learning, artificial neural networks, deep learning, inductive logic programming, support vector machines, clustering, Bayesian networks, reinforcement learning, representation learning, similarity and metric learning, sparse dictionary learning, genetic algorithms, rule-based machine learning and learning classifiers. Additional techniques described in U.S. Pat. Nos. 8,442,321, 9,015,083, 9,536,293, 9,324,022, and U.S. PG Publication No. 2014/0376819 A1, all of which are incorporated herein by reference, may be used with the present invention.

If there is no error at step 3503, then the current motion stabilizer settings are stored in the PCBA 703 as shown in step 3504.

However, if there is an error detected, then the process proceeds to step 3505, where the sensor data is checked from a motion sensor (such as an accelerometer) to determine where there is deviation from normal movement pattern in the sensor data (as described above.

In step 3506, based on the detected deviation found in the motion sensor data, control parameters are configured in the motion stabilizer to compensate for such deviation during next session. At that point, the process will loop back to step 3502 so that the parameters can be checked after the users' next session for applying the cosmetic.

In an alternative embodiment, the system may also provide compensation for potential deviations based on using a smartphone as a realtime mirror in selfie mode, and using recognition software, the application can detect when the applicator is going to miss an intended target.

Figure 36:
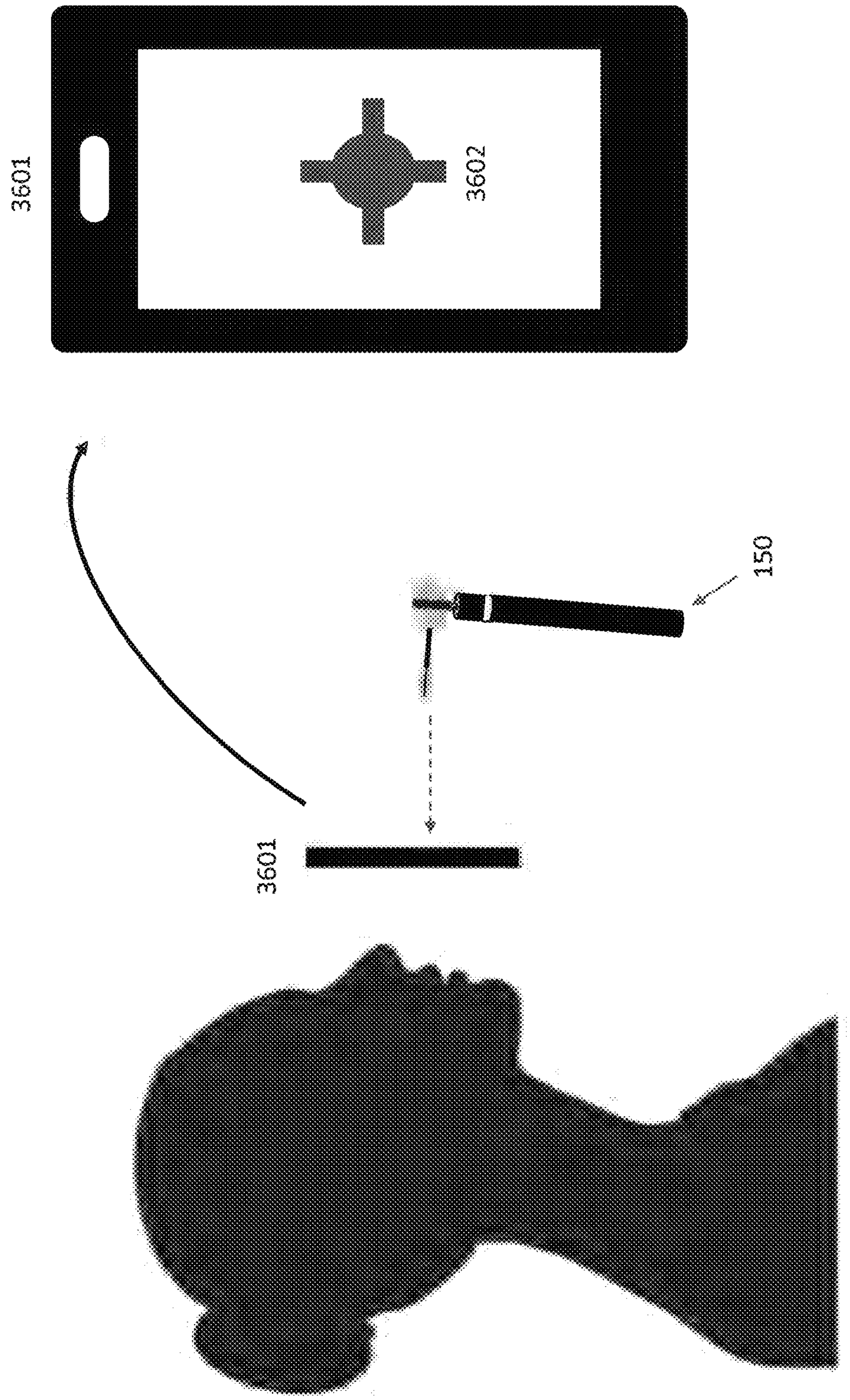
FIG. 36 illustrates a method to initially calibrate a user's tendency to deviate from a target spot when using the motion stabilizer, according to an embodiment.

While a user's difficulties to contact a cosmetic application on a target area can be detected based on the above process, FIG. 36 illustrates a method to initially calibrate a user's tendency to deviate from a target spot when using the motion stabilizer 150. FIG. 36 depicts a user that may hold a smartphone 3601 close to their face while looking into a mirror, with the display screen facing toward the mirror. An application on the smartphone 3601 displays a target region 3602. The user can attempt to land an unused or dummy cosmetic applicator on the display of the smartphone which has touchscreen capability. If the user has trouble hitting the target, then a natural deviation can be determined, and compensation parameters may be initially programmed to prevent errors from occurring in the future.

Figure 37A:
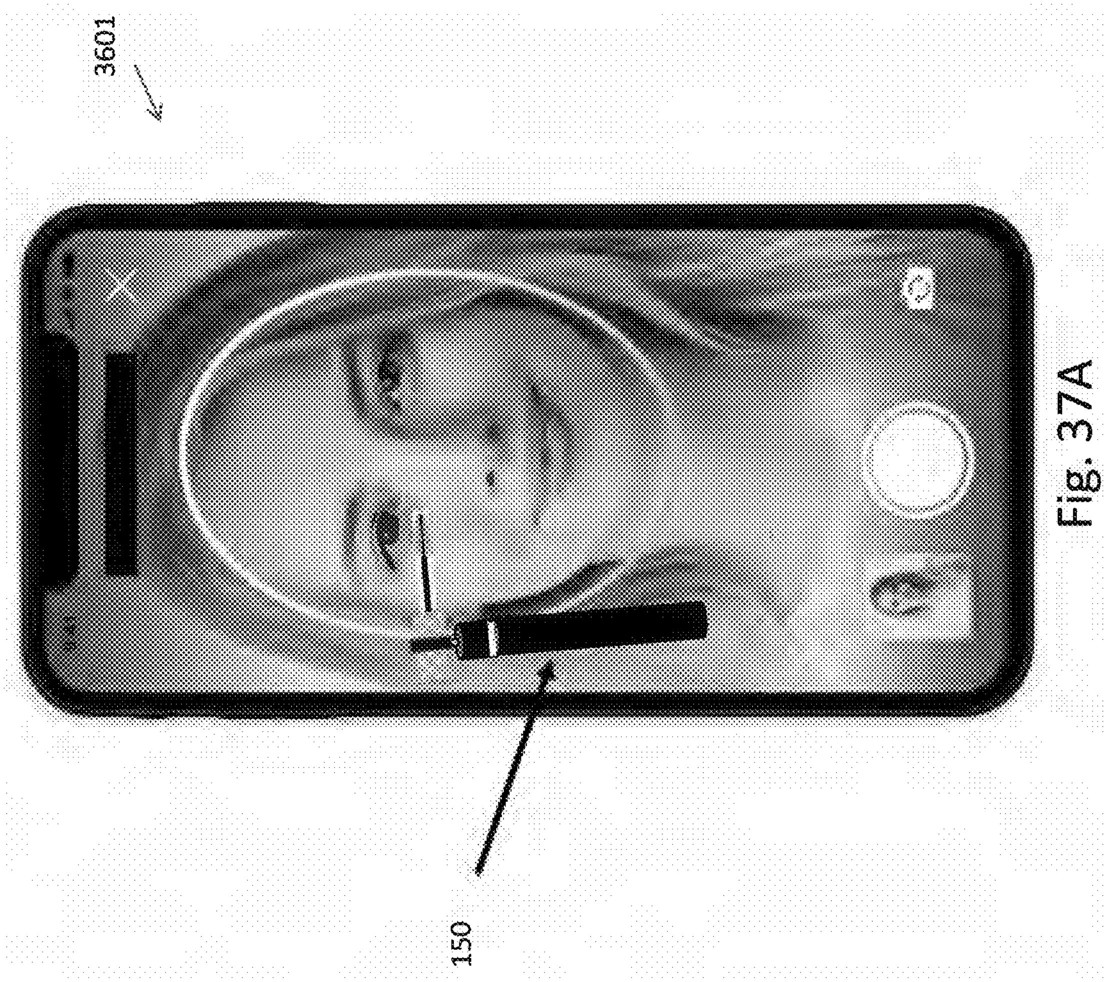
FIGS. 37A-37B depict a user that is using their smartphone as a realtime mirror in selfie mode while using the motion stabilizing device, according to an embodiment.

FIG. 37A depicts a user that is using their smartphone 3601 as a realtime mirror in selfie mode while using the motion stabilizing device 150. The application will detect both the facial features of the user and the position of the cosmetic applicator in the realtime image.

Figure 37B:
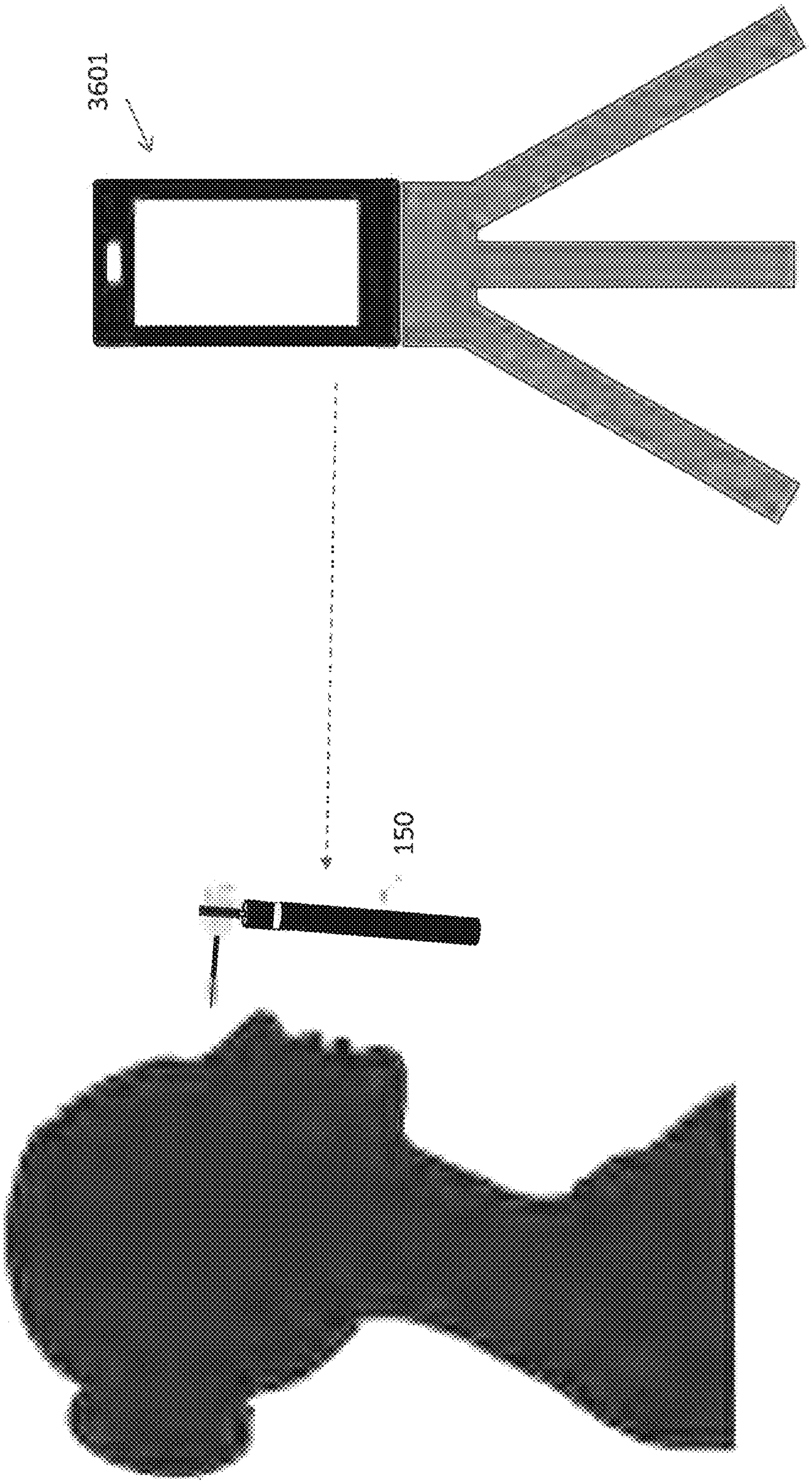

As shown in FIG. 37B, utilizing facial recognition software to map the dimensions of the lips or eyes (i.e. width and height), the user application on the smartphone 3601 would send this info via wireless communication to the motion stabilizer device to provide dimensional parameters to keep the cosmetic applicator on target.

Figure 38:
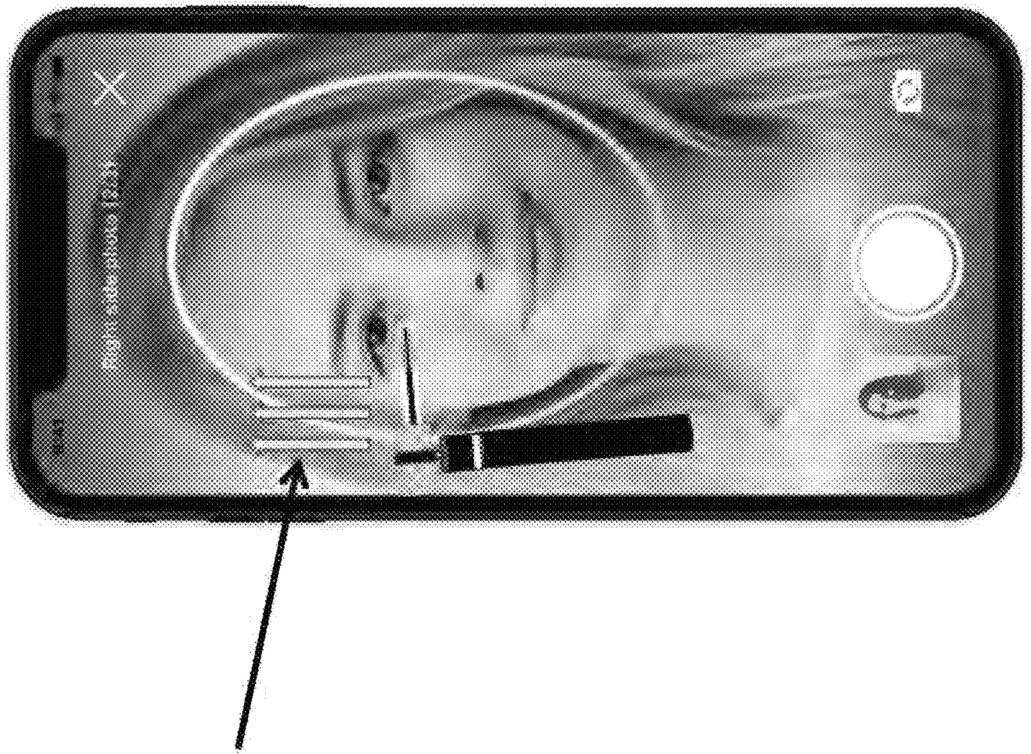
FIG. 38 shows that a user application can augment recommended device gestures over the face in image from camera.

As shown in FIG. 38, the user application can augment recommended device gestures over the face in image from camera. This mode can be used in combination with the intertial measurement unit (IMU) and/or gyroscope and accelerometer to understand real-time position of the device and adapter. For instance, FIG. 38 depicts arrows 3801 overlaid on the image to guide the user in a direction of the intended target. This overlaid indicator also notifies the user visually if the device/adapter move out of the bounds captured by the user app selfie scan.

Alternatively, the motion stabilizer device provides haptic feedback via vibration of the handle to communicate to the user that they are outside of the bounds of their lips/eyes and are therefore not applying the cosmetic accurately. This could specifically be used for visually impaired users that may not be able to clearly see the spatial limits of their lips or eyes In addition to this, there could also be haptic feedback provided in the occurrence that the user's unintended movements (i.e. tremors, shaking, spasms, etc.) are moving so far left to right or up and down that the device knows it will be impossible for itself to sufficiently compensate for these movements while staying in bounds of the mapped lip/eye application region. This vibration feedback could be a different pattern or intensity in order to discern from the other vibration feedback discussed above.

Figure 39:
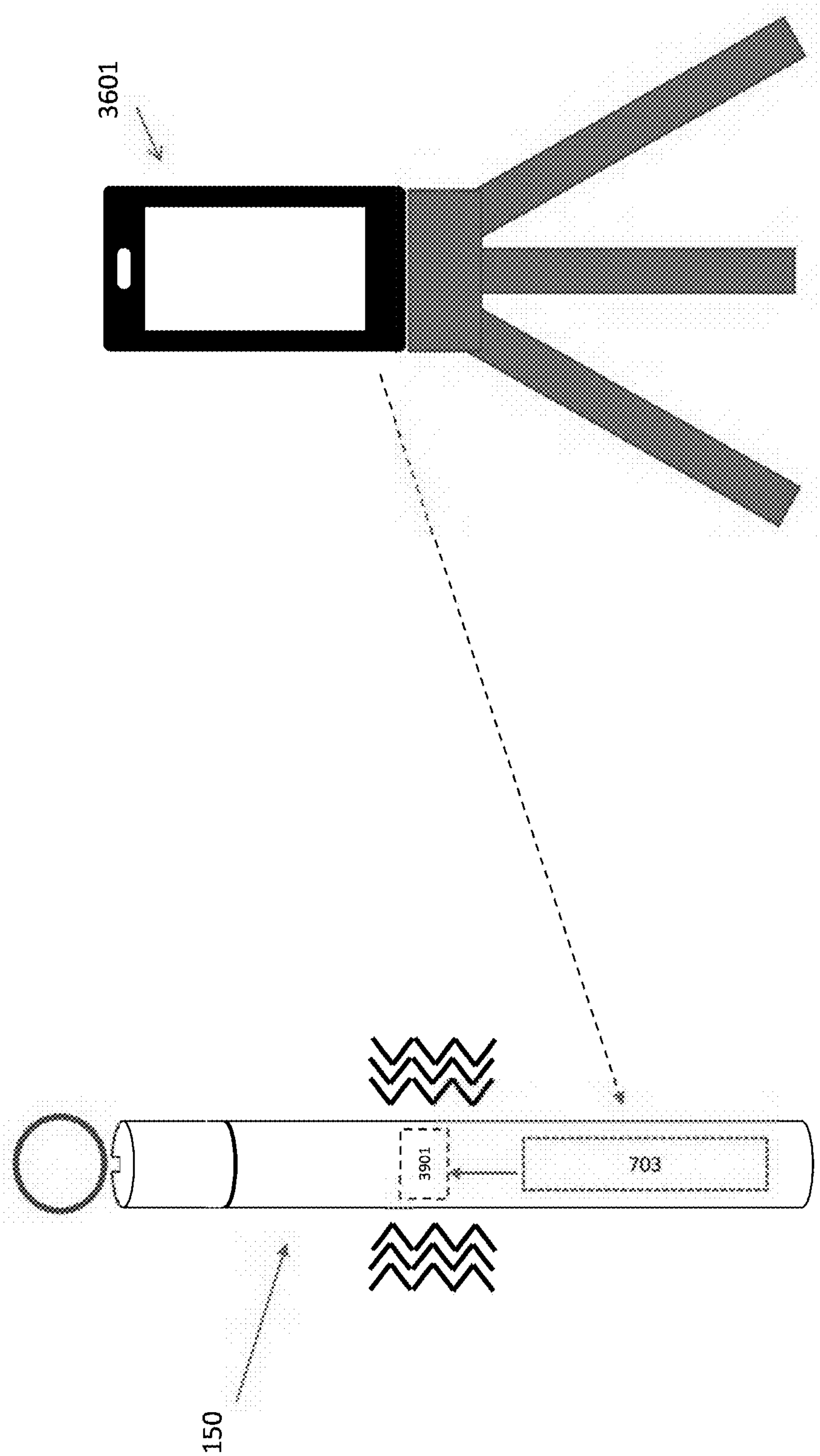
FIG. 39 shows that A motion stabilizer device includes a vibrational element, according to an embodiment.

FIG. 39 shows that the motion stabilizer device 150 includes a vibrational element 3901. Such a vibration element is well understood in the art. The vibration element 3901 is connected to PCBA 703. The application on smartphone 3601 communicates to the communication interface coupled to the PCBA 703, which in turn activates the vibration element 3901 and causes the haptic feedback for the user. The trigger for activating the vibration element may be the visual detection of the cosmetic applicator straying from a boundary or an intended target as described above. Alternatively, it may be based on the motion sensor detecting a deviation in the measurements of the X, Y, and Z sensors in comparison to the normal movement of the adapter as shown in FIG. 34 above (in other words, the vibration may occur in real time during the time region 3401 shown in FIG. 34).

Figure 40:
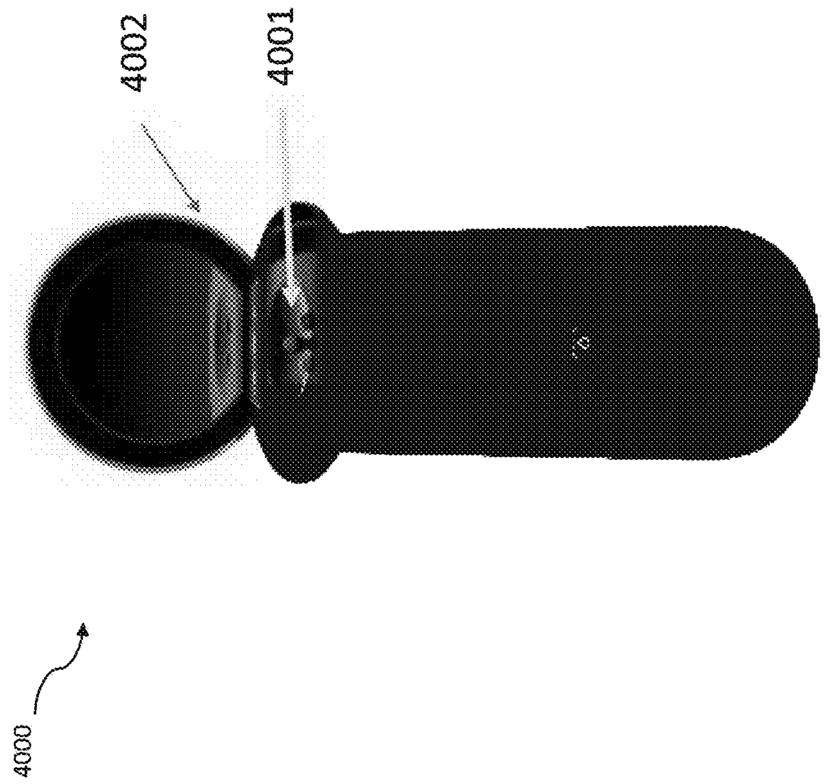
FIG. 40 shows a cosmetic dispensing device that is configured to dispense a plurality of different color cosmetic formulations into a receiving area, according to an embodiment.

In an embodiment, the motion stabilizer device with the above-described universal adapter is configured to operate in conjunction with an external device that dispenses cosmetic material. For instance, FIG. 40 shows a cosmetic dispensing device 4000 that is configured to dispense a plurality of different color cosmetic formulations (for instance three colors) into a receiving area 4001. The different dispensed colors can be mixed together by the user to make a personalized make-up (such as lipstick, foundation, etc.) for a one-time use. The device further includes a detachable compact 4002 that can be removed from the device after the dose of make-up is dispensed. Such a dispensing device is described in U.S. Pub. No. 2022/0240643A1, which is incorporated herein by reference.

Figure 41:
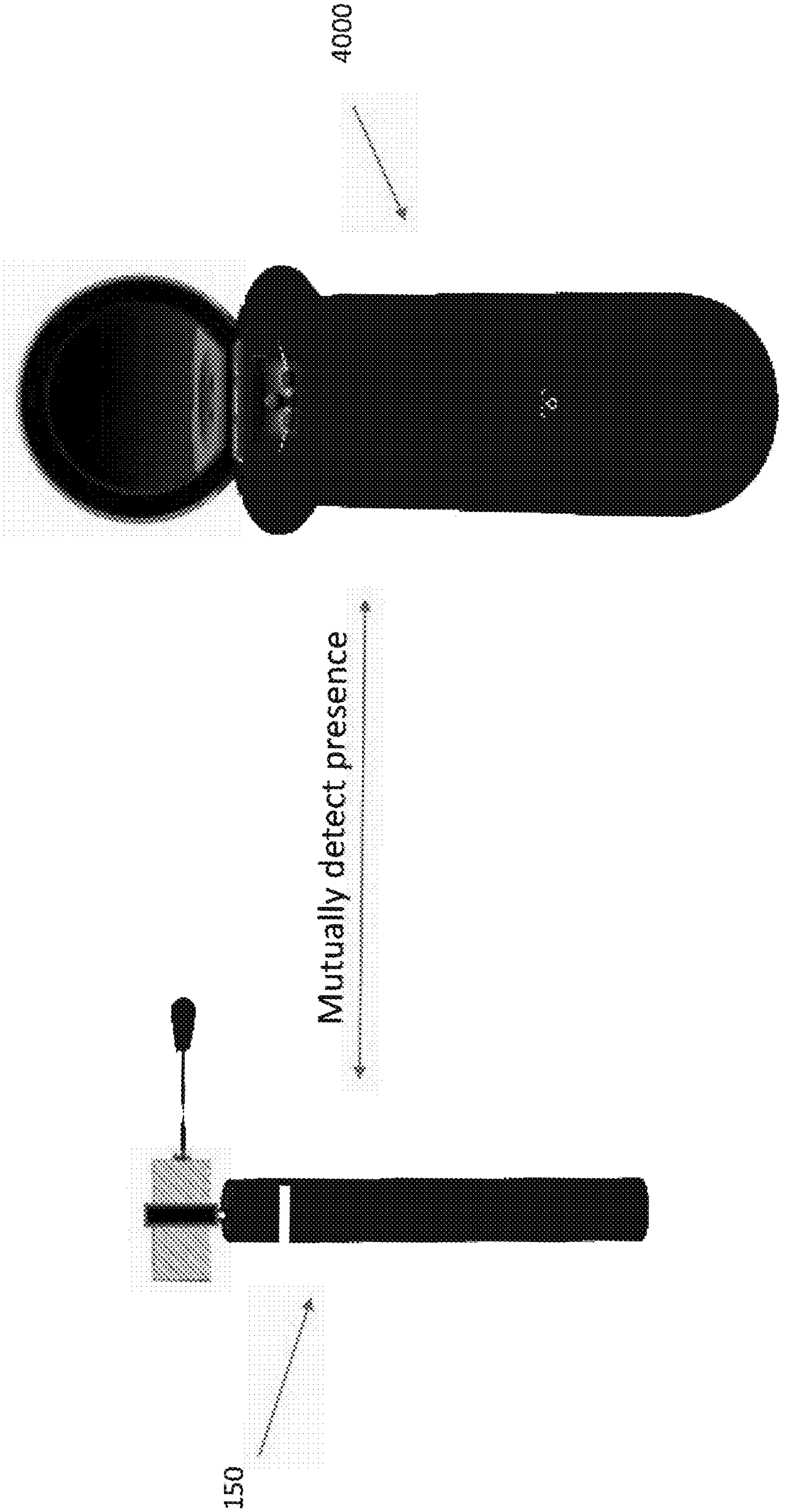
FIG. 41 shows that the motion stabilizer device and the cosmetic dispensing device will mutually detect each other's presence.
Figure 42:
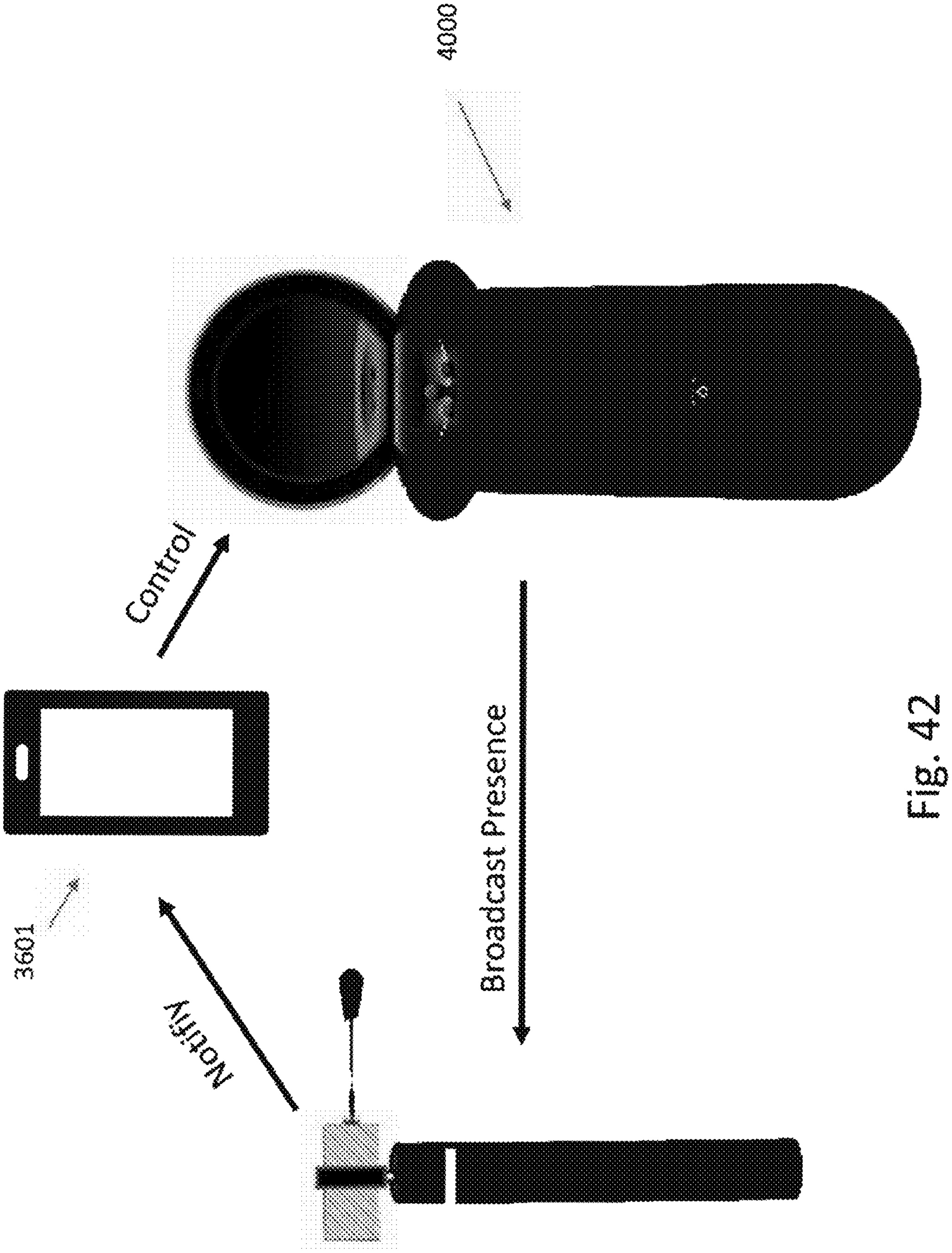
FIG. 42 shows that the motion stabilizer device detects the presence of the cosmetic dispensing device and notifies the user's mobile device of the detection, in an embodiment.

FIG. 41 shows that the motion stabilizer device 150 and the cosmetic dispensing device 4000 will mutually detect each other's presence when they are within a certain proximity to one another. This can be accomplished using via BLE/NFC/RFID communication as was already described above. Alternatively, as shown in FIG. 42, the motion stabilizer device 150 may detect the presence of the cosmetic dispensing device 4000 and notify the user's mobile device 3601 of the detection. The mobile device can be used to control the cosmetic dispensing device 4000 as described in U.S. Pub. No. 2022/0240643A.

The benefit of the motion stabilizer device 150 being able to detect the presence of the cosmetic dispensing device 4000 is that it allows special functionality to be performed by the motion stabilizing device in combination with the universal adapter described above.

For instance, as noted above, the system includes the functionality to auto-detect adapters to activate specific protocols to the motion stabilizer device 150. In this case, the motion stabilizer device 150 performs auto detection of being in close proximity of the cosmetic dispensing device. The motion stabilizer device will load a specific set of protocols developed for use with the cosmetic dispensing device.

Figure 43:
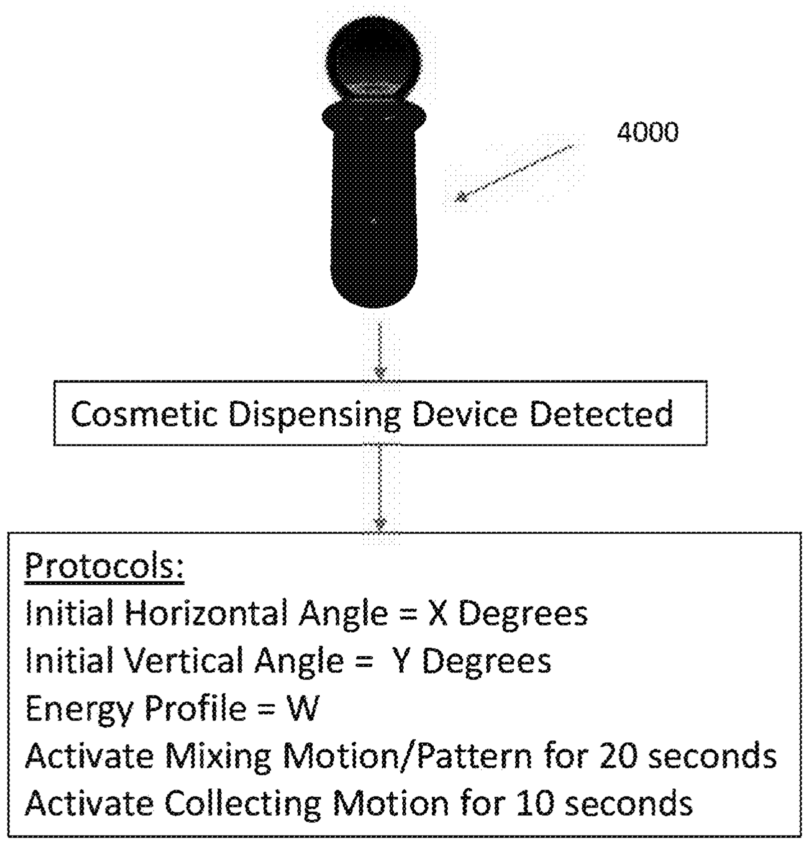
FIG. 43 shows protocols that are retrieved based on the motion stabilizing device detecting the cosmetic dispensing device, according to an embodiment.

For instance, as shown in FIG. 43, the protocols include specific parameters initial angles of orientation of the stabilizer along with settings for energy consumption. Furthermore, the protocols indicate a particular action that is to be caused by the motion stabilizer in combination with the universal adapter. For instance, the protocols indicate that a mixing motion or pattern is to be performed for 20 seconds and then a collecting motion is to be performed for 10 seconds. The mixing motion or pattern is an action that is used by the cosmetic applicator to mix the multiple dispensed colors in the receiving area of the cosmetic dispensing device. The collecting motion is a different type of motion that is used to collect the cosmetic onto the cosmetic applicator for actual use by the user.

Figure 44:
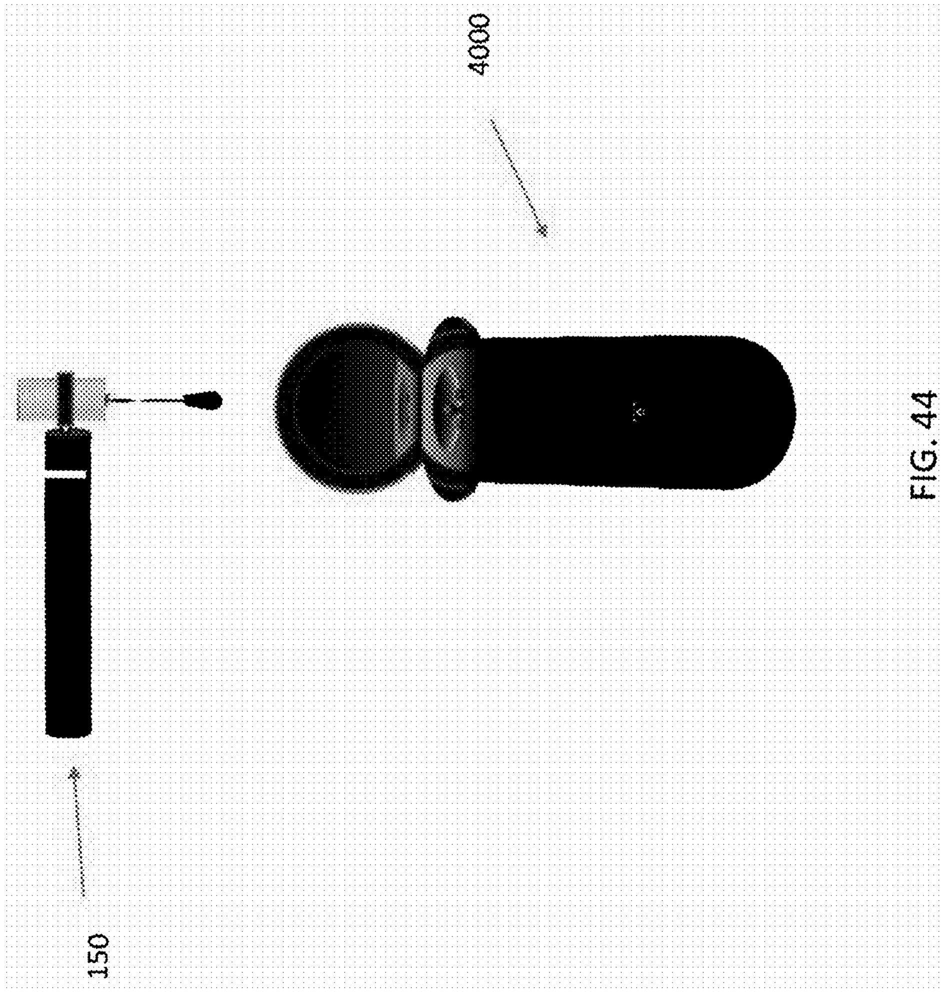
FIG. 44 shows how a user may use the motion stabilizing device to mix a cosmetic that is dispensed from the cosmetic dispensing device, according to an embodiment.

For instance, as shown in FIG. 44, when the user approaches the cosmetic dispensing device with the motion stabilizer device, the user may hold the motion stabilizer device handle so that the cosmetic applicator (in this case a lipstick brush) is directly over the receiving area of the cosmetic dispensing device. When the user moves the motion stabilizer device downward and contacts the receiving area, the sensed contact will trigger the motion stabilizing device to control the cosmetic applicator to move in a mixing motion or pattern that will cause the multiple colors to be mixed and blended together to achieve the user's target color. The mixing motion or pattern can be circular, a FIG. 8 pattern, or any other effect motion to cause the multiple colors to be mixed and blended together. While the present example indicates that this mixing motion or pattern will have a duration of 20 seconds, any amount of time suitable to cause the blending the colors in the receiving area is possible.

After the mixing motion or pattern is completed, according to the protocol, the motion stabilizing device will cause the cosmetic applicator to perform a collecting motion for a predetermined amount of time (10 seconds in this example).

The collecting motion is similar to a scraping motion that is designed to allow the brush to collect the cosmetic for actual use. This may involve an increase in pressure and use a slower movement.

When the collecting motion is completed, then the cosmetic applicator is ready for use as described above.

While the embodiment above describes the use of the cosmetic applicator itself to mix and collect the cosmetic formulation that is dispensed from the cosmetic dispensing device, in an alternative embodiment, a special brush may be used for the mixing.

Figure 45B:
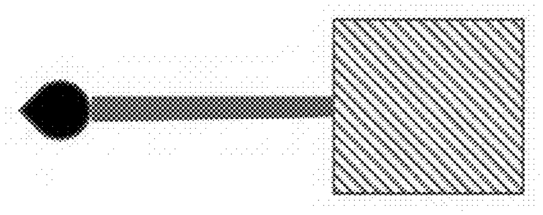
FIG. 45A-45B show a dual brush design, according to an embodiment.
Figure 45A:
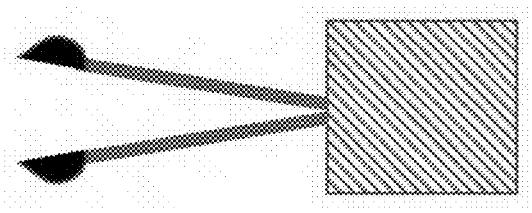

FIG. 45A shows a dual brush design that can be configured to be in an open position as shown in FIG. 45A and a closed position as shown in FIG. 45B in which the structure becomes a single brush design and acts as the cosmetic applicator. In the open position, the dual brush is used to more efficiently mix the doses of the dispensed colors in the receiving area of the cosmetic dispensing device. This can be accomplished by rotating the dual brushes when sensing contact in the receiving area.

Upon completion of the mixing process, the cosmetic applicator can be controlled to close or collapse the dual brush arrangement to form what is shown in FIG. 45B, and effectively form a single brush for the collecting process and also the actual use of the cosmetic applicator. The opening and closing of the brush is accomplished by a spring hinge mechanism as known in the art.

While the above example describes a dual brush design, embodiments are not limited to this number of brushes, and it can also be a "tri-brush design in which 3 brushes can be closed to form a single brush.

Figure 46:
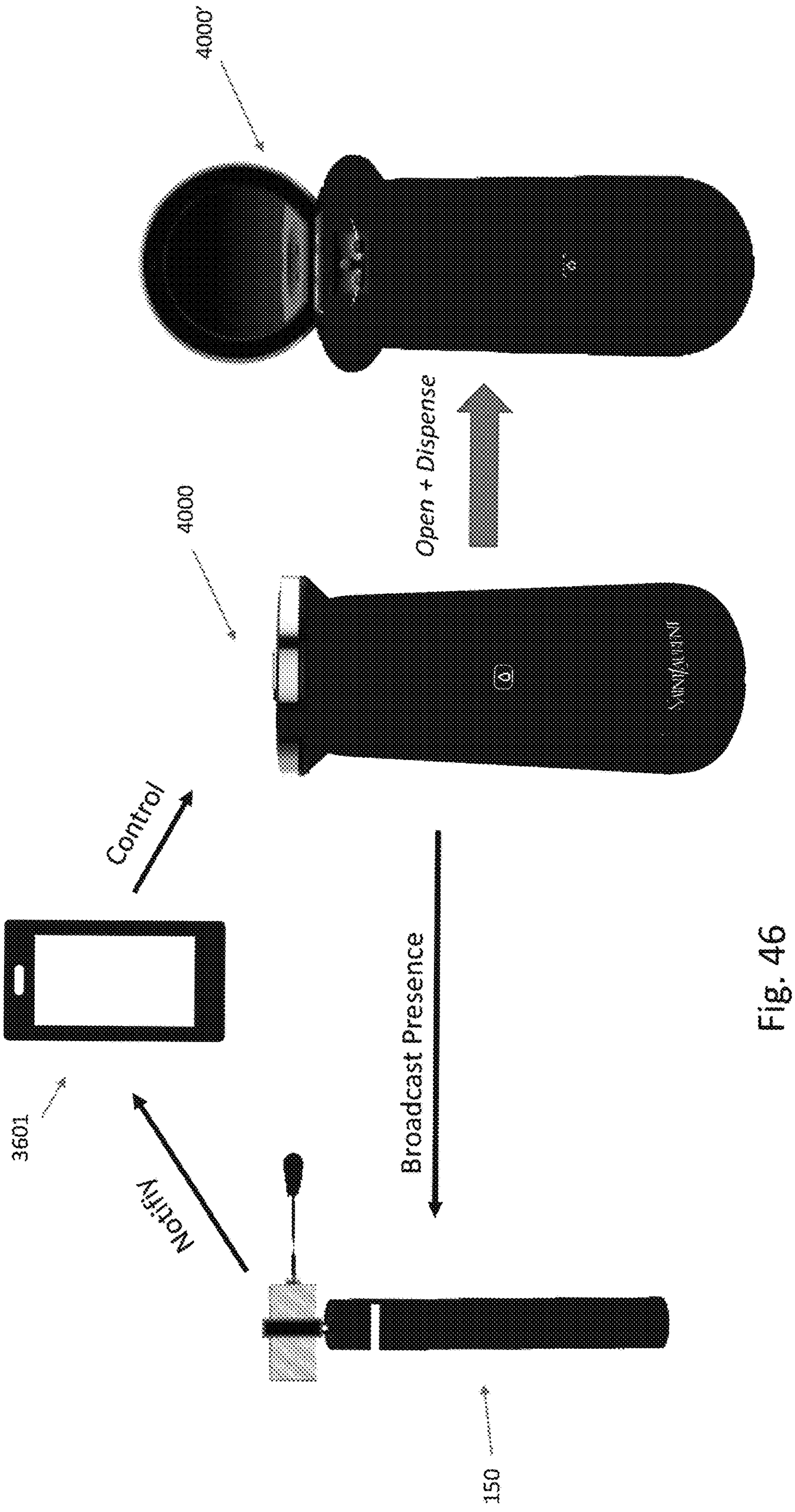
FIG. 46 shows actions taken by the cosmetic dispensing device based on the presence of the motion stabilizing device, according to an embodiment.

While the above examples describe how the motion stabilizing device adapts to detecting the presence of the cosmetic dispensing device, the cosmetic dispensing device also adapts to the presence of the motion stabilizing device. As shown in FIG. 46, to further assist a person that has trouble with unintentional hand movements, when the presence of the cosmetic dispensing device 4000 is detected to be in proximity of the motion stabilizer 150, the mobile device is notified accordingly. The mobile device 3601 then provides control to the cosmetic dispensing device to perform at least one of two automated actions: (1) open the compact lid and (2) dispense one dose of the personalized cosmetic color ingredients into the receiving area.

Figure 47:
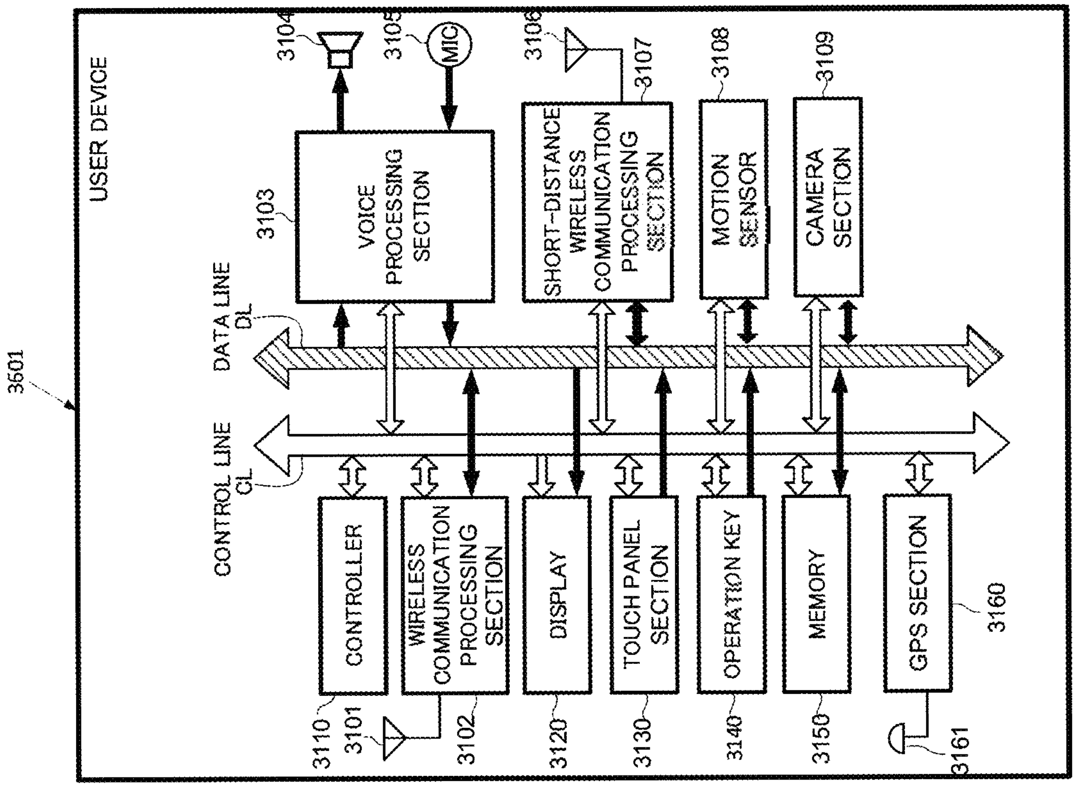
FIG. 47 is a detailed block diagram illustrating an exemplary user device according to certain embodiments.

FIG. 47 is a more detailed block diagram illustrating an exemplary user device 3601 according to certain embodiments of the present disclosure. In certain embodiments, user device 3601 is a smartphone. However, the skilled artisan will appreciate that the features described herein may be adapted to be implemented on other devices (e.g., a laptop, a tablet, a server, an e-reader, a camera, a navigation device, etc.). The exemplary user device 3601 includes a controller 3110 and a wireless communication processor 3102 connected to an antenna 3101. A speaker 3104 and a microphone 3105 are connected to a voice processor 3103.

The controller 3110 may include one or more Central Processing Units (CPUs), and may control each element in the user device 3601 to perform functions related to communication control, audio signal processing, control for the audio signal processing, still and moving image processing and control, and other kinds of signal processing. The controller 3110 may perform these functions by executing instructions stored in a memory 3150. Alternatively or in addition to the local storage of the memory 150, the functions may be executed using instructions stored on an external device accessed on a network or on a non-transitory computer readable medium. As described above in relation to FIG. 47, the controller 3110 may execute instructions allowing the controller 3110 to function as the display control unit 3211, operation management unit 3212 and game management unit 3213 depicted in FIG. 47.

Obviously, numerous modifications and variations of the present invention are possible in light of the above teachings. It is therefore to be understood that within the scope of the appended claims, the invention may be practiced otherwise than as specifically described herein.

The invention claimed is:

1. A system that stabilizes an applicator in response to the motion caused by a user, comprising:
- a mobile user device that is configured to execute an application;
- a motion stabilizer; and
- an adapter that holds a cosmetic applicator,
- wherein the motion stabilizer includes
  - a receiver configured to be coupled with the adapter;
  - at least one sensor configured to detect a movement caused by a user;
  - circuitry configured to determine a compensation movement to offset the detected movement; and
  - at least one motion generation device embedded in the receiver configured to control a motion of the cosmetic applicator according to the determined compensation movement,
- wherein the application is configured to
  - capture an image of the user prior to a session of applying a cosmetic using the cosmetic applicator;
  - capture an image of the user after the session of applying a cosmetic using the cosmetic applicator;
  - detect an error in applying the cosmetic to a portion of the user's body;
  - detect a deviation in the movement of the cosmetic applicator during the session when the error is detected; and
  - adjust settings for the motion stabilizer to compensate for the deviation.

2. The system according to claim 1, wherein the adapter includes a motion sensor that outputs data to the application indicating movement of the adapter during the session, and the application detect the deviation in the movement of the cosmetic applicator during the session based on the outputted data.

3. The system according to claim 2, wherein the motion sensor is an accelerometer.

4. The system according to claim 1, wherein the application displays a realtime mirror image of the user during the session, and detects a location of the cosmetic applicator and a location of a target portion of the user's body to which the cosmetic is to be applied.

5. The system according to claim 4, wherein the application outputs realtime feedback to the user when deviation in the movement of the cosmetic application is occurring in realtime.

6. The system according to claim 5, wherein the realtime feedback is a display of an indicator on the mobile user device to correct a position of the cosmetic applicator.

7. The system according to claim 5, wherein the motion stabilizer further includes a vibrational element, and the realtime is an instruction to activate the vibrational element.

8. The system according to claim 1, wherein the application is configured to display a target object that detects an initial deviation of movement by a user prior to the session, and to initially adjust settings for the motion stabilizer to compensate for the detected initial deviation.

9. The system according to claim 1, wherein the application is configured to detect the error in applying the cosmetic to a portion of the user's body based on detecting that an application of the cosmetic crosses a visible boundary of a natural feature of the user.

10. The system according to claim 1, wherein the application is configured to detect the error in applying the cosmetic to a portion of the user's body based on a machine learning model that is trained based on presenting images to a plurality of users and obtaining feedback from the users on a level of magnitude of error in applying make-up for those images.

11. The system according to claim 1, wherein the application is configured to adjust settings for the motion stabilizer to compensate for the deviation based on a deep learning model that is trained based on receiving inputs of a user's image of an error applying a cosmetic during a session, data outputted from a motion sensor during the session, and compensation parameters used in a motion stabilizer that corrected the error in the make-up application process.

12. A method implemented by a system that stabilizes an applicator in response to the motion caused by a user, the system including a mobile user device that is configured to execute an application, a motion stabilizer, and an adapter that holds a cosmetic applicator, wherein the motion stabilizer includes a receiver configured to be coupled with the adapter; at least one sensor configured to detect a movement caused by a user; circuitry configured to determine a compensation movement to offset the detected movement; and at least one motion generation device embedded in the receiver configured to control a motion of the cosmetic applicator according to the determined compensation movement, the method comprising:

by the application of the mobile user device, capturing an image of the user prior to a session of applying a cosmetic using the cosmetic applicator;

capturing an image of the user after the session of applying a cosmetic using the cosmetic applicator;

detecting an error in applying the cosmetic to a portion of the user's body;

detecting a deviation in the movement of the cosmetic applicator during the session when the error is detected; and adjusting settings for the motion stabilizer to compensate for the deviation.

* * * * *